(12) United States Patent
Fromme et al.

(10) Patent No.: US 6,988,610 B2
(45) Date of Patent: Jan. 24, 2006

(54) CONVEYOR BELT INSPECTION SYSTEM AND METHOD

(75) Inventors: Christopher C. Fromme, Sycamore, PA (US); David J. Stager, Pittsburgh, PA (US); Thomas E. Pilarski, Wexford, PA (US); Bruce Bancroft, McMurray, PA (US); Timothy Ennis Hegadorn, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 324 days.

(21) Appl. No.: 10/341,735

(22) Filed: Jan. 14, 2003

(65) Prior Publication Data

US 2003/0168317 A1 Sep. 11, 2003

Related U.S. Application Data

(60) Provisional application No. 60/348,634, filed on Jan. 14, 2002.

(51) Int. Cl.
*B65G 43/00* (2006.01)

(52) U.S. Cl. .................. 198/502.1; 198/810.02
(58) Field of Classification Search .............. 198/323, 198/502.1, 502.4, 810.02, 810.03; 382/149
See application file for complete search history.

(56) References Cited

U.S. PATENT DOCUMENTS

| 2,425,575 A | 8/1947 | Suloff |
| 3,189,166 A | 6/1965 | Ziller |
| 3,512,662 A | 5/1970 | Strydorn |

(Continued)

FOREIGN PATENT DOCUMENTS

| DE | 28 54 562 | 6/1980 |
| DE | 35 17 314 A1 | 1/1986 |
| DE | 35 17 314 A1 | 2/1986 |
| DE | 36 11 125 A | 10/1987 |
| DE | 41 11 358 A | 10/1992 |
| DE | 42 40 094 A1 | 6/1994 |
| DE | 44 44 264 C1 | 4/1996 |
| DE | 199 29 099 A1 | 12/2000 |
| DE | 101 00 813 A1 | 8/2001 |
| JP | 359092817 A | 5/1984 |

OTHER PUBLICATIONS

Patent Cooperation Treaty ("PCT") International Search Report.
Conveyor Belt Monitoring, available at www.beltscan.com.au/index.htm.
Blum, Dieter W., *Scanning Steel Cord Conveyor Belts With the "Belt C.A.T.™" System*, available at www.pixii.com/mdr/htm (1997–2003).
Asata, Carrie, *Keep Material on the Move*, available at http://rockproducts.com/ar/rock_keep_material_move_2/.
Harrison, A., *Review of Conveyor Belt Monitoring Research in Australia*, available at www.saimh.co.za/beltcon/Beltcon3/paper319.html.
PHOENIX, Products, available at www.phoenix-ag.com/phxn/do/layoutid.1/language.2/documentid.29977841.
Damaged Belt Detector, available at www.conveyorcomponents.com/ccdb.html.
Scanbelt (PTY) Ltd., available at www.scanbelt.co.za/Products.htm.

*Primary Examiner*—James R. Bidwell
(74) *Attorney, Agent, or Firm*—Kirkpatrick & Lockhart LLP

(57) ABSTRACT

Systems and techniques for detecting and reporting conditions of a conveyor belt by receiving image data from at least one camera structured and arranged to capture an image of a portion of a conveyor belt, detecting an object in the portion of the conveyor belt based on the received image data, and generating status information associated with the portion of the conveyor belt based on the detected object.

70 Claims, 66 Drawing Sheets

U.S. PATENT DOCUMENTS

| | | |
|---|---|---|
| 3,742,477 A | 6/1973 | Enabnit |
| 3,922,661 A | 11/1975 | Enabnit et al. |
| 3,956,632 A | 5/1976 | Hall et al. |
| 4,087,800 A | 5/1978 | Lee |
| 4,138,010 A | 2/1979 | Pidgeon et al. |
| 4,149,624 A | 4/1979 | Douty et al. |
| 4,172,515 A | 10/1979 | Wochnowski |
| 4,229,735 A | 10/1980 | Houck |
| 4,349,883 A | 9/1982 | Doljack |
| 4,437,563 A | 3/1984 | Oriol |
| 4,447,807 A | 5/1984 | Klein et al. |
| 4,463,434 A | 7/1984 | Haylett et al. |
| 4,464,654 A | 8/1984 | Klein |
| 4,577,502 A | 3/1986 | Cunningham |
| 4,621,727 A | 11/1986 | Strader |
| 5,096,044 A | 3/1992 | Biebel |
| 5,133,448 A | 7/1992 | Van Niekerk |
| 5,134,661 A | 7/1992 | Reinsch |
| 5,421,449 A | 6/1995 | Coxon |
| 5,519,793 A | 5/1996 | Grannes |
| 5,714,998 A | 2/1998 | Wheeler |
| 5,732,147 A | 3/1998 | Tao |
| 5,753,866 A | 5/1998 | Ikeda et al. |
| 5,815,198 A | 9/1998 | Vachtsevanos et al. |
| 5,844,668 A | 12/1998 | Lepain et al. |
| 5,973,776 A | 10/1999 | Matsushita |
| 5,994,712 A | 11/1999 | Mack |
| 6,032,787 A | 3/2000 | Kellis |
| 6,047,814 A | 4/2000 | Alles et al. |
| 6,131,727 A | 10/2000 | Nelson |
| 6,157,730 A | 12/2000 | Roever et al. |
| 6,167,150 A | 12/2000 | Michael et al. |
| 6,259,526 B1 | 7/2001 | Pace et al. |
| 6,266,437 B1 | 7/2001 | Eichel et al. |
| 6,291,991 B1 | 9/2001 | Schnell |
| 6,702,103 B1 * | 3/2004 | Küsel .................... 198/810.03 |
| 2003/0000808 A1 * | 1/2003 | Kusel ...................... 198/502.1 |

* cited by examiner

```
Xsum = Ysum = 0
Npix = 0

For each pixel p in the patch image

Compute the horizontal gradient Gx(p)
            and vertical  gradient Gy(p)
    Edge magnitude   M(p) = Gx2(p) + Gy2(p)
    Edge angle       A(p) = arctan( Gy(p) / Gx(p) )
        // A(p) is in the range [-pi/2..pi/2]
        // Convert A(p) to degrees and add 90
        // which makes the range [0..180]
    If M(p) > 3 * Mean(M)    // "strong edge"
        Record angle A(p) in a histogram Hist
        Xsum = Xsum + p(x)   // add the x-coordinate of p
        Ysum = Ysum + p(y)   // add the y-coordinate of p
        Npix = Npix + 1

Xcenter = Xsum / Npix
Ycenter = Ysum / Npix
```

FIG. 60

| -1 | -1 | -1 | -1 | -1 |
|----|----|----|----|----|
| -1 | -1 | -1 | -1 | -1 |
| 0  | 0  | 0  | 0  | 0  |
| 1  | 1  | 1  | 1  | 1  |
| 1  | 1  | 1  | 1  | 1  |

Vertical gradient filter

| -1 | -1 | 0 | 1 | 1 |
|----|----|---|---|---|
| -1 | -1 | 0 | 1 | 1 |
| -1 | -1 | 0 | 1 | 1 |
| -1 | -1 | 0 | 1 | 1 |
| -1 | -1 | 0 | 1 | 1 |

Horizontal gradient filter

CONVEYOR BELT INSPECTION SYSTEM AND METHOD

This application claims priority to provisional patent application Ser. No. 60/348,634, which was filed on Jan. 14, 2002 and is incorporated by reference in its entirety.

BACKGROUND

In underground mines such as coal mines, conveyor belt systems often are utilized to remove the payload from the mine. The conveyor belt system of a typical coal mine may have as many as twenty belts, and each belt may be as long as 20,000 feet. In general, a belt is made from a rubber/fabric laminate and assembled by fastening together several belt sections end-to-end to form a continuous belt. The sections of the belt often are joined using metal clips laced together with steel cable. Namely, a row of clips is riveted to the end of one belt section and laced with a row of clips riveted to the end of another belt section. When installed, the two sets of clips together form a splice that joins the belt sections. Because the lengths of the sections that form a belt may vary, there is generally no uniformity to the spacing of splices.

As a splice wears, the clips can break, or be torn off the belt entirely, and the belt will pull itself apart. A broken belt is dangerous and can cause tons of material to be spilled, resulting in the shut down of production and requiring expensive clean up and repairs. A conservative estimate of failures is that each belt of a conveyor belt system in an underground mine fails once per year at a cost of on average $100,000 in lost revenue for the mine per failure. Assuming a belt system with twenty belts, this translates to a conservative estimate of a revenue loss of $2 million per year attributed to belt failures.

SUMMARY

In one general aspect, an inspection system for detecting and reporting conditions of a conveyor belt may include a controller for receiving image data from at least one camera structured and arranged to capture an image of a portion of a conveyor belt, for detecting an object in the portion of the conveyor belt based on the received image data, and for generating status information associated with the portion of the conveyor belt based on the detected object. The system may further include a user interface, in communication with the controller, configured to display a visual representation of the status information.

Implementations may include one or more of the following features. For example, the controller may classify the detected object and analyze the detected object based on object classification. For example, the detected object may include a mechanical splice. The controller may detect the mechanical splice by edge filtering the image data, by searching for a zipper pattern in image data, and/or by searching for a hole pattern in the image data. The status information may include a score assigned to the detected mechanical splice by the controller. The score may be based on a zipper hole pattern and/or a number of functional clips included in detected mechanical splice.

The detected object also may include a vulcanized splice. The controller may detect the vulcanized splice by locating at least one fiduciary marking corresponding to the location of the vulcanized splice. The controller may locate the at least one fiduciary marking by edge filtering, for example. The fiduciary marking may be vulcanized to the conveyor belt and include at least one of a mark, patch, pattern, shape, line or grid. The controller may locate the center and/or a rotation angle of the at least one fiduciary marking. In some cases, the controller may locate a pair of fiduciary markings bounding the vulcanized splice.

The detected object may include a material defect in the belt such as a hole, rip, worn edge, splice, score, or gouge in the conveyor belt. The detected object also may include a belt marking. The controller may analyze the belt marking for distortion (e.g., stretching) indicative of a defective condition of the conveyor belt and/or locate a center of one or more belt markings. The belt marking may be vulcanized to the conveyor belt and include at least one of a mark, patch, pattern, shape, line, or grid.

The detected object may include reflected light. The reflected light may be generated by a focused light source structured and arranged to direct focused light at the conveyor belt. The focused light source may include a laser. The controller may generate a range profile based on properties of the reflected light, and the status information may include a three-dimensional topography of the conveyor belt based on the range profile.

The status information also may include a digital image of the detected object and/or a plurality of digital images of the detected object captured over a period of time. The images may show degradation of the detected object over time. The status information may include an alarm condition.

The controller may be configured to assign an identification tag to a detected object. The identification tag may be assigned based on at least one of a reference object, a point-of-origin, recognized pattern, correlation between images, a health score, and object degradation.

The system may include an encoder for monitoring speed of the conveyor belt and/or a remote element, in communication with the controller, for enabling remote access to the status information.

Aspects of the present invention may be implemented by an apparatus, method, and/or program stored on a computer readable medium.

DESCRIPTION OF THE DRAWINGS

FIG. 60 illustrates one embodiment of computing edge angle histogram and center of mass.

FIG. 61 illustrates one embodiment of filters for computing the magnitude and angle of edges.

FIG. 77 illustrates one embodiment of a mechanical splice scoring configuration interface.

FIG. 79 illustrates one embodiment of a fiducial detection configuration interface.

DETAILED DESCRIPTION

In one general aspect, the present invention is directed to systems and techniques for detecting defective conditions in a conveyor belt that may contribute to belt failure and for alerting management and/or maintenance personnel of such conditions prior to belt failure. For simplicity, the basic components of such systems and techniques are provided. However, as would be understood by one of ordinary skill in the art, the systems and techniques described below may include various other components and structures in actual implementation consistent with aspects of the present invention.

Figure 1:
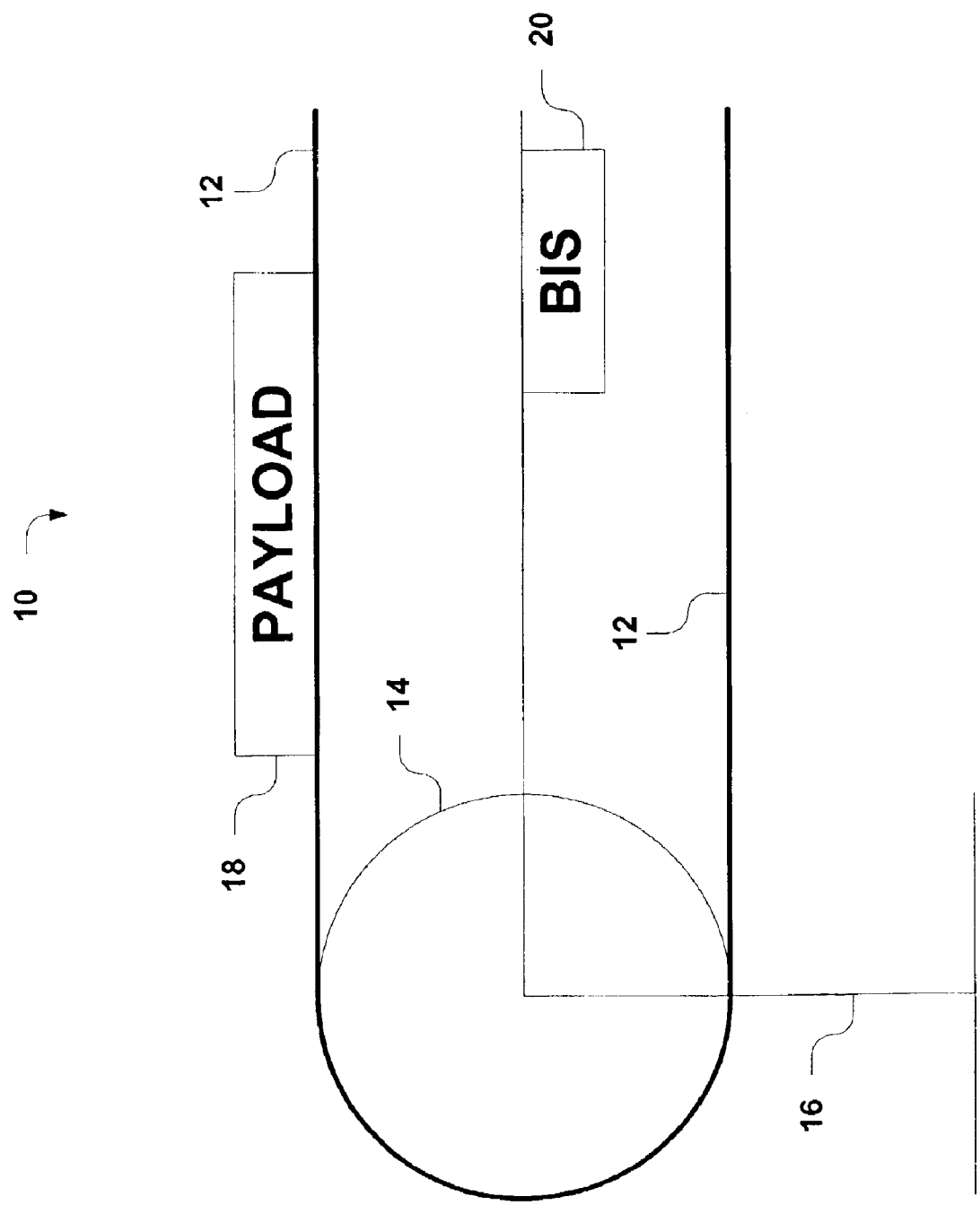
FIG. 1 illustrates one embodiment of a conveyor belt system.

One embodiment of a conveyor belt system 10 is illustrated in FIG. 1. As shown, the conveyor belt system 10 includes a belt 12 that forms a continuous loop rotated by the turning of cylindrical drums or rollers 14 mounted to a chassis 16. In general, a payload 18 such as coal or other material may be carried and transported on the outer surface of the belt 12. A typical operating speed of the belt 12 may be around 800 feet per minute. Other operating speeds are contemplated and the speed of the belt 12 may vary during the course of use. For instance, as the belt 12 is started and stopped, the speed of the belt 12 may ramp up to its operating speed or ramp down to a halt.

In the embodiment depicted in FIG. 1, the conveyor belt system 10 includes a belt inspection system (BIS) 20 for detecting and reporting conditions of the conveyor belt 12. In general, the BIS 20 is configured to handle variations in the speed of the belt 12 and operate at a rate high enough to process and detect conditions at the maximum speed of the belt 12. In some embodiments, the BIS 20 may be positioned over and aimed at the inner surface of the belt 12, as shown, such that the BIS 20 is not aimed at portions of the belt 12 where the payload 18 is carried. In some case, the BIS 20 may be aimed at the payload side of the belt 12. Generally, a spot may be found to monitor a portion of the payload side of the belt 12 that is not covered by the payload 18. The BIS 20 may be mounted to the chassis 16, suspended from the chassis 16, and/or supported over the belt 12 such that the BIS 20 is properly positioned to detect conditions of the conveyor belt 12.

In some implementations, the BIS 20 may automatically monitor the quality of belt splices where the belt is most likely to fail. For example, the BIS 20 may perform mechanical splice detection, vulcanized splice detection, and/or other types of splice detection. With regard to mechanical splice detection, the BIS 20 may detect the mechanical splices, generate a digital image of the splice, determine the number of functional splice clips (i.e. "score"), alert mine personnel to the condition (e.g., Good, Fair or Bad) of the mechanical splices used to join two pieces of mine conveyor belt together, uniquely identify the splice by location on the belt via one of several methods, keep a record of the splices for viewing a history of deterioration, and/or display the mechanical splice on a user interface and publish the image over a network (e.g., Ethernet) to a web-based application.

With regard to vulcanized splice detection, the BIS 20 may detect vulcanized splices by use of a fiducial marking vulcanized to either end of the splice, detect the center of each fiducial marking, determine the distance from center to center, use the center to center distance to determine the historic stretch of the splice which may indicate approaching splice failure, uniquely identify the splice by location on the belt via one or several methods, keep a record of the splices for viewing a history of deterioration, and/or display the splice on a user interface and publish the image over a network (e.g., Ethernet) to a web-based application.

In some cases, the BIS 20 may detect belt defects in addition to or independent of performing splice detection. Examples of defects include, but are not limited to, holes, rips, edge wear, "flappers", gouging, "pizza cutters" and/or any other defect which left un-repaired may cause splice or belt failure. In some implementations, the BIS 20 may generate a topography of the belt which is capable of being examined for geometric defects. In other implementations, the BIS 20 may detect deformation in one or more belt markings (e.g., fiducial markings) indicating splice failure and/or excessive wear of the belt. Images may be displayed on a user interface and/or may be published over a network (e.g., Ethernet) to a web-based application.

Figure 2:
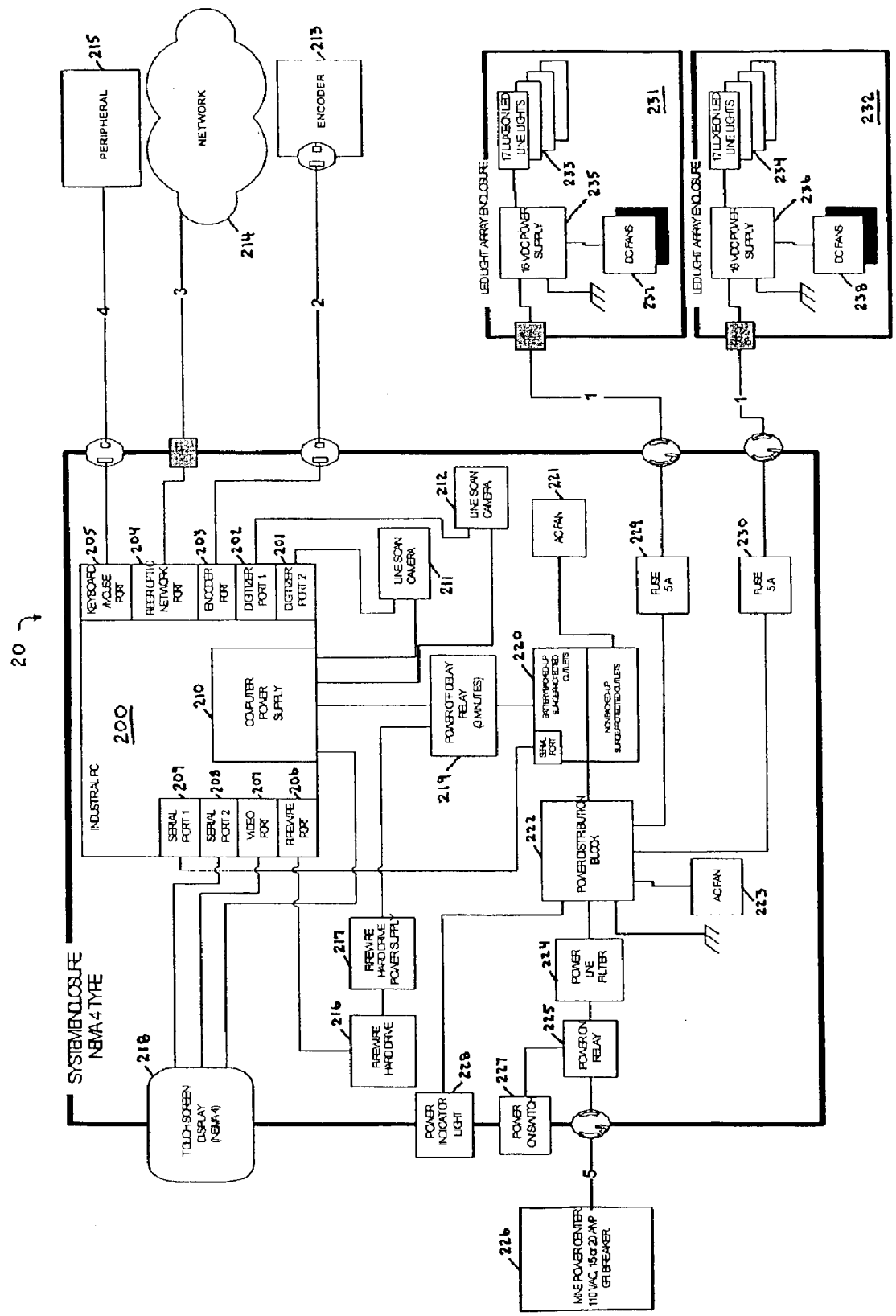
FIG. 2 illustrates one embodiment of a belt inspection system.

One embodiment of a BIS 20 is illustrated in FIG. 2. As shown, the BIS 20 includes a controller 200 in communication with one or more detectors. In general, the controller 200 may be implemented as one or more computers and/or computer systems for performing the functions described herein. Examples include, but are not limited to, a general-purpose computer, a special-purpose computer, a personal computer (PC), a workstation, a network server, a terminal, a virtual machine, a laptop computer, a microprocessor, an integrated circuit, or any other device, machine, tool, equipment, component, or some combination thereof capable of responding to and executing instructions.

As depicted, the controller 200 may include ports such as, for example, a first digitize port 201, a second digitizer port 202, an encoder port 203, a network port 204, an input/output (I/O) port 205, a memory port 206, a video port 207, a first serial port 208, and a second serial port 209. The ports 201–209 may be used to connect the controller 200 through wired and/or wireless connections to various other components of the BIS 20. The controller 200 also may include a power supply 210 (e.g., 110 VAC) for supplying power to the controller 200 among other elements, as described below.

In one implementation, the power supply 210 powers detectors including a first camera 211 and a second camera 212 that are structured and arranged to provide the controller 200 with images of a conveyor belt. Upon installation, the two images, captured respectively by the first camera 211 and the second camera 212, are merged through an overlap and an offset adjustment to provide a single image frame. Such adjustment and others (e.g., camera focus) may be performed locally and/or performed remotely when the BIS 20 is connected to a network. While the use of dual cameras 211, 212 is advantageous, it is contemplated that the BIS 20 may employ a single camera capable of imaging the entire width of the belt in other embodiments.

In one implementation, the cameras 211, 212 are line scan cameras attached to the controller 200 through digitizer ports 201, 202. Each of the cameras 211, 212 may provide a digitized image containing one row of pixels that spans a little over half the belt. Given a belt speed of 800 feet per minute and a requirement of 50 pixels per inch resolution, for example, each of the cameras 211, 212 may capture a line of the image at about 8000 times per second. In such a case, the cameras 211, 212 generate 4096 pixels per line (covering 82 inches of belt width) yielding roughly 32 megabytes of data per second. While line scan cameras are used in this embodiment, it is contemplated that the BIS 20 may employ other types of cameras such as one or more area scan cameras, for instance.

In one embodiment, the encoder port 203 connects the controller 200 to an encoder 213. In general, the encoder 213 may perform functions for computing the current belt speed and position, computing desired digitized line rate based on the current belt speed, and recording the belt speed—including monitoring the amount of time the belt is idle. The controller 200 may include a PC interface card (e.g., PCI 6601) for powering the encoder 213 at low voltage.

While the use of the encoder 213 may not be required in all cases, it is practical to do so. The line scan cameras 211, 212 capture an image that includes one line of pixels across the belt. To provide image-to-image uniformity and a fixed image resolution, then line density in the long axis of the belt should be controlled. This may be accomplished using the encoder 213 by adjusting the camera firing rate to the current (actual) belt speed. In the absence of an encoder 213, the user may set the camera firing rate based on a fixed (approximate) belt speed which may result in distorted images on belt start-up and shut-down.

Another advantage of the encoder 213 is that if user inputs into the system an accurate count of the number of splices on the belt, then at the interface on the physical installation the user can see updated in real time the distance any splice is from the system and the time before the splice will return. This is useful when one is trying to bring a splice to be remade to the splicing station because belts are frequently broken as they are jogged to get an offending splice to the splicing station.

The network port 204 may connect the controller to a mine network 214. The mine network 214 may include, or form part of, one or more of: a local area network (LAN), a wide area network (WAN), the Internet, the Web, a telephony network (e.g., analog, digital, wired, wireless, PSTN, ISDN, or xDSL), a radio network, a television network, a cable network, a satellite network, and/or any other wired or wireless communications network configured to carry data. The mine network 214 may include one or more elements, such as, for example, intermediate nodes, proxy servers, firewalls, routers, switches, adapters, sockets, and wired or wireless data pathways, configured to direct and/or deliver data. According to one embodiment, the mine network 214 may communicate inspection data to a remote display unit (not shown) so that a belt may be inspected from a remote location. Examples of a remote display device include, but are not limited to, a remote personal computer (PC), workstation, server, laptop computer, web-enabled telephone, web-enabled personal digital assistant (PDA), microprocessor, integrated circuit, or any other component, machine, tool, equipment, or some combination thereof.

The I/O port 205 may connect to the controller 200 to one or more peripheral devices 215 for inputting and/or outputting information. Examples of peripheral devices 215 include, but are not limited to, a mouse, a keyboard, a display monitor with or without a touch screen input, a mobile phone, a personal digital assistant, a printer, a facsimile machine or any other device for inputting and/or outputting data.

The memory port 206 may connect the controller 200 to a storage device 216 for storing and transferring data. In one embodiment, the storage device 216 may include a removable disk such as, for example, a FireWire hard drive. This allows quick removal of datalogged images for system improvements. As shown, the storage device 216 may be powered by a separate power supply 217.

The video port 207 and the first serial port 208 may connect the controller 200 to a UI 218. In one embodiment, the UI 218 may include a display such as, for example, a NEMA 4 touch screen display. In general, the UI 218 allows a user to view digitized images captured by the cameras 201, 202 and to configure the system. As shown, the UI 218 also may be powered by the power supply 210.

The power supply 210 may be connected through a power off delay relay 219 to a battery backup or uninterruptible power supply (UPS) 220. The UPS 220 may include battery backed-up surge protected outlets as well as non backed-up surge protected outlets and may be connected to the controller 200 through the second serial port 209. In one implementation, the UPS may provide back-up power, for various components of the BIS 20, including the power supply 210 of the controller 200 and the power supply 217 for the storage device 216.

As shown, the UPS 220 and may be cooled by a fan 221 and further connected to a power distribution block 222, which also may be cooled by a fan 223. The power distribution block 222 may be connected through a power line filter 224 and a power on relay 225 to the mine power center 226. As the overall system may pull around 4000 watts of power, extension cords from the power center 226 may be infeasible due to voltage drops. The power center 226 may include 480 AC outlets for connecting to the power distribution block 222. The power line filter 224 may offer a transformer and circuit breaker protection for the system. A power on switch 227 connected to the power on relay 225 and a power indicator light 228 may allow the safe operation and visual status of the 480 AC input.

The power distribution block 222 may be connected through a first fuse 229 and a second fuse 230, respectively to a first light array 231 and a second light array 232. In general, the light arrays 231, 232 enable the use of the system in dark environments. In general, each of the light arrays 231, 232 includes a radiant energy source 233, 234. In the embodiment of FIG. 2, each of the radiant energy sources 233, 234 includes a plurality (e.g., a line of 17) light emitting diodes (LEDs). Each of the light arrays 231, 232 also may include a power supply 235, 236 and a cooling fan 237, 238.

Figure 3A:
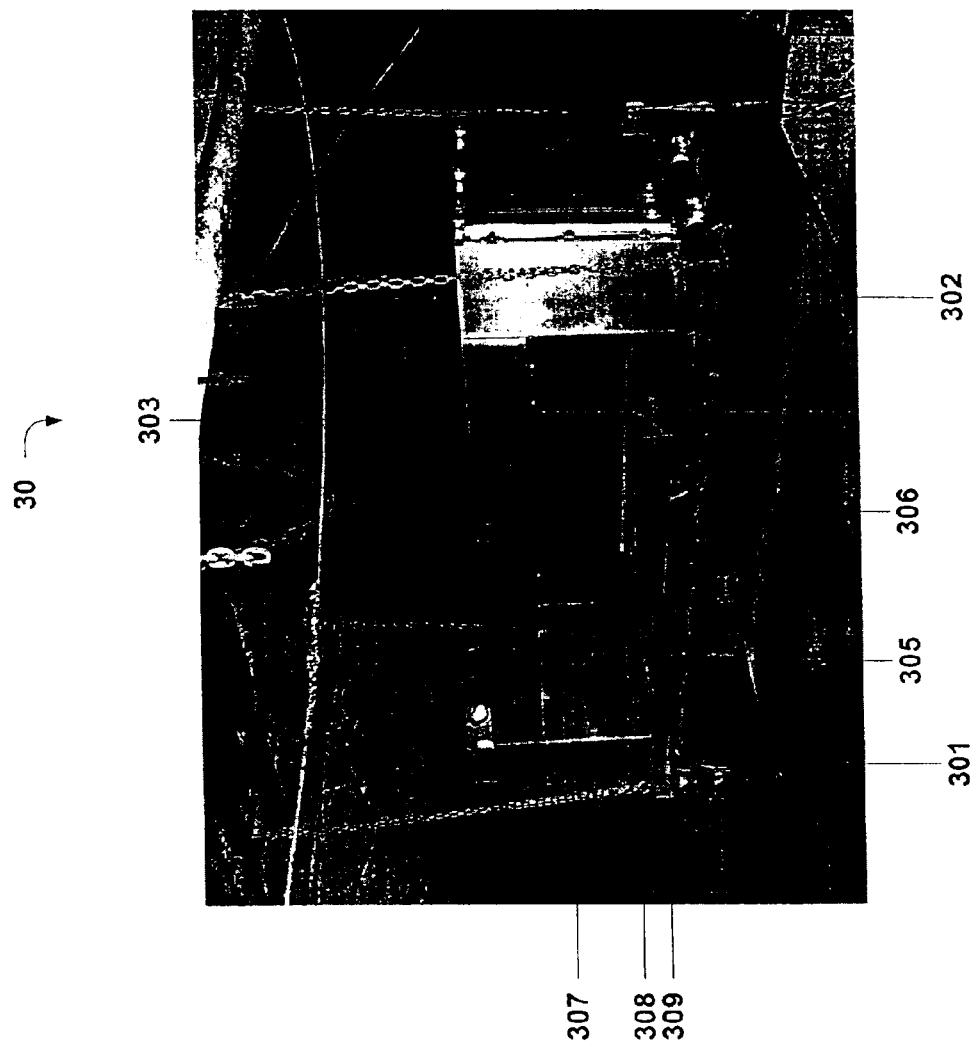
FIG. 3A illustrates one embodiment of a housing for a belt inspection system.

In some embodiments, a protective housing may be provided to protect one or more elements of the system. FIG. 3A illustrates one embodiment of a protective housing 30 that may be used to protect one or more elements of the BIS 20. The housing 30 may enclose one, some, or all of the components of the BIS 20.

As shown, the housing 30 includes a first end enclosure 301 which may contain computer elements such as, for example, the controller 200, the storage device 216, and the storage device power supply 217. The housing 30 includes a second end enclosure 302 which may contain the UI 218 and power distribution elements such as, for example, the power off relay 219, the UPS 220, the fan 221, the power distribution block 222, the fan 223, the power line filter 224, the power on relay 225, the power on switch 227, and the power indicator light 228. The end enclosures 301, 302 are connected by a first cross member 303 and second cross member (not shown), through which cabling is run and cooling air is circulated via fans 221, 223. The housing 30 further includes a first lower member 305 and a second lower member 306, which may contain elements of the first light array 231 and the second light array 232, respectively.

In one embodiment, the housing 30 may include chains 307 attached by bolts 308 at extending portions 309. The housing 30 may be mounted by wrapping each the chains 307 around the bed rail of the top belt then looping each of the chains 307 through one of the bolts 308 and attaching each of the chains 307 to a descending portion of itself. The length of the chains 307 may be adjusted to ensure the proper separation between the housing 30 and the monitored portion of the belt. In one implementation, the cameras should be set at about 29 inches from the belt, which puts the top of the housing 30 at about 36 inches from the belt. In the case of a panel belt where the belt may be angled and then flattens at the snub roller ahead of the stationary take-up pulley, the chains 307 may be adjusted to put the housing 30 perpendicular to the belt.

When utilized, the encoder 213 may be enclosed within the housing 30 or enclosed by a separate housing. There may be considerable variation site-to-site in encoder installation. On a panel belt, for example, the encoder typically is mounted on the snub roller ahead of the take-up but the mounting can vary depending on whether the roller is solid or hollow. In one embodiment, an encoder wheel may be used where there are no available rotating elements to which a standard encoder can be affixed to at installation site.

Figure 3B:
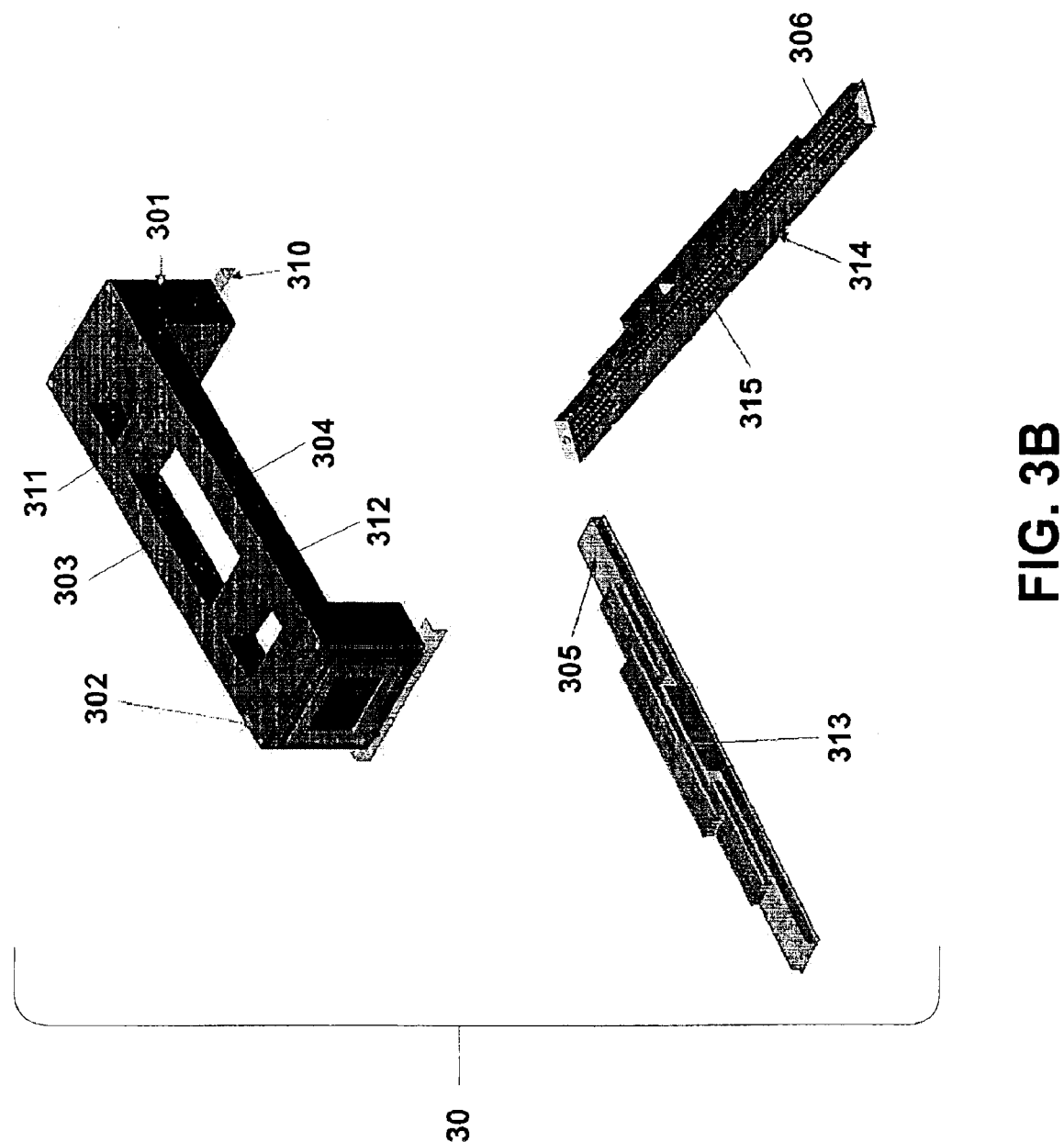
FIG. 3B illustrates one embodiment of a housing assembly for a belt inspection system.

FIG. 3B illustrates one embodiment of a housing 30 as an assembly. As shown, the end enclosures 301, 302 and the cross members 303, 304 may be implemented as one piece of the assembly including mounting brackets 310 for attaching the lower members 305, 306. Between the cross members 303, 304 are two additional members 311, 312 that run parallel to the long axis of the belt and may house the first camera 211 and the second camera 212, respectively. Each of the lower members 305, 306 includes a heat sink 313 and a cover 3142 for protecting the LEDs 315. The heat sink 311 improves lighting efficiency.

Although not shown, brattice cloth may be attached with ties on the outside of the housing 30 to prevent splashing of dirty water on the lights and cameras. When there is moisture the belt, such splashing can occur as the belt encounters the snub roller. In general, the glass cover protecting the camera lens from the mine environment should be checked and wiped cleaned on a regular basis (e.g., every week). In addition, each heat sink 311 and cover 312 should be checked and cleaned when dirty.

In one embodiment, the BIS 20 operates in tandem with and/or at the direction a program. Examples include, but are not limited to, a computer program, a software application, computer code, set of instructions, plug-in, applet, or combinations thereof, for independently or collectively instructing one or more computing devices to interact and operate as programmed. The program may be run, for example, by a controller 200, when implemented as a computer or a computer system.

Figure 4:
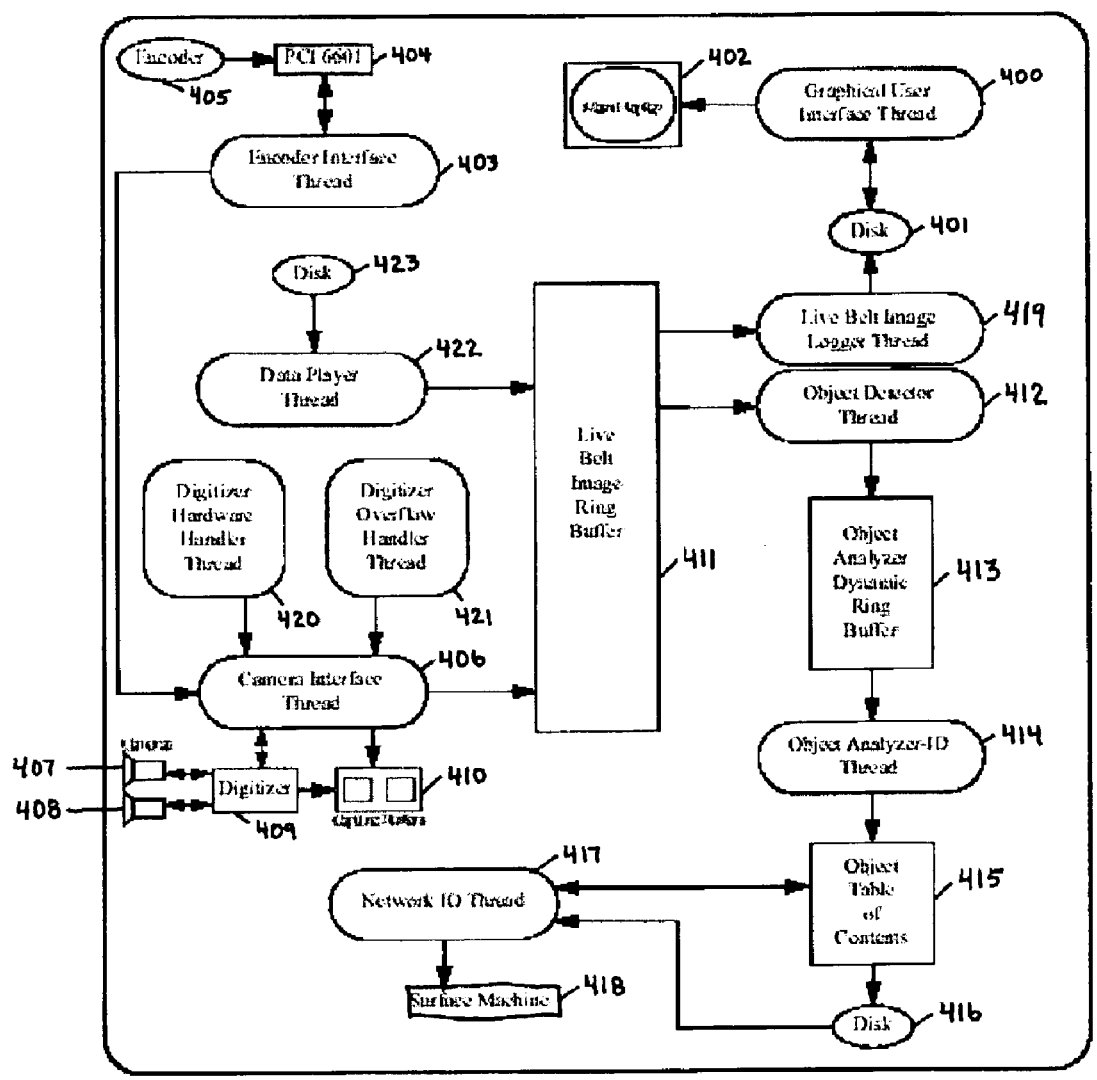
FIG. 4 illustrates one embodiment of a belt inspection system program.

FIG. 4 illustrates one embodiment of a program 40 that may be implemented by the BIS 20 to analyze detected conditions of a conveyor belt that may lead to future belt failure. As described in more detail below, the program 40 may include local (e.g., underground) elements for controlling cameras, collecting encoder data, capturing images, providing a user interface for belt inspection at the system installation point as well as remote (e.g., Web server) elements for collecting images captured by an underground unit, storing such images in a database, and distributing images to computers networked to a web server.

In general, the computer program 40 may utilize any suitable algorithms, computing language (e.g., Java, Perl, C or C++), and/or object-oriented techniques. The program 40 may be embodied permanently or temporarily in any type of computer, computer system, device, machine, component, physical or virtual equipment, storage medium, or propagated signal capable of delivering instructions. The program 40 when implemented as software or a computer program, for example, may be stored on a computer-readable medium (e.g., device, disk, or propagated signal) such that when a computer reads the medium, the functions described herein are performed.

As shown, the program 40 includes several components, with each component represented by its own thread. The graphical user interface thread 400 provides an intuitive user interface for displaying object image data and for viewing and configuring system parameters. The graphical user interface thread 400 may receive inputs including one or more data structures containing all system configuration and run-time parameters. The inputs to the graphical user interface thread 400 may be received from a disk 401, which may be implemented by the internal memory of the controller 200 and/or the storage device 216. The outputs of the graphical user interface thread 400 may be presented as a graphical display of system parameters and data on a main display 402. The main display 402 may be implemented, for example, by the UI 218 and/or by a remote display device.

The encoder interface thread 403 may be responsible for interfacing through an encoder controller card 404 to an encoder 405, computing current belt speed and position, computing desired digitizer line rate based on the current belt speed, and recording the belt speed—including monitoring the amount of time the belt is idle. The encoder interface thread 403 may receive inputs including number of encoder counts per meter from a user, time interval to compute belt speed over from a user, frequency to log belt motion statistics to disk from user, number of pixels per inch on the belt from user, and/or current encoder count from the encoder control card 404. The encoder interface thread 403 may output current belt speed, current belt position, and/or desired line rate obtained by multiplying the belt speed (inches/seconds) by the pixels per inch on the belt.

The camera interface thread 406 may be responsible for controlling one or more cameras 407, 408 via a digitizer card 409, stamping and loading captured image data from captured image buffers 410 into a live belt image ring buffer 411, and managing the live belt image ring buffer 411. The camera interface thread 406 may receive inputs including desired camera gain from the user, desired exposure time from a user, desired line rate from a user and/or from the encoder interface thread 403, and/or image alignment values from a user. As outputs, the camera interface thread 406 may set the desired camera gain, set the desired exposure time, set the desired line rate, and/or stamp received images from the digitizer 409 in the capture buffers 410 and copy them into the live belt image ring buffer 411.

The object detector thread 412 may be responsible for processing the live belt data contained in the live belt image ring buffer 411 in order to detect various objects on the belt, and for extracting and loading detected objects into the object analyzer dynamic ring buffer 413. The object detector thread 412 may receive inputs including a pointer to unprocessed live belt image data contained in the live belt image ring buffer 411. Outputs from the object detector thread 412 may include detected objects into the object analyzer dynamic ring buffer 413.

The object analyzer-ID thread 414 may be responsible for analyzing the objects in the object analyzer dynamic ring buffer 413 and for adding analyzed objects to an object table of contents 415. The object analyzer-ID thread 414 may receive inputs including detected object image and location. Outputs from the object analyzer-ID thread 414 may include analysis results and/or addition of objects to the object table of contents 415. In some cases, an identification number is assigned to objects and object image, stamp and analysis information is stored on a disk 416.

The network IO thread 417 may be responsible for communicating the state of the system to a surface machine 418. The surface machine 418 may be implemented, for example, as a web application server. The network IO thread 417 may receive inputs including detected object images, belt speed and length, state of object belt pattern, and/or pattern list of objects on belt with respect to point-of-origin. Outputs from the network IO thread 417 may include general status information such as current belt speed and length and periodical state of object pattern, compressed object image data (e.g., JPEG format) after each object is detected, and/or pattern list of objects on belt with respect to point-of-origin after each belt revolution.

The live belt image logger thread 419 may be responsible for stamping and logging all captured live belt image data to the disk 401. The live belt image logger thread 419 may receive inputs including live belt image data and stamp information from the live belt image buffer 411. Outputs from the live belt image logger thread 419 may include live belt image data and stamp information to the disk 401.

The digitizer hardware handler thread 420 may be responsible for determining when a hardware exception handler error occurs and for resetting the capturing of image data upon detection of an error. The digitizer hardware handler thread 420 may receive inputs including a hardware exception signal error from the digitizer card 409. Outputs from the digitizer hardware handler thread 420 may reset a digitizer flag to be true.

The digitizer overflow handler thread 421 may be responsible for determining when an overflow exception handler error occurs and for resetting the capturing of image data upon detection of such an error. The digitizer overflow handler thread 421 may receive inputs including an overflow exception signal error from the digitizer card 409. Outputs from the digitizer overflow handler thread 421 may reset a digitizer flag to be true.

The data player thread 422 may be responsible for playing back previously recorded live belt data stored on a disk 423. The data player thread 422 may receive inputs including base directory where live belt images are stored and/or start and stop image index to play back through the system. Outputs from the data player thread 422 may load image data and stamp information into the live belt image ring buffer 411 and set belt speed, length, and position based on information contained in the header of the live belt image.

In one implementation, the BIS system 20 may operate in one of two modes. Namely, a live data mode where live image data from the cameras are captured and processed by the system or play back data mode where previously logged images are read from disk and processed by the system. The flow of data throughout the BIS system 20 when in one of these modes is described below with reference to FIG. 4.

In the live data mode, the BIS 20 captures and processes live imagery captured from the cameras 407, 408. In one implementation, the active threads in the live data mode include the graphical user interface thread 400, the encoder interface thread 403, the live belt image logger thread 419, the object detector thread 412, the object analyzer-ID thread 414, the network IO thread 417, the camera interface thread 406, the digitizer hardware handler thread 420, and the digitizer overflow handler thread 421. In this implementation, the graphical user interface thread 400 is the first thread started and reads in (from disk 401) and sets all system configuration settings, and allocates and initializes all data structures for the entire system. The graphical user interface thread 400 then launches each of the other active threads in the system.

The encoder interface thread 403 controls the main flow of data from this point. The encoder interface thread 403 periodically reads the current encoder count contained on the encoder controller card 404 and uses this information to update the position and speed of the belt. Based on the current speed of the belt and the camera pixel resolution, the encoder interface thread 403 computes and sets the desired camera digitizing line rate.

The camera interface thread 406 is continuously capturing data from the cameras at the highest line rate the system will ever require, based on the highest belt speed that the system will experience. The two capture buffers 410 are configurable in the number of lines of image data that each can hold (e.g., set to 512). The digitizer card 409 uses these capture buffers 410 in an alternating fashion where it copies new captured image data into one of the buffers until it is full, notifies the camera interface thread 406 that new image data is ready to process in that buffer, and then continues to copy new image data into the next capture buffer. When the next capture buffer is full, the digitizer 409 notifies the camera interface thread 406 that data is ready to be processed in that buffer and continues to copy new image data again in the first buffer and so on.

Each time the camera interface thread 406 is notified that there is new data to process, it copies the appropriate new image lines, which are determined by knowing the current and desired digitizing line rate, into the live belt image ring buffer 411. Each time a new image line is copied over to the live belt image ring buffer 411, the camera interface thread 406 stamps the data with various information on the state of the system when the image was captured (e.g., belt speed and position, digitizing rate, camera gain, exposure time, etc.) and updates pointers to the latest/current image data. Other threads in the system use this pointer to determine what data is new and has not been processed yet.

When the live belt image logger thread 419 is enabled, it periodically checks to see if new data exists in the live belt image ring buffer 411. If new data is found, the live belt image logger thread 419 logs the new image data to disk 401 along with its image stamp information of the belt and camera settings when the new image data was captured.

The digitizer hardware handler thread 420 monitors hardware exception errors that the digitizer card 409 reports to the application when they occur. Every time a hardware exception signal is received by the digitizer hardware handler thread 420, it sets a flag that informs the camera interface thread 406 to reset (stop and restart) digitizing in order to insure correct synchronization with the data coming from both cameras 407, 408.

The digitizer overflow handler thread 421 monitors overflow errors that the digitizer card 409 reports to the application when they occur. These typically occur when there is too much activity on the PCI bus and the digitizer 409 could not deliver all of the image data to the capture buffers 410, which may reside in local computer memory space. Every time an overflow exception signal is received by the digitizer overflow handler thread 421, it sets a flag that informs the camera interface thread 406 to reset (stop and restart) digitizing in order to insure correct synchronization with the data coming from both cameras 407, 408.

The object detector thread 412 watches the live belt image ring buffer 411 looking for new image data to arrive. When it does, the object detector thread 412 runs one or more object detection algorithms on the data to determine whether or not an object is present in the image data. Every time an object is detected, image data and stamp information is extracted from the live belt image ring buffer 411 and placed in the object analyzer dynamic ring buffer 413 along with the type of object that is contained in the image.

The object analyzer-ID thread 414 processes objects that are contained in the object analyzer dynamic ring buffer 413 in a first-in-first-out (FIFO) manner. Each analysis algorithm that is run on the object image is determined by the type of object contained in the object analyzer dynamic ring buffer 413. After the object has been analyzed, it is added to the object table of contents 415.

The object table of contents 415 stores and manages a fixed size list of objects that have been detected by the system. In addition, the object table of contents 415 manages the identification of object IDs. When a request is made to add a new object, the object table of contents 415 first determines the proper ID to assign to the object. It then logs the object image to disk 416 along with the image stamp, object ID, and object analysis results. A record of where the object is stored on the disk 416, object ID, the image stamp and object analysis results are stored within the object table of contents 415 so that the object image can be retrieved for display at a later time.

The network IO thread 417 is in charge of sending all system information from the BIS 20 to the surface server machine for display and storage. One message that is sent may contain the image data of an object and its analysis results. The network IO thread 417 monitors the object table of contents 415 and sends out this message every time a new object is added to the object table of contents 415. Another message that is sent may contain information on the current length of the belt, the current number of objects on the belt, and the pattern in which those objects occur all of which have been determined by the BIS 20. The pattern is with respect to the point-of-origin on the belt which can be either the first object detected by the BIS 20 or by detecting an actual fiduciary point-of-origin that has been placed on the belt. This message may be sent out once per revolution of the belt. Another message is a general status message which contains information on whether or not the current object pattern on the belt is known, and the current speed and position of the belt. This message may be sent out periodically.

The graphical user interface thread 400 periodically may update the display 402 with the latest system information. In one implementation, the main piece of data that is updated is the object display window which displays the detected object image and various information about the object. How the window is updated depends on what mode of updating the system is in, which can be either manual, current, or loop. In manual mode, the object display window only gets updated when the user clicks on the go to next or previous object buttons. In current mode, the graphical user interface thread 400 always updates the display with the most recent object detected by the system. In loop mode, the graphical user interface thread 400 periodically loops over a configurable amount of objects that have been detected by the system.

In play back data mode, the BIS 20 uses previously captured and logged image data from the cameras 407, 408 contained on disk as input to the system to process. In one implementation, the active threads in play back data mode include the graphical user interface thread 400, the live belt image logger thread 419, the object detector thread 412, the object analyzer-ID thread 414, the network IO thread 417, and the data player thread 422.

The flow of data in play back mode is nearly identical to that of the live data mode, described above. In play back mode, the data player thread 422 acts as a simulator for the entire system. Namely, the data player thread 422 is given a base directory location of where the previously logged live belt images are stored and a range of image values to loop over. The data player thread 422 reads in the live belt images from disk 423 one image at a time. As a result of reading in the image, the data player thread 422 has a buffer containing the live belt image and the image stamp information which was stored in the image header located on the disk 423.

Each time the data player thread 422 reads in a new image, it loads the image data into the live belt image ring buffer 411 and stamps the image data with the stamp stored in the image header. This simulates the camera interface thread 406 receiving data from the digitizer 409 and copying the data from the capture buffers 410 into the live belt image ring buffer 411. The belt speed, position, length and other system variables are also updated by the data player thread 422 with the information that was stored in the image header. This simulates the encoder interface thread 403 computing this information. Aside from these differences, the rest of the data flow in the system continues in substantially the same manner as in the live data mode scenario above.

Figure 5:
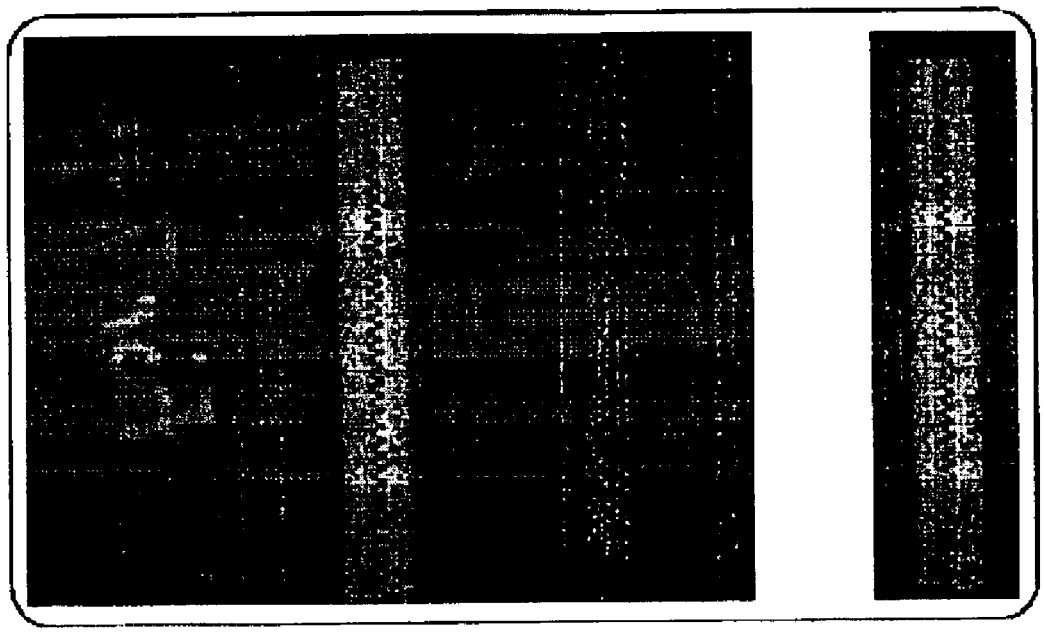
FIG. 5 illustrates one embodiment of an example of raw image data and extracted mechanical splice image data.

In one embodiment, the BIS 20 may be configured to perform mechanical splice detection and analysis. In general, mechanical splice detection deals with the identification of mechanical splices as live imagery is collected. Mechanical splice detection may include monitoring all raw image data and extracting only those sections of imagery that contain a mechanical splice. FIG. 5 illustrates an example of raw image data shown on the left and extracted mechanical splice image data shown on the right.

The BIS 20 may utilize several mechanical splice detection algorithms. Each algorithm may look for a unique feature that only occurs in mechanical splices. In one implementation, the underlying goal of each algorithm is to find a score for each line of pixels in the raw image data that was produced by the camera. By examining these scores, the algorithm determines where a mechanical splice is located and marks it as a mechanical splice. That section of imagery is then extracted and placed into the object analyzer dynamic ring buffer 413 where it will be analyzed for defects.

One embodiment of a mechanical splice detection algorithm may include detection based on edge information. Since the belt is continuously running along rollers in the mine, the belt develops stripes that run lengthwise, i.e. the vertical direction, along the belt. By running an edge filter that strictly looks for edges that are perpendicular to the direction of travel of the belt, the splice is distinct from the background.

Figure 6:
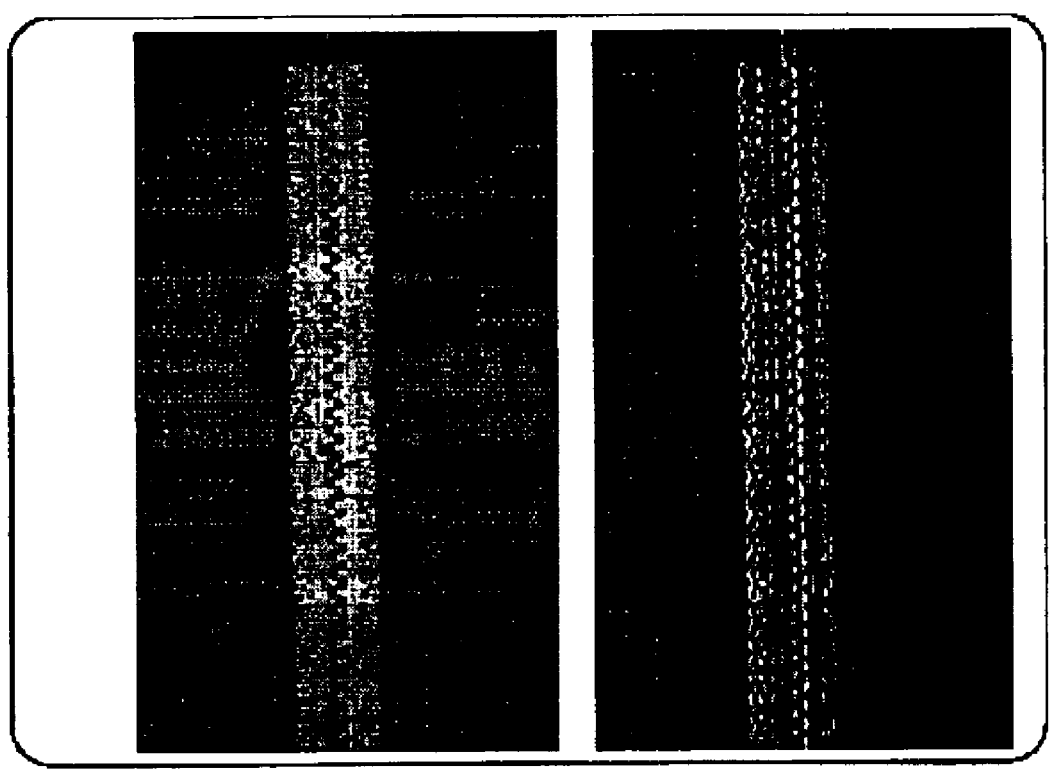
FIG. 6 illustrates one embodiment of a raw belt image and edge intensity image.

In one implementation, edge detection is performed by creating an edge intensity image. The edge intensity image may be created by taking one row of image data and subtracting another row of image data from it. The rows being used can be adjacent or separated by some configurable gap value depending on the lenses and the camera configuration used. FIG. 6 illustrates a raw belt image on the left and an edge intensity image on the right.

Figure 7:
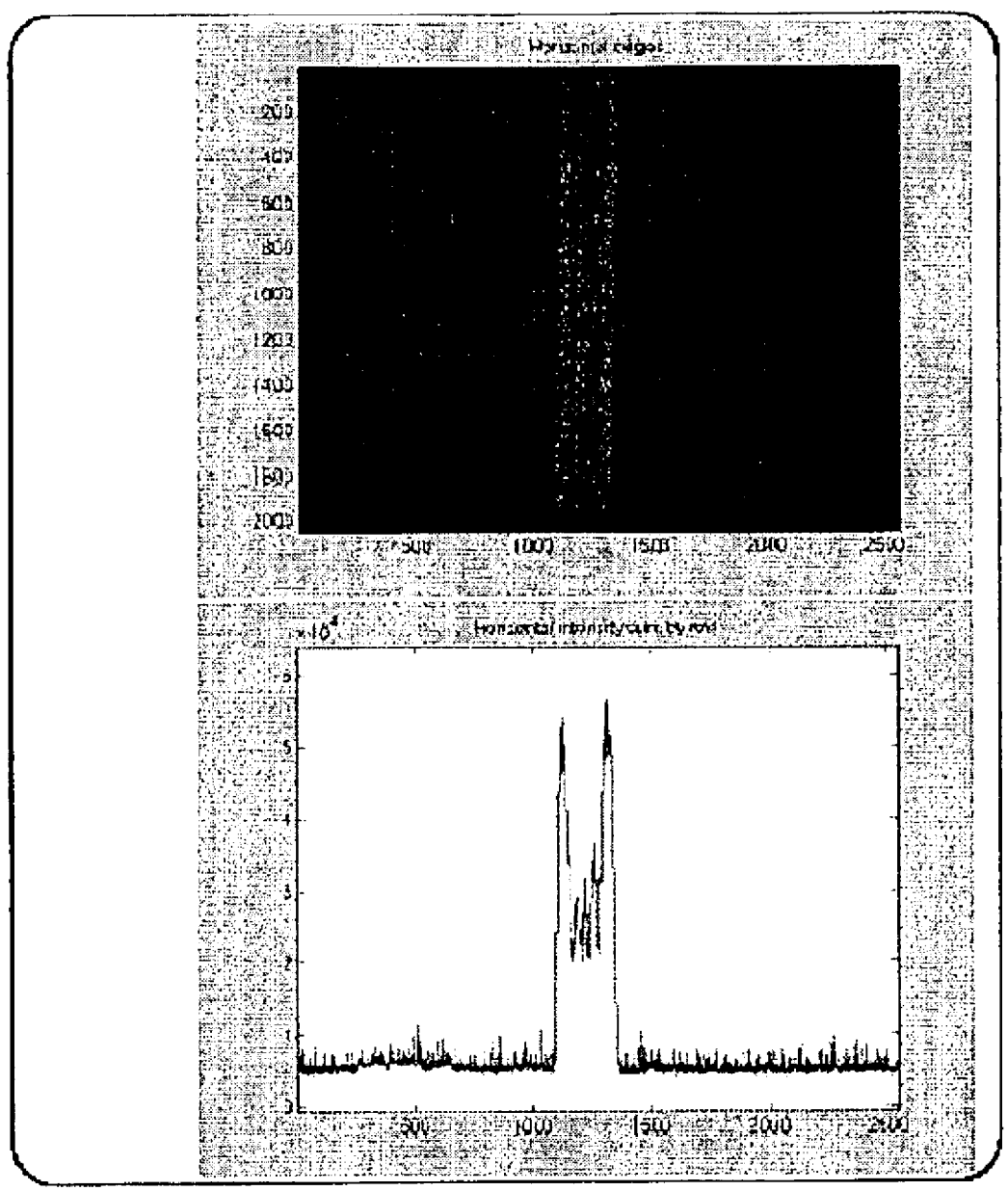
FIG. 7 illustrates one embodiment of an edge image and row scores.
Figure 8:
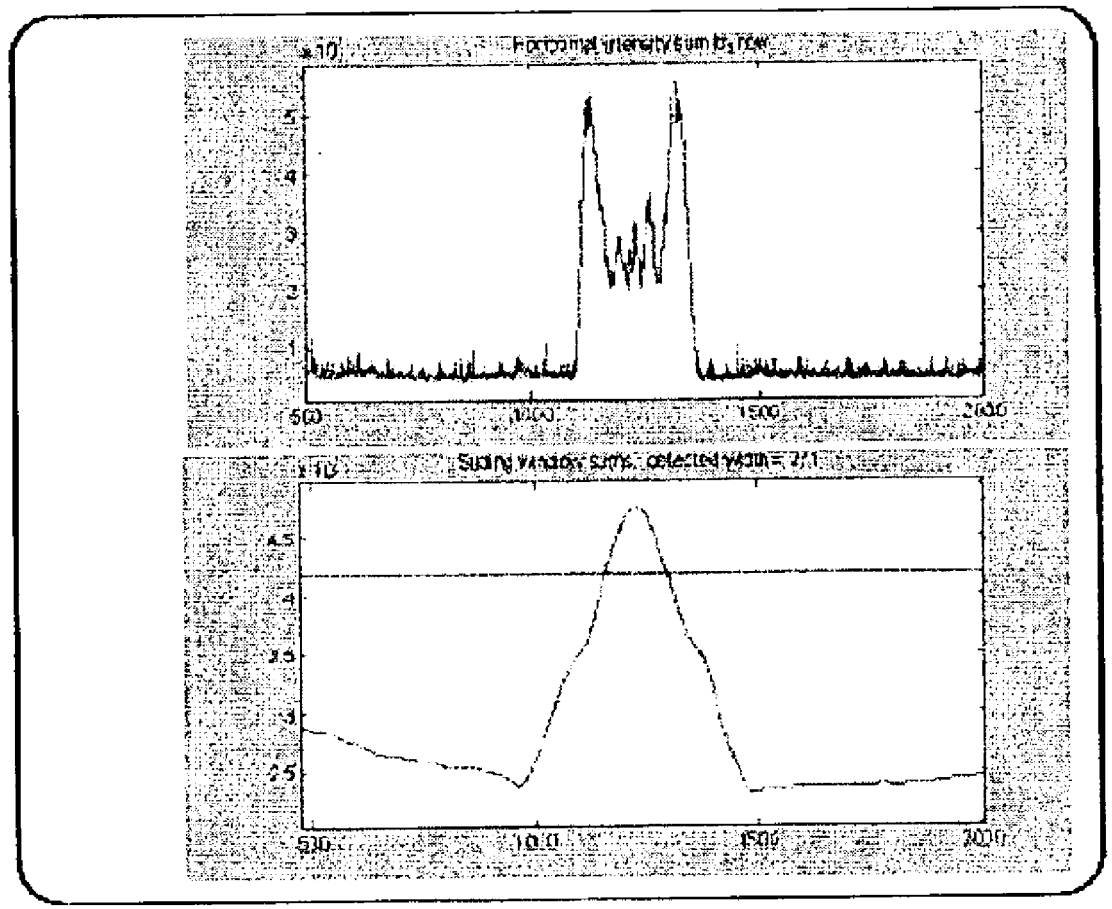
FIG. 8 illustrates one embodiment of edge row sums and running window sum.

Next, a score can be obtained for each row of pixels by summing up the edge intensities. FIG. 7 illustrates an edge image (above) and row scores (below). The row scores can then be added into a running window sum for each row. When the running window sum reaches its maximum value, the window is centered on the splice and a detection has occurred. Any maximums that occur above a certain threshold are considered splices in the imagery. FIG. 8 illustrates edge row sums (top) and running window sum with detection threshold (bottom).

Figure 9:
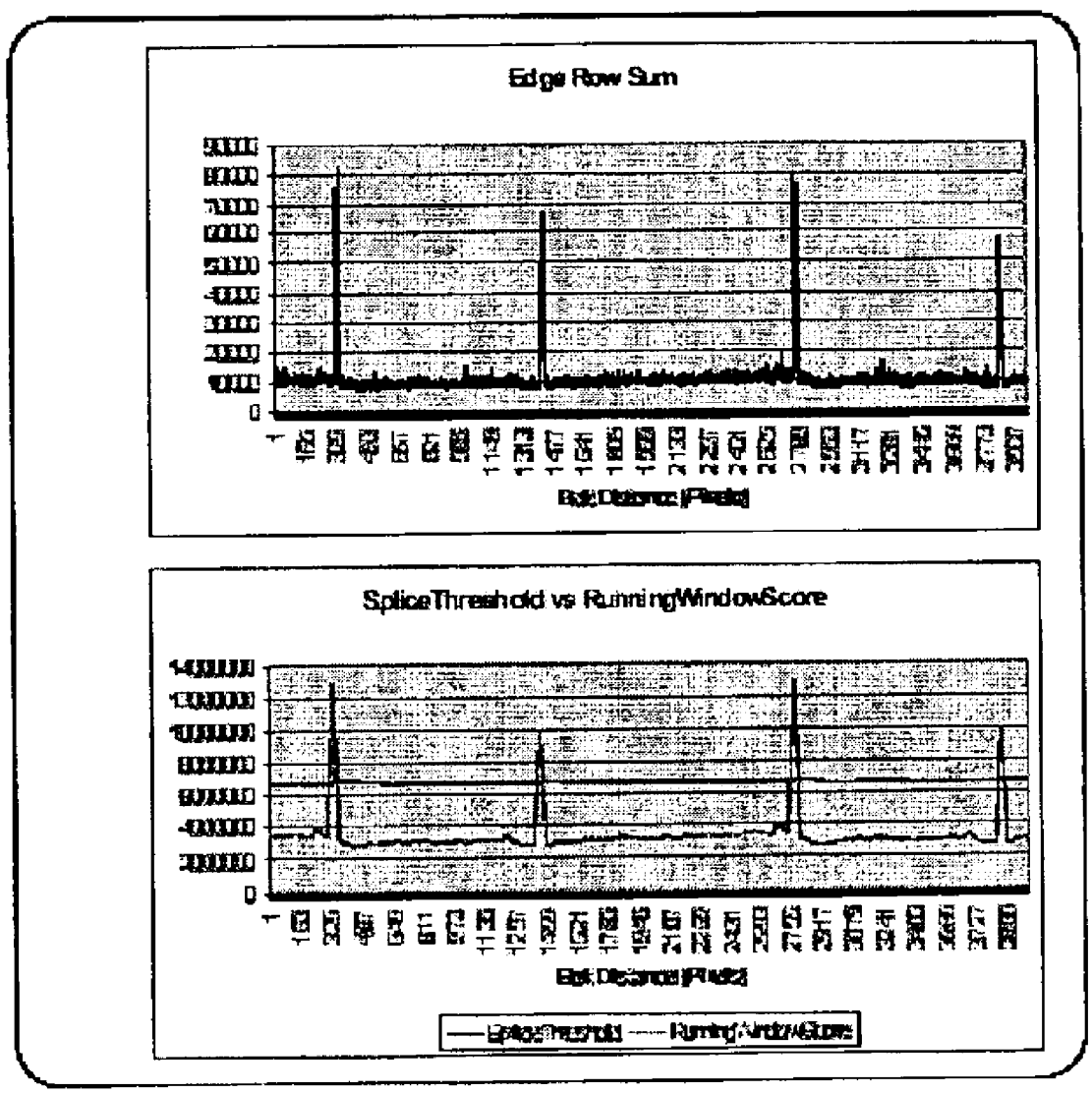
FIG. 9 illustrates one embodiment of row scores, running window sums and threshold.

The threshold used for detection can be calculated dynamically for changing lighting and belt situations. For example, keeping a running average of scores, the threshold may be chosen to stay above the running average by about fifty percent (50%). By examining the number of rows that fall above the threshold (in one group), some false positive situations may be eliminated. Detected features that do not have the correct width (which is the size of the mechanical splice in pixels) can be discarded as false detection. This may occur when the running window sum is noisy and may cross the threshold line a few times while climbing or falling a peak. FIG. 9 illustrates results of the algorithm running on a test rig with two splices on a 35-foot piece of belt in a continuous loop. In the figure, row scores are shown above and running window sums and thresholds are shown below.

Figure 10:
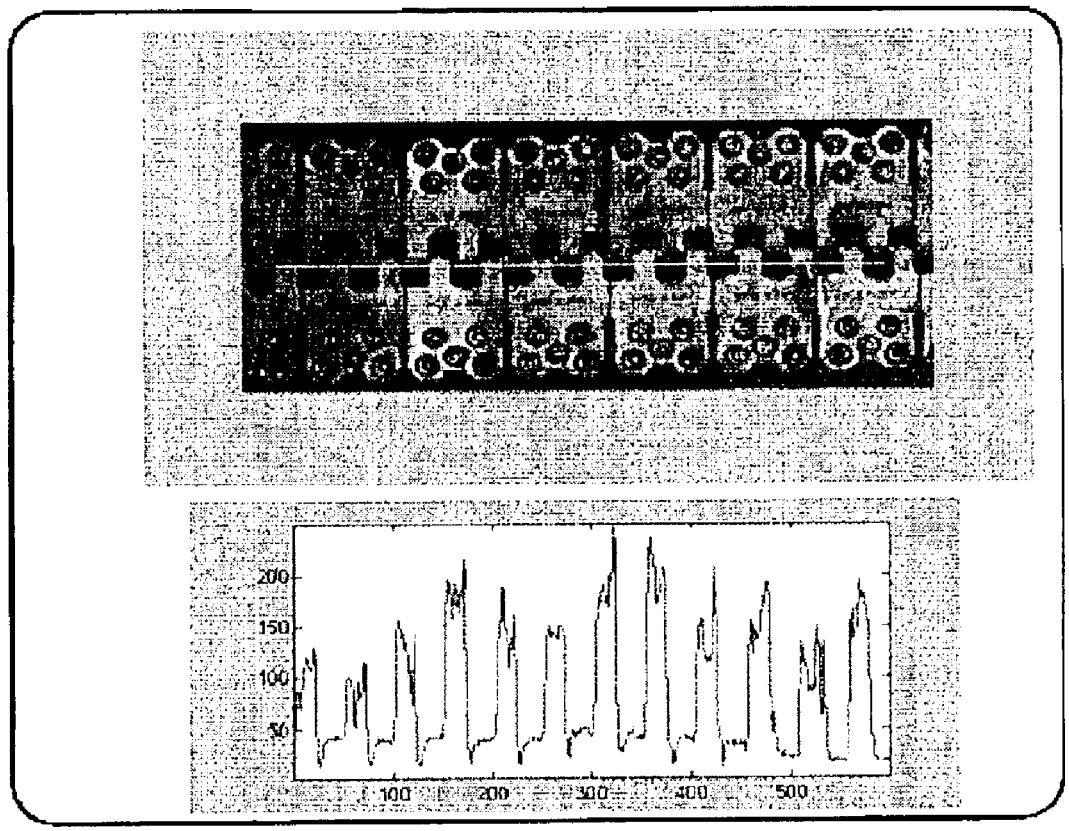
FIG. 10 illustrates one embodiment of a raw mechanical splice image and intensities.

Another embodiment of the mechanical splice detection algorithm may include comb splice detection. One distinguishing feature that a mechanical splice has is the zipper of holes that appears at the center of the splice. This is a very specific pattern that does not naturally occur on the belt, making it useful for splice detection. FIG. 10 illustrates raw mechanical splice image (top) and intensities along the zipper highlighted in the top image (bottom). Given the shape of the zipper intensities along a row (appearing as the teeth of a comb), high scores are obtained when this regular pattern is observed.

Figure 11:
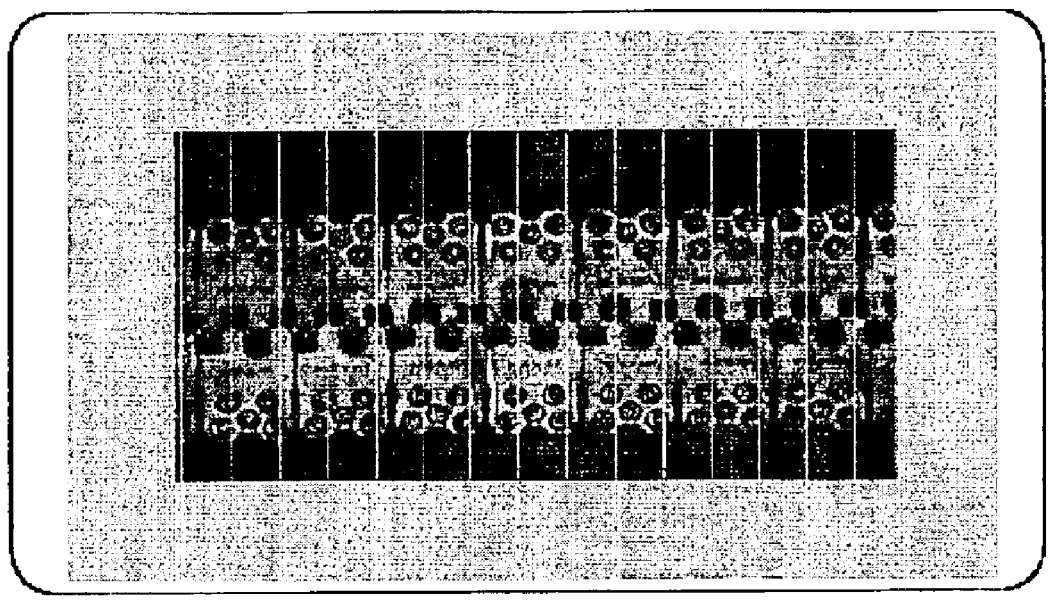
FIG. 11 illustrates one embodiment of column spacing for comb sums.

It is important to note that splices will not always be exactly orthogonal in the image. In this case, the zipper appears at an angle in the image. The complete row score may be obtained by splitting the image into zones, looking for zippers in the rows contained in each zone and adding zone scores. By using more zones, this system can tolerate splices that are more off-angle. For each zone (e.g., eight zones of 512 pixels each), comb sums are created which represent the sum of pixel intensities of each column in a specific pattern. The goal is to match the pattern exactly with the spacing expected in the zipper. FIG. 11 illustrates column spacing for comb sums.

Figure 12:
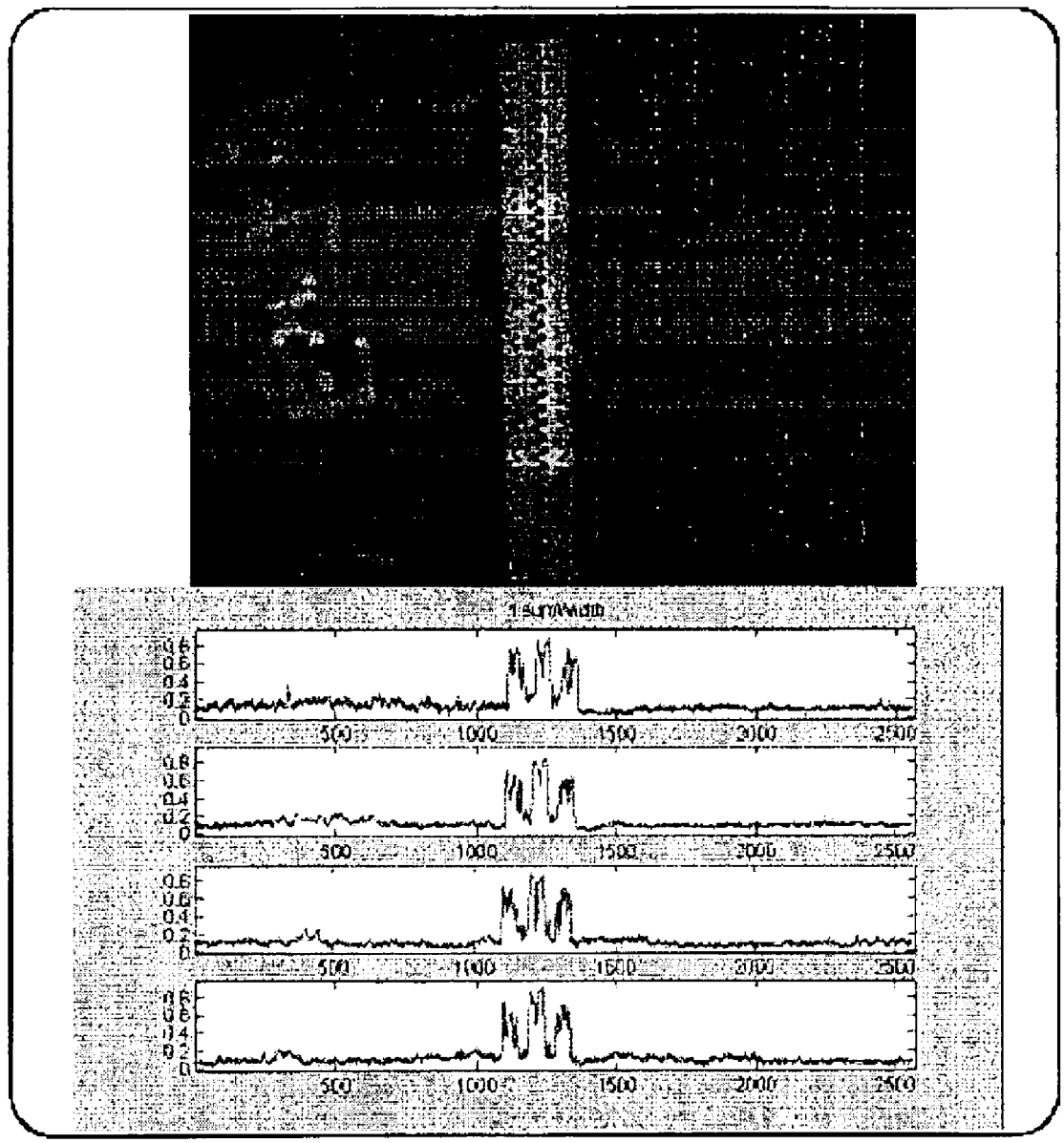
FIG. 12 illustrates one embodiment of a raw image and zone scores.

The algorithm then takes the minimum and maximum sum obtained for each row in each zone and calculates a ratio of minimum to maximum. FIG. 12 illustrates the raw image top and zone scores for four zones per row (bottom). It should be noted that the ratio score also may be triggered on belt rivets as they appear similar to the zipper patterns of splices.

Figure 13:
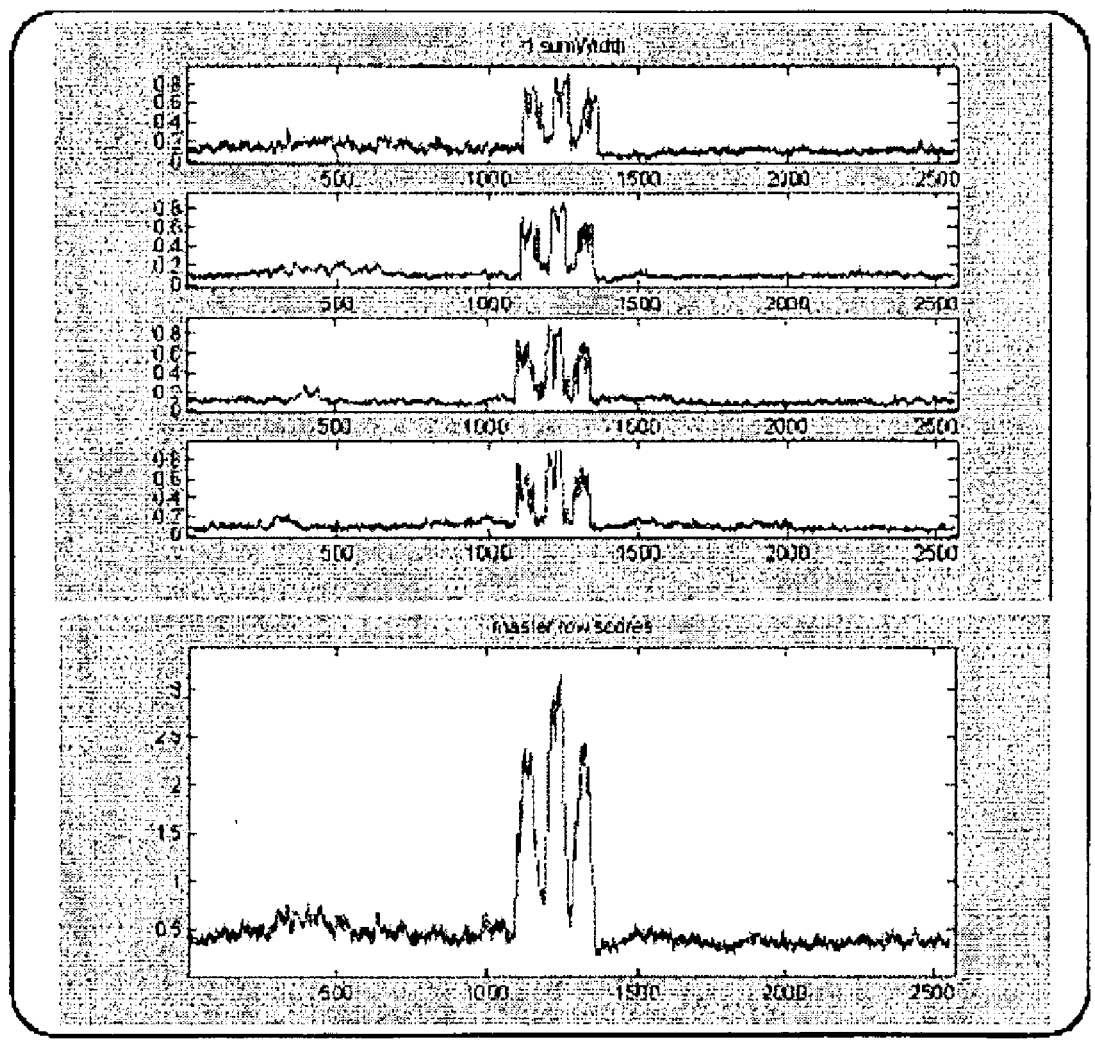
FIG. 13 illustrates one embodiment of zone scores.
Figure 14:
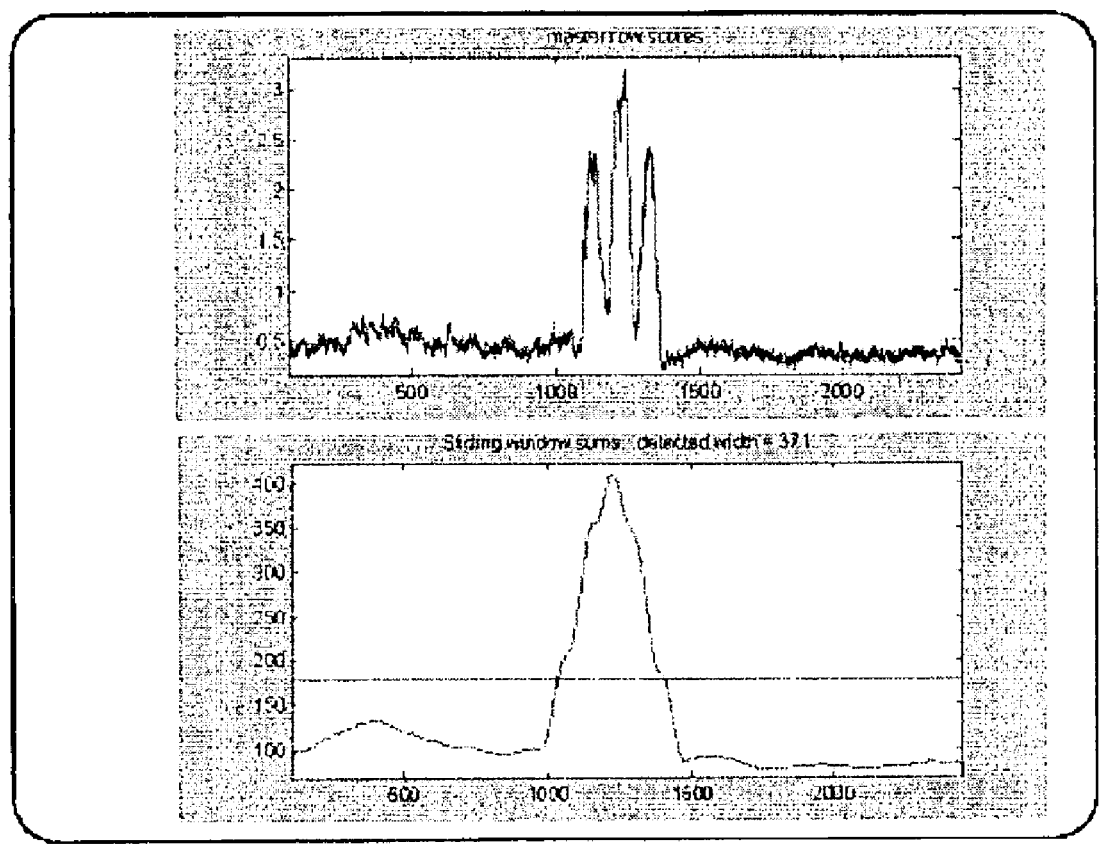
FIG. 14 illustrates one embodiment of row comb scores and running window sum.

Taking the best score (or ratio), from each zone in a row, the row score may be the sum of each zone score. FIG. 13 illustrates zone scores for four zones per row (top) and row scores (bottom). These row scores can be added into a running window sum for each row. When the running window sum reaches its maximum value, the window is centered on the splice and a detection has occurred. Any maximum that occurs above a certain threshold is considered a splice in the imagery. FIG. 14 illustrates row comb scores (top) and running window sum with detection threshold (bottom).

Figure 15:
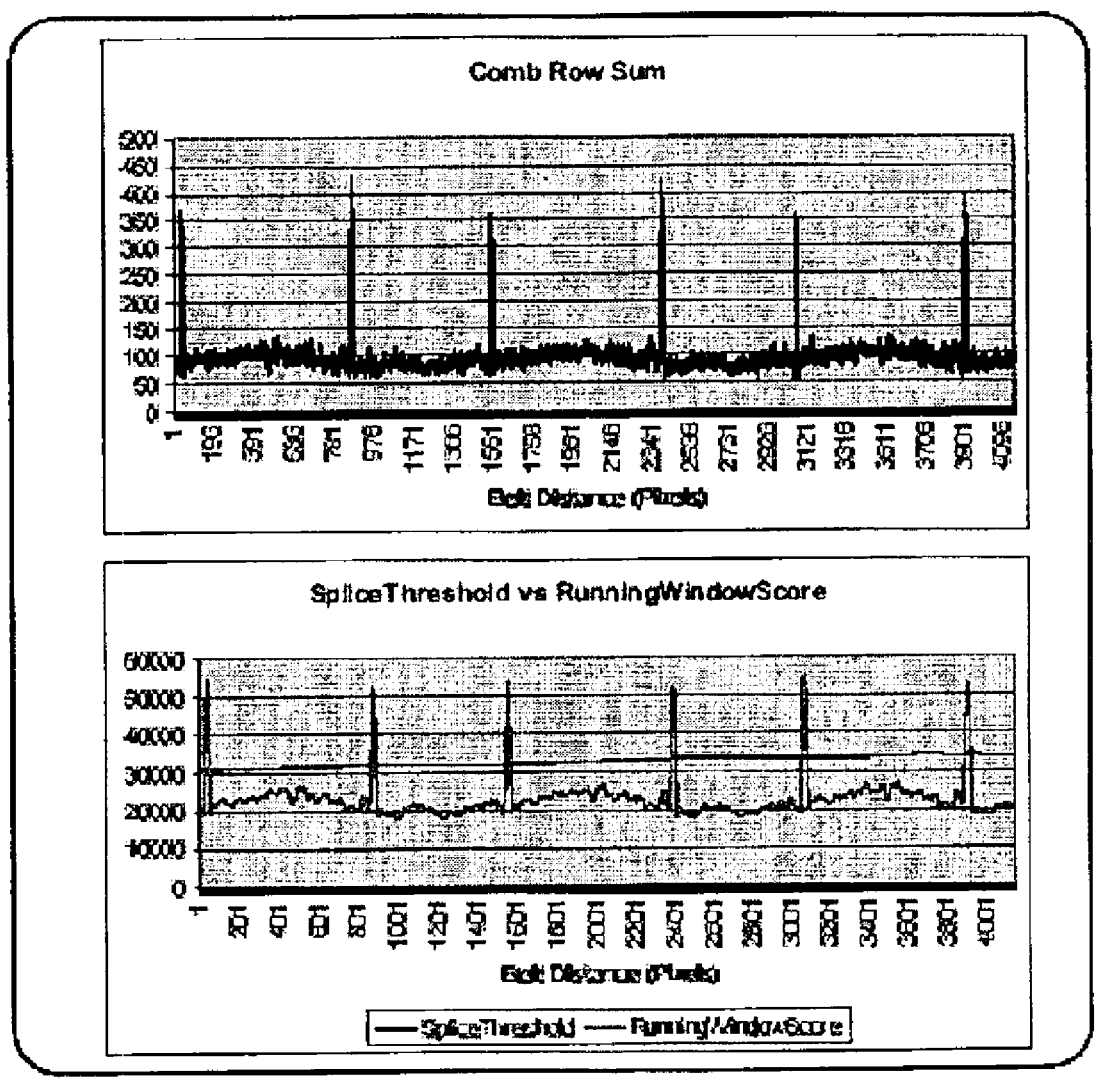
FIG. 15 illustrates one embodiment of row scores, running window sums and threshold.

Again, the threshold used for detection may be calculated dynamically for changing lighting and belt situations. For example, keeping a running average of scores, the threshold may be chosen to stay above the running average by about fifty percent (50%). By examining the number of rows that fall above this threshold (in one group), some false positive situations may be eliminated. Detected features that do not have the correct width (which is the size of the mechanical splice in pixels) can be discarded as false detection. This may occur when the running window sum is noisy and may cross the threshold line a few times while climbing or falling a peak. FIG. 15 illustrates results of the algorithm running on a test rig with two splices on a 35-foot piece of belt in a continuous loop. In the figure, row scores are shown at the top and running window sums and threshold are shown at the bottom.

Another embodiment of a mechanical splice detection algorithm may include piano key splice detection. An analogy may be drawn between the belt images and a player piano roller with holes that trigger notes from the piano. The raw imagery coming from the belt can be thought of as the player roller with intensity levels representing the holes. As a mechanical splice comes past the detector, an event is triggered which registers a higher score (that can be used later to detect a splice).

Figure 16:
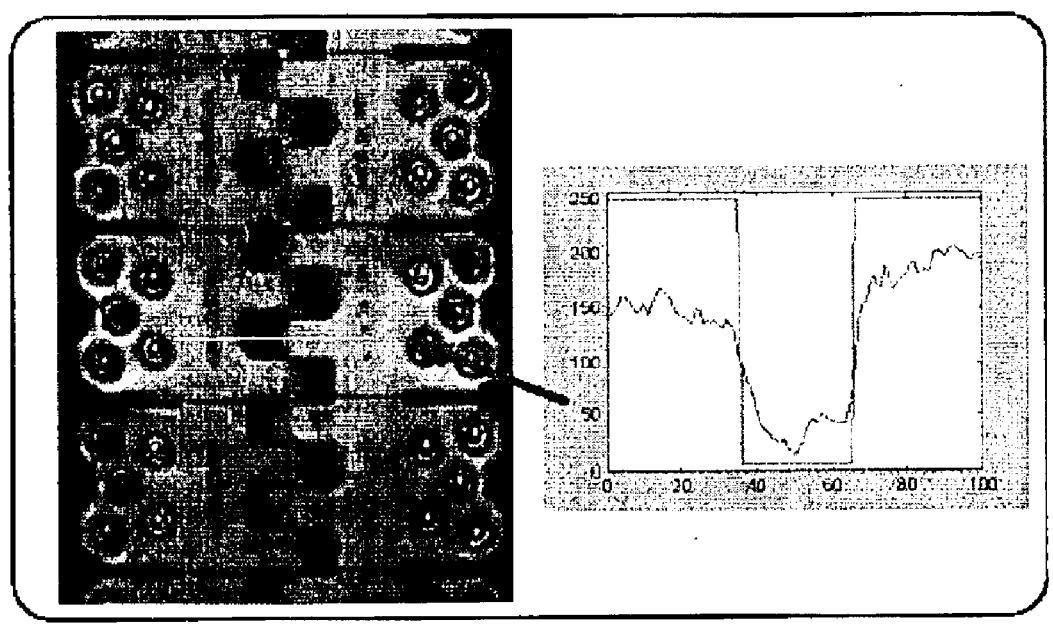
FIG. 16 illustrates one embodiment of a raw image and pixel values.

By looking at a specific sweep of pixels in a mechanical splice, a unique shape that only occurs at the holes of splices may be identified. FIG. 16 illustrates raw image (left) and pixel values with template pattern (right). As shown, the hole pattern fits the template pattern fairly well and will score highly.

Figure 17:
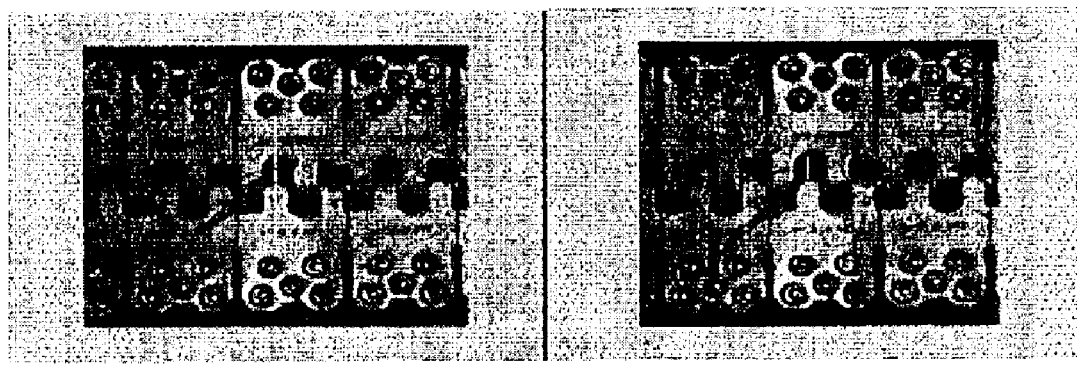
FIG. 17 illustrates one embodiment of a pattern sum and hold sum.

For each pixel, it is necessary to know the sum of intensities of two different windows around that pixel. These values may be referred to as the pattern running sum and the whole running sum. FIG. 17 illustrates pattern sum (left) and hole sum (right). The hole sum represents the pixels that will be very low if lined up on a hole. The pattern sum (subtracting out the hole sum) represents the rest of the pixels in the pattern which will score highly on clips where the pixel intensities are relatively high compared to the belt. It should be noted that unlike the previous mechanical splice detection algorithms, this algorithm examines the image data in the vertical (along the motion of travel of the belt) direction and thus this running sum must be maintained along the vertical direction.

Figure 18:
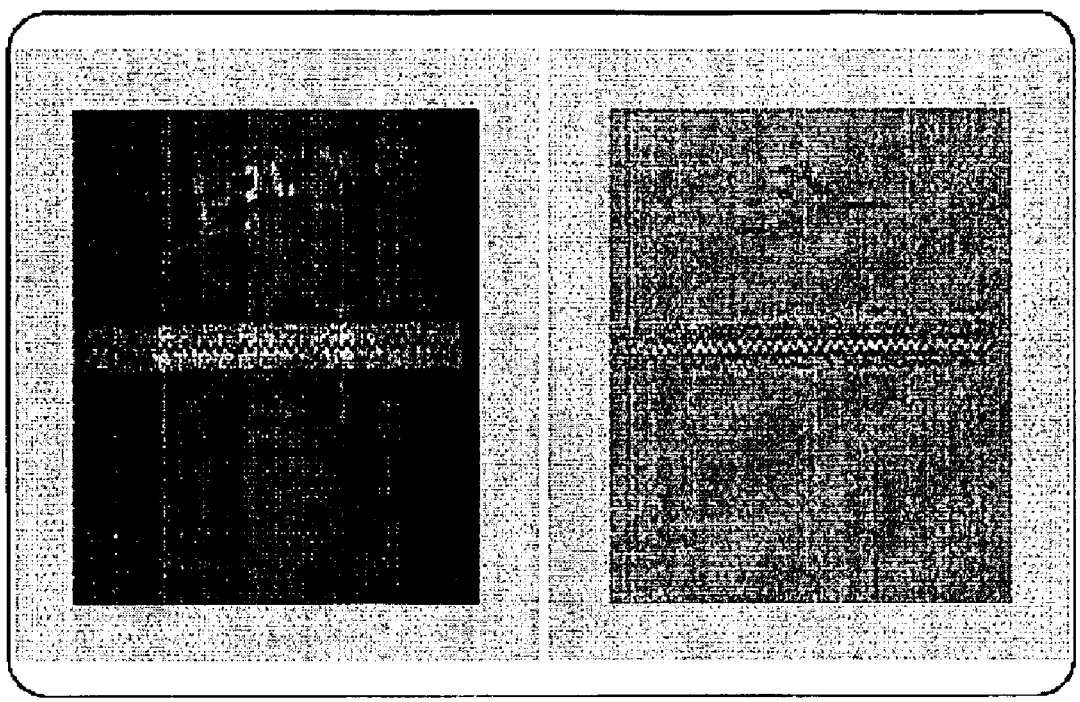
FIG. 18 illustrates one embodiment of a raw image and pixel scores.
Figure 19:
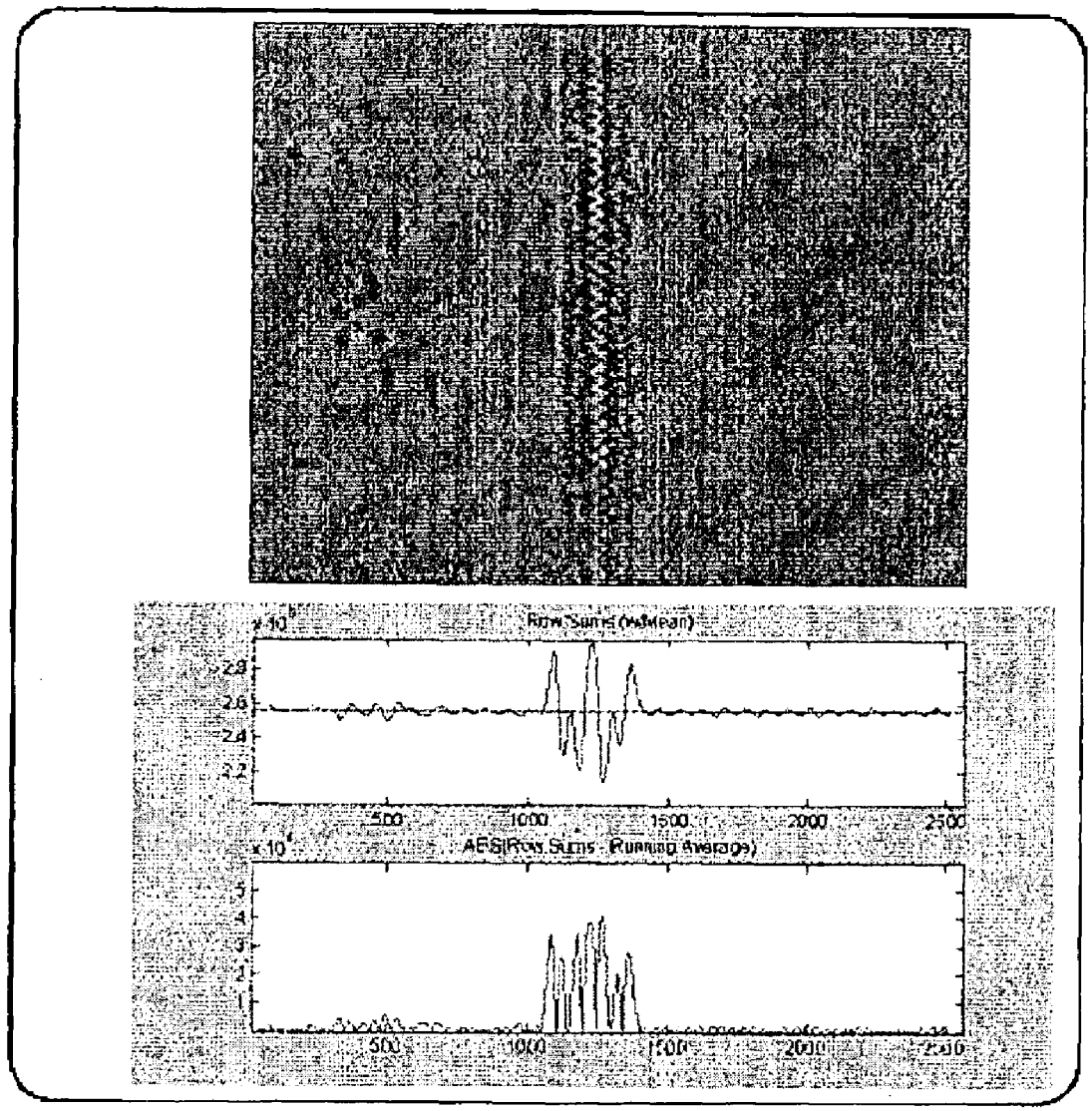
FIG. 19 illustrates one embodiment of pixel scores, row sums and final row scores.
Figure 20:
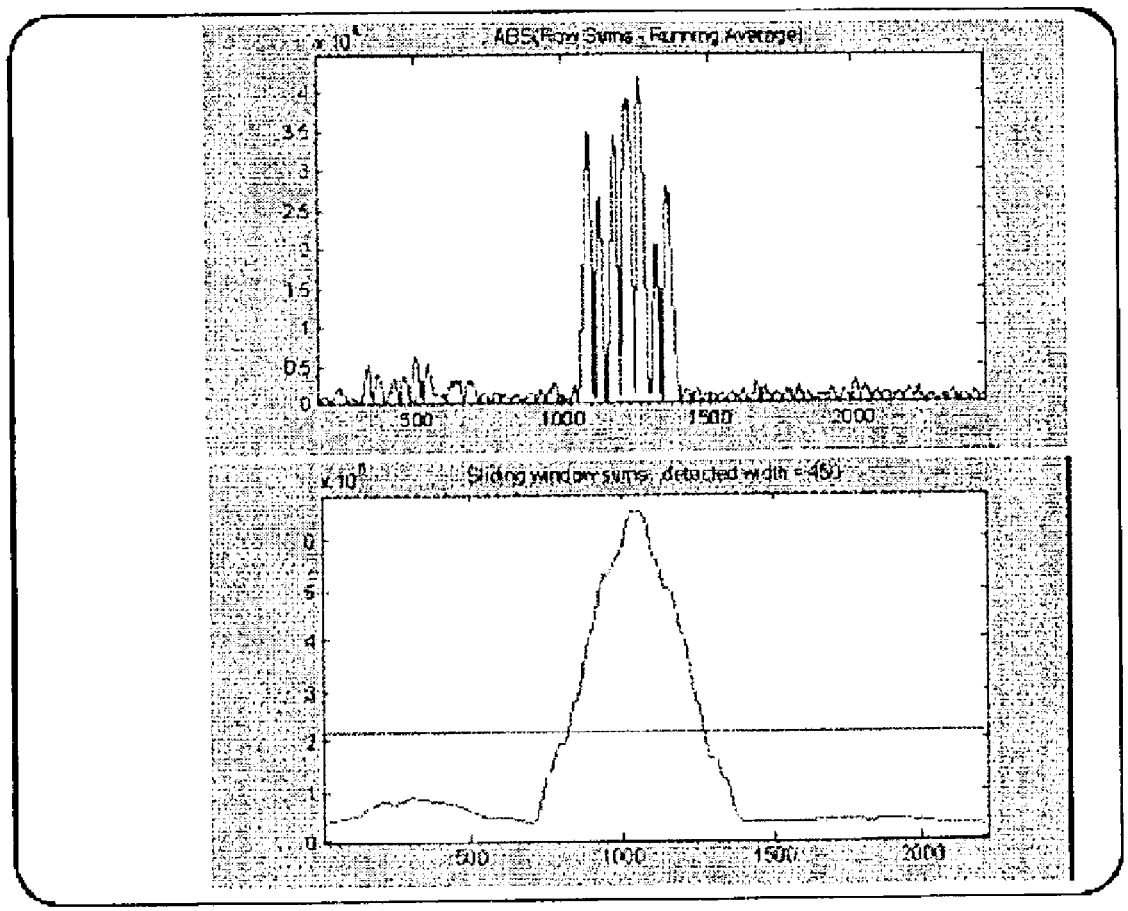
FIG. 20 illustrates one embodiment of row scores and running window sum.

Using the running sums, pixel scores can be calculated indicating how well each pixel fits the pattern. FIG. 18 illustrates raw image (left) and pixel scores (right). As shown, lighter corresponds to a better fit. In one implementation, pixel scores can be calculated using the following formula:

$$\text{Pixel Score} = \frac{S_p - S_h}{N_p - N_h} - \frac{S_h}{N_h}$$

where $S_p$=Pattern Running Sum $S_h$=Hole Running Sum $N_p$=Number of Pixels in Pattern Sum $N_h$=Number of Pixels in Hole Sum For each row, the pixel scores are summed. The distance from the running average becomes the row score. FIG. 19 illustrates pixel scores (top), row sums (middle), and final row scores (bottom). These row scores can then be added into a running window sum for each row. When the running window sum reaches its maximum value, the window is centered on the splice and a detection has occurred. Any maximums that occur above a certain threshold are considered splices in the imagery. FIG. 20 illustrates row scores (top) and running window sum with detection threshold (bottom).

Figure 21:
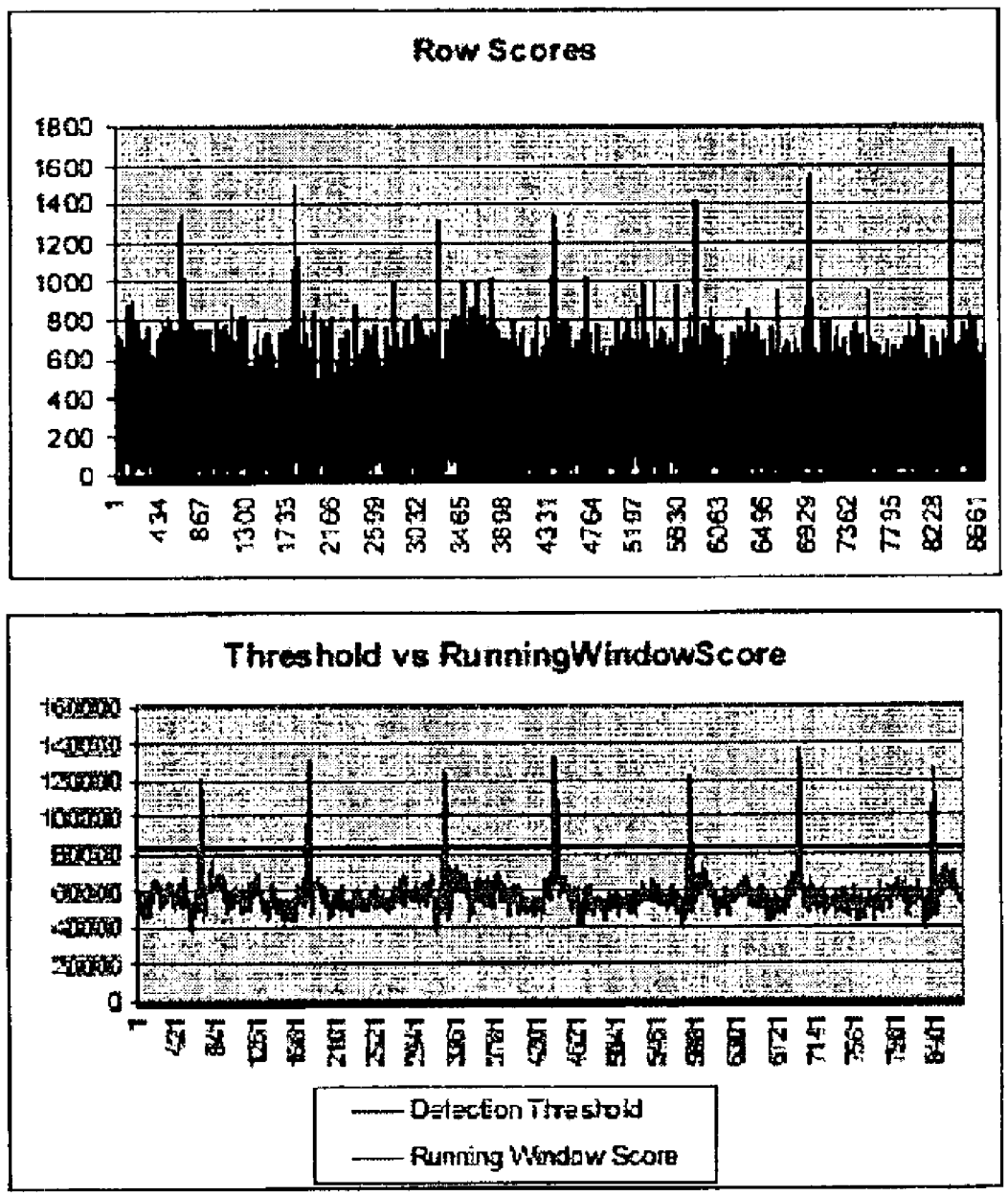
FIG. 21 illustrates one embodiment of row scores and running window sum.

The threshold used for detection can be calculated dynamically for changing lighting and belt situations. For example, keeping a running average of scores, the threshold may be programmed to stay above the running average by about fifty percent (50%). By examining the number of rows that fall above the threshold (in one group), some false positive situations can be eliminated. Detected features that do not have the correct width (which is the size of the mechanical splice and pixels) can be discarded as false detection. This may occur when the running window sum is noisy and may cross the threshold line a few times while climbing or falling a peak. FIG. 21 illustrates results of the algorithms running on a test rig with two splices on a 35-foot piece of belt in a continuous loop. In the figure, row scores are shown above and running window sums and thresholds are shown below.

After a mechanical splice has been detected, the BIS 20 may perform mechanical splice analysis. A mechanical splice on a coal mining belt is subjected to numerous types of stress. Impact force applied by rollers and scrapers, and heavy load forces produced by the loading of coal onto the belt are some of the more common types of stresses a mechanical splice experiences. Over time, these forces will cause the mechanical splice to break down and ultimately fail. When a mechanical splice fails, the belt breaks at the point where the mechanical splice was holding two pieces of belt together. As a result of the mechanical splice failure, all mining operations that are dumping coal onto the belt must stop until the belt is repaired.

In the BIS 20, once a mechanical splice has been detected by the system, it is sent to the object analyzer. There, it is analyzed for defects and a health score is assigned to the mechanical splice that represents the health of the splice. This health score may be used to trigger an alarm (e.g., audio or visual) when the health score falls below a specified safe threshold level. The purpose of the alarm is to notify mine personnel that a mechanical splice is in need of repair. The mine personnel can then manually inspect the mechanical splice using the BIS 20 and can decide whether or not to repair the splice immediately or at a later time, depending on the state of the splice. Ultimately, this may prevent unexpected belt breaks and keep mine operating down time to a minimum.

In order to detect defects, the system must know what a good splice looks like compared to one that is failing. To understand this, several common defects that occur in mechanical splices will be described and then a method used to assign a health score to a mechanical splice will be described. The methods described below receive an image of a mechanical splice as input and outputs a score representing the health of the splice, areas of the splice found to contain defects, and areas of the splice found to be acceptable. One or more of these methods may be used to score the mechanical splice. In one implementation, several methods are used with each method outputting its own scoring information. A function then combines the results in order to produce a robust final scoring output.

A mechanical splice essentially is made up of two rows of metal clips and a pin. In order to join two pieces of belt together, one row of clips is riveted to one piece of belt and another row of clips is riveted to the other piece of belt. The clips are pulled together such that their teeth overlap one another and the metal pin is driven through the hole that is formed between the teeth. When tension is applied to the belt, the metal clips pull on the pin and since the two rows of clips pull on the pin in opposite directions, the belt is held together. All parts of the splice must remain functional in order for the splice to hold the belt together. If any part starts to fail, the mechanical splice weakens and if enough parts fail, the splice will not be able to hold the belts together and the belts will break.

Figure 22:
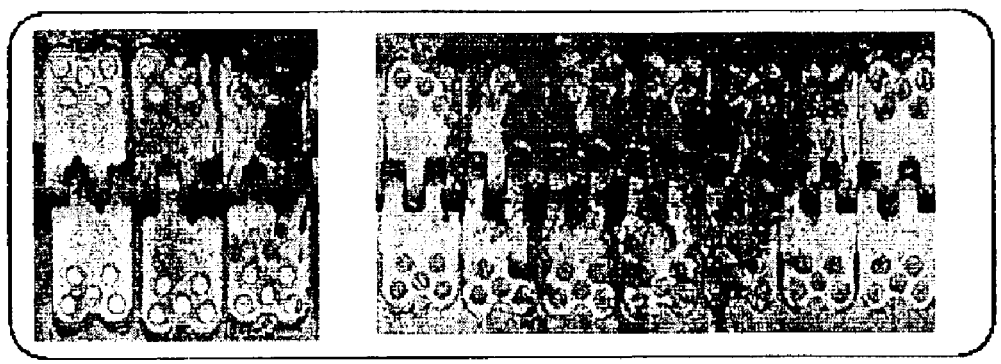
FIG. 22 illustrates one embodiment of a mechanical splice clips with different types of defects.
Figure 23:
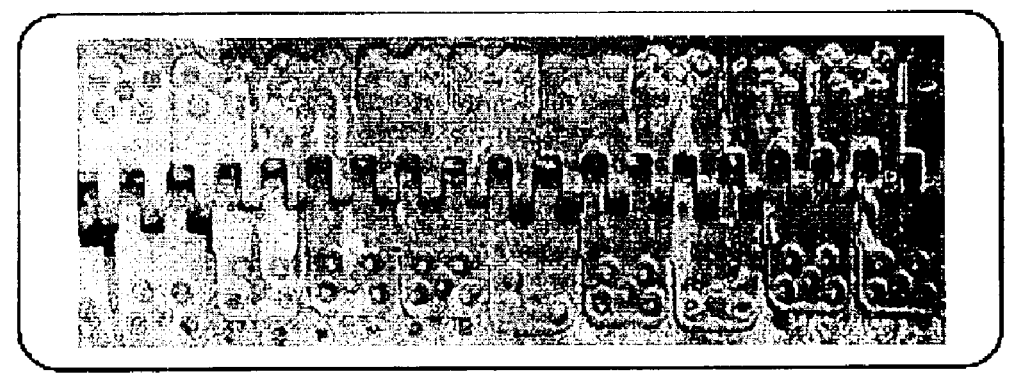
FIG. 23 illustrates one embodiment of a defective mechanical splice.
Figure 24:
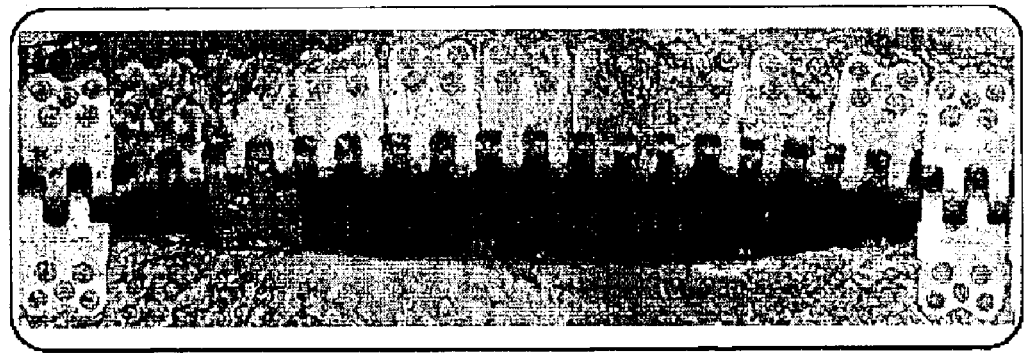
FIG. 24 illustrates one embodiment of a defective mechanical splice.
Figure 25:
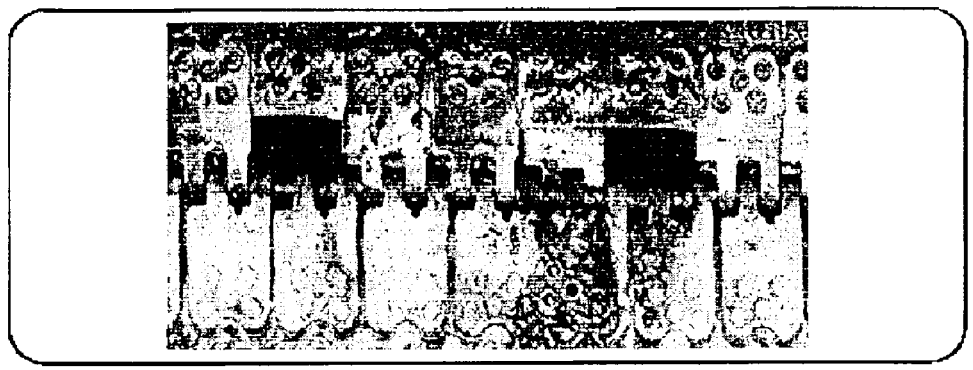
FIG. 25 illustrates one embodiment of a defective mechanical splice.
Figure 26:
FIG. 26 illustrates one embodiment of a defective mechanical splice.
Figure 27:
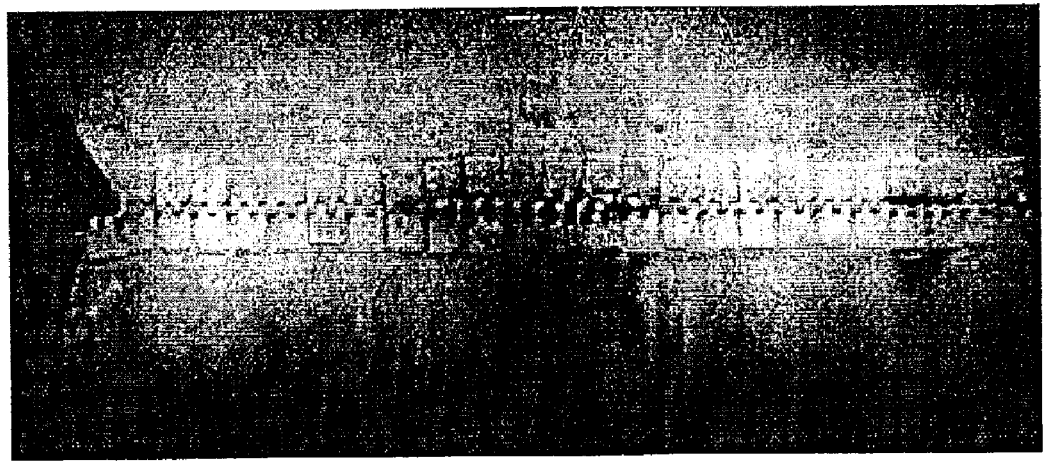
FIG. 27 illustrates one embodiment of a defective mechanical splice.

The following figures illustrate examples of how each part that makes up a splice may appear when it is failing. FIG. 22 illustrates mechanical splice clips with different types of teeth defects. As shown, a clip with a single broken tooth is shown on the left and several clips in a bottom row with broken/stretched teeth are shown on the right. FIG. 23 illustrates a mechanical splice with failing rivets. FIG. 24 illustrates a mechanical splice with an entire row of missing clips. FIG. 25 illustrates a mechanical splice with a few missing clips. FIG. 26 illustrates a mechanical splice with a broken pin. FIG. 27 illustrates a mechanical splice that is unzippering because a pin is starting to slide out.

Figure 28:
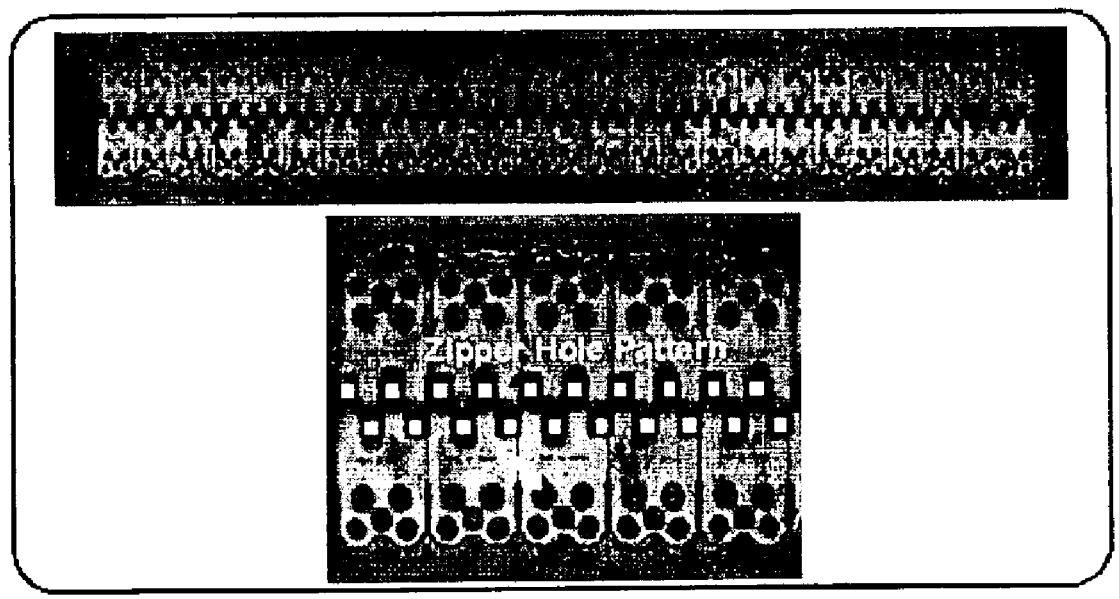
FIG. 28 illustrates one embodiment of a mechanical splice.

Various analysis methods may be used to assign a health score to a mechanical splice based on the number of defects that have been detected in the splice. In one embodiment, a health score may be based on the primary hole of each clip. This method of scoring focuses on examining the holes of the interleaving clips which form a zipper pattern. FIG. 28 illustrates an image of a mechanical splice with no defects (top) and a zoomed-in image of a splice highlighting the zipper hole pattern formed by the teeth of the clip (bottom). In a mechanical splice with no defects, the zipper hole pattern is uniform across the entire splice. However, in mechanical splices that contain defects, the zipper hole pattern is not uniform.

This method may include processing the image and finding the zipper holes that are contained between the teeth of the top and bottom rows of clips that make up the mechanical splice. Each located zipper hole is analyzed to determine its bounding box region. The size, alignment, and similarity of each of the identified zipper hole bounding box regions are then used to score the splice based on the uniformity that the zipper holes form across the splice.

Figure 29:
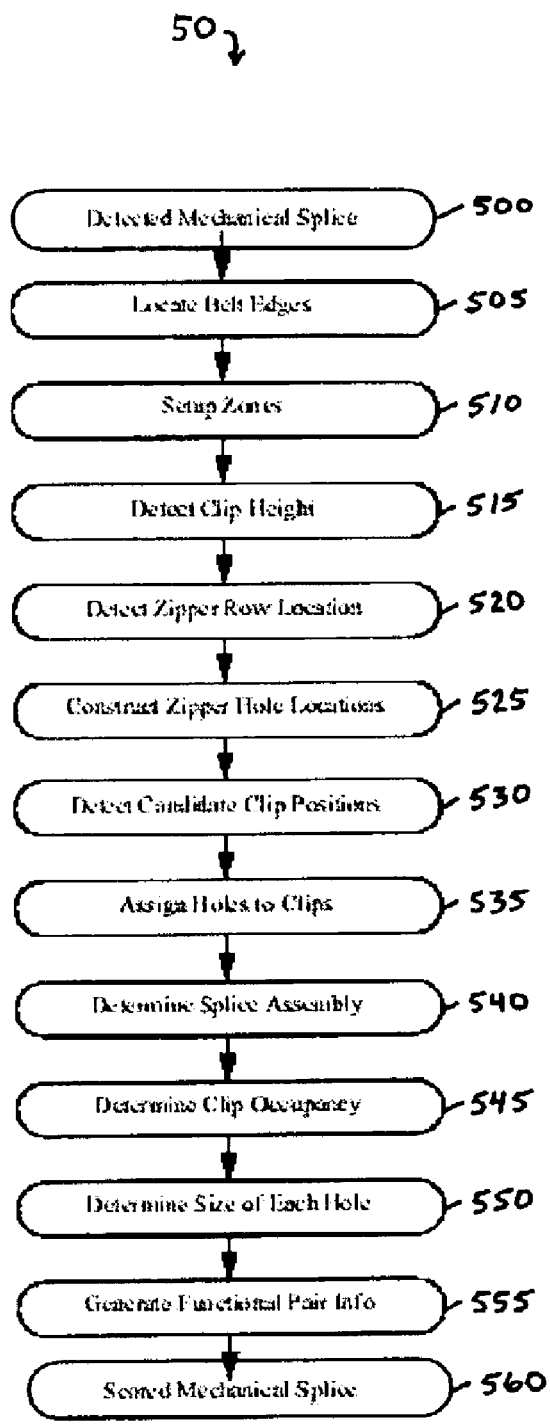
FIG. 29 illustrates one embodiment of a mechanical splice scoring algorithm.

FIG. 29 illustrates one embodiment of a mechanical splice scoring algorithm. In general, the mechanical splice scoring algorithm 50 may process a mechanical splice image in order to assign it a score based on analyzing the zipper hole pattern. In one implementation, the mechanical splice scoring algorithm 50 may be performed by a BIS 20 configured to detect a mechanical splice (step 500), locate belt edges (step 505), set up zones (step 510), detect clip height (step 515), detect zipper row location (step 520), construct zipper hole locations (step 525), detect candidate clip positions (step 530), assign holes to clips (step 535), determine splice assembly (step 540), determine clip occupancy (step 545), determine size of each hole (step 550), generate function pair information (step 555), and score the mechanical splice (step 560).

Figure 30:
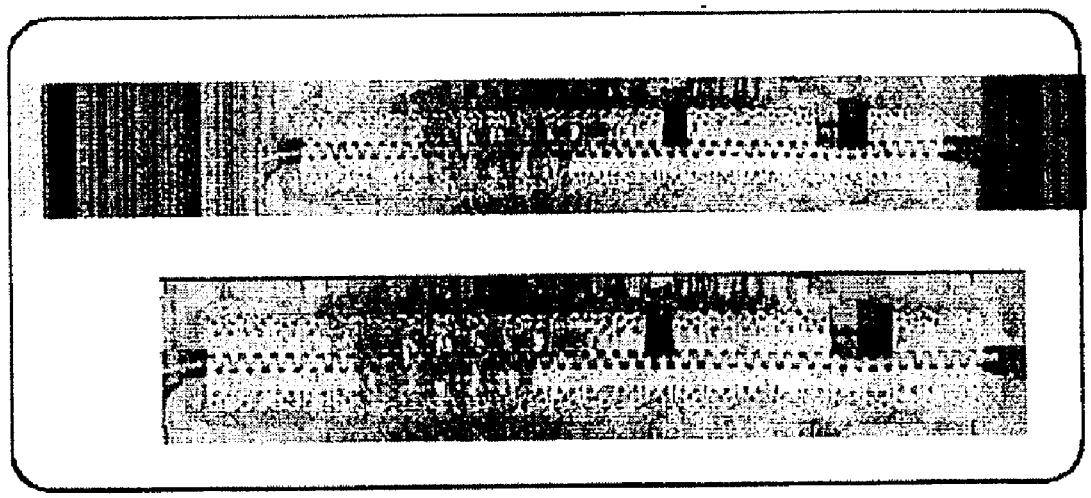
FIG. 30 illustrates one embodiment of an image of a detected mechanical splice and an extracted portion of the mechanical splice.

FIG. 30 illustrates an image of a detected mechanical splice used to describe the mechanical splice scoring algorithm 50 (top) and an extracted portion of the mechanical splice that contains data between located belt edges (bottom). Detecting the mechanical splice (step 500) may be performed as described above and/or in any other acceptable manner.

Locating belt edges (step 505) may be performed as follows. The image data between the belt edges is of interest to the system. This step processes the detected mechanical splice image and determines the image columns that contain the edge of the belt. In one implementation, the belt edge algorithm examines the pixel intensity variances of each column in the splice image. Areas of low variance are determined to be non-belt data as this imagery is of the static background and therefore should be fairly constant in intensity.

Figure 31:
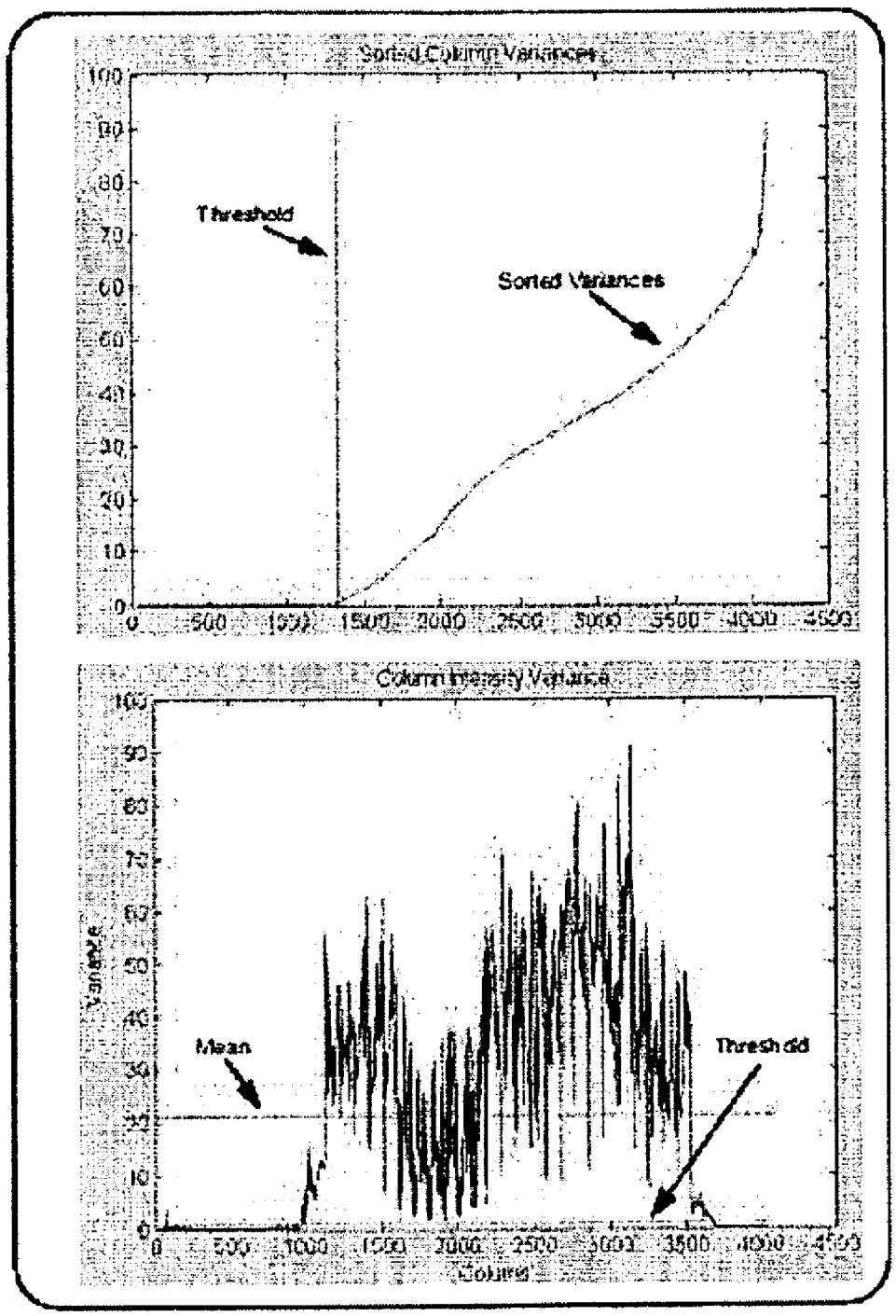
FIG. 31 illustrates one embodiment of sorted column variances of a mechanical splice and column variances with mean and threshold shown.

All column variances are sorted in ascending order. This sorted list is then searched to locate a point where the variances between adjacent points takes a relatively large step. This step is deemed to be the critical threshold level for classifying columns as belonging to either the background or part of the belt. Namely, columns with variances above the threshold are classified as belt and columns with variances below the threshold are classified as background. FIG. 31 illustrates sorted column variances of the mechanical splice (top) and column variances of the mechanical splice with mean and threshold (bottom).

The belt edge algorithm may use the computed mean variance as the starting point to look for the edge of the belt. The first column with a variance above the mean is used to search for the left side of the belt. The search may step backwards looking for the first occurrence of a column with a variance below the threshold level. This column is then deemed to be the start of the belt. Likewise, the last column with a variance above the mean is used to search for the right side of the belt. The search steps forward looking for the first occurrence of a column with a variance below the threshold level. This column is then deemed to be the end of the belt.

Setting up zones (step 510) may be performed as follows. A mechanical splice may appear at any angle in the detected image depending on how the splice is installed on the belt and how the BIS 20 is aligned with respect to the belt. Therefore, it may be necessary for the algorithm to handle splices appearing at angles in the imagery which will make the zipper hole pattern appear at an angle.

To account for such an angle, image data contained between the belt edges is split up into zones. The greater the number of zones, the smaller the amount of data contained in a zone and thus adjacent zipper holes in a zone appear nearly in the same row. The number of zones required is determined on a per installation basis depending on the angle at which the splices are appearing in the image.

Figure 32:
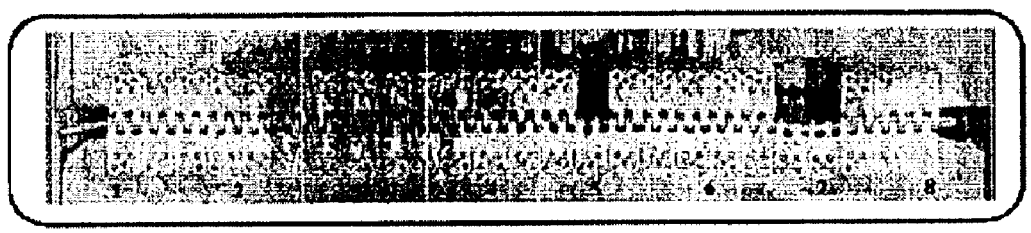
FIG. 32 illustrates one embodiment of a mechanical splice having zones.

This step constructs the zone boundaries across a belt imagery. The algorithm attempts to create equal sized zones, but may not be able to since it is constrained to make the center column of the image (the boundary point where the image data from the two cameras come together) a zone boundary point. FIG. 32 illustrates a mechanical splice with eight zones.

Detecting clip height (step 515) may be performed as follows. Detecting the belt edges limited the image data to be processed in the horizontal direction to the area containing the belt. This step looks to reduce the image data to be processed further by limiting the data to be processed in the vertical direction to only the data containing the mechanical splice. That is, this step determines the row location of the top of the top row of clips and the row location of the bottom of the bottom row of clips.

Detecting zipper row location (step 520) may be performed as follows. This step locates the zipper pattern in each of the image zones. In each zone, a zipper pattern template is slid across each row. For each row, the best template matching location and template slide offset are stored. Then, the template matching scores are analyzed to determine where the top and bottom zipper holes are located by determining the peak response of the scores. The row(s) containing a peak determine the row location and the slide location and the slide offset of that row determines the horizontal offset from the start boundary of the zipper pattern of that zone. If two peaks are detected, then the pin is determined to be at the local minima contained between the two peaks.

This step may be based on constructing a vertical edge magnitude image at the mechanical splice and using this information to determine the location of the zipper holes. However, it is important to note that either the comb or the piano keys method also may be used to detect the location of the zipper holes.

Figure 33:
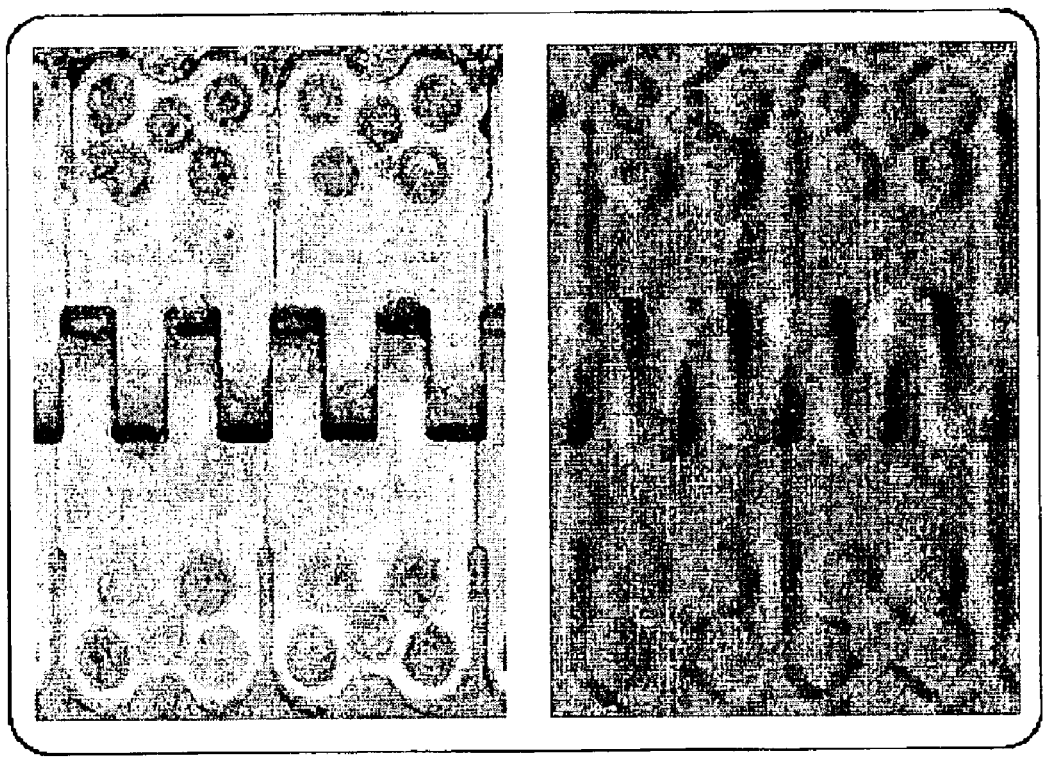
FIG. 33 illustrates one embodiment of a portion of a mechanical splice and a vertical edge magnitude image.

FIG. 33 illustrates an image portion of a mechanical splice (left) and its vertical edge magnitude image (right). As shown, the vertical edge magnitude image of the mechanical splice includes values ranging from negative (dark intensities) to positive (light intensities). By examining the shape of the edge magnitudes along a row containing the zipper holes, a regular pattern may be seen which can be used to develop a template pattern that scores highly when the regular pattern is compared to the template.

Figure 34:
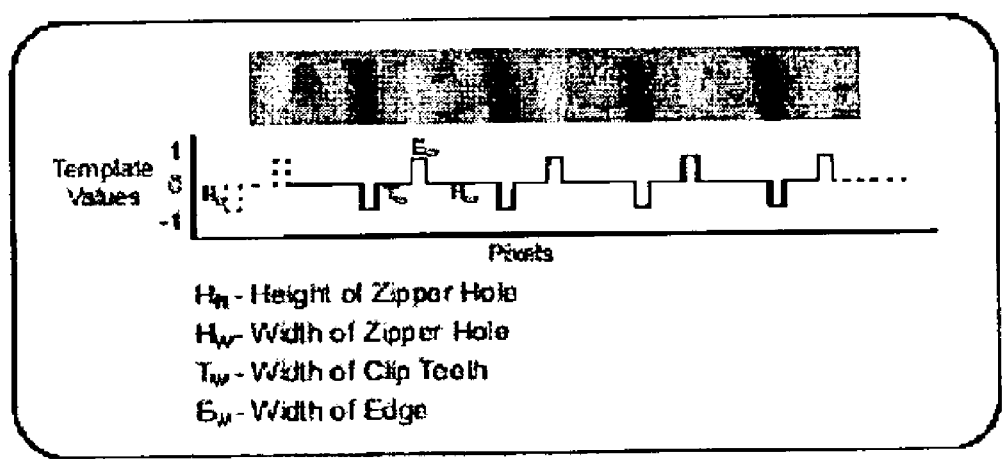
FIG. 34 illustrates one embodiment of an edge template pattern.

FIG. 34 illustrates an edge template pattern construction. The template pattern for locating the zipper hole pattern is constructed from the user defined geometry of the mechanical clips that are on a particular belt. As shown in the figure, the top image is a vertical edge magnitude image along the zipper holes of the mechanical splice and the middle diagram is the template pattern constructed to match the vertical edge magnitude zipper hole pattern and can be defined with the user configurable variables provided at the bottom of the figure.

In each zone, a two-dimensional template pattern is constructed that is the height of the zipper holes tall and is as wide as the width of the zone. This template pattern is applied at several offset locations in each row. For each row, the offset that produces the maximum response is recorded as well as the maximum response itself.

Figure 35:
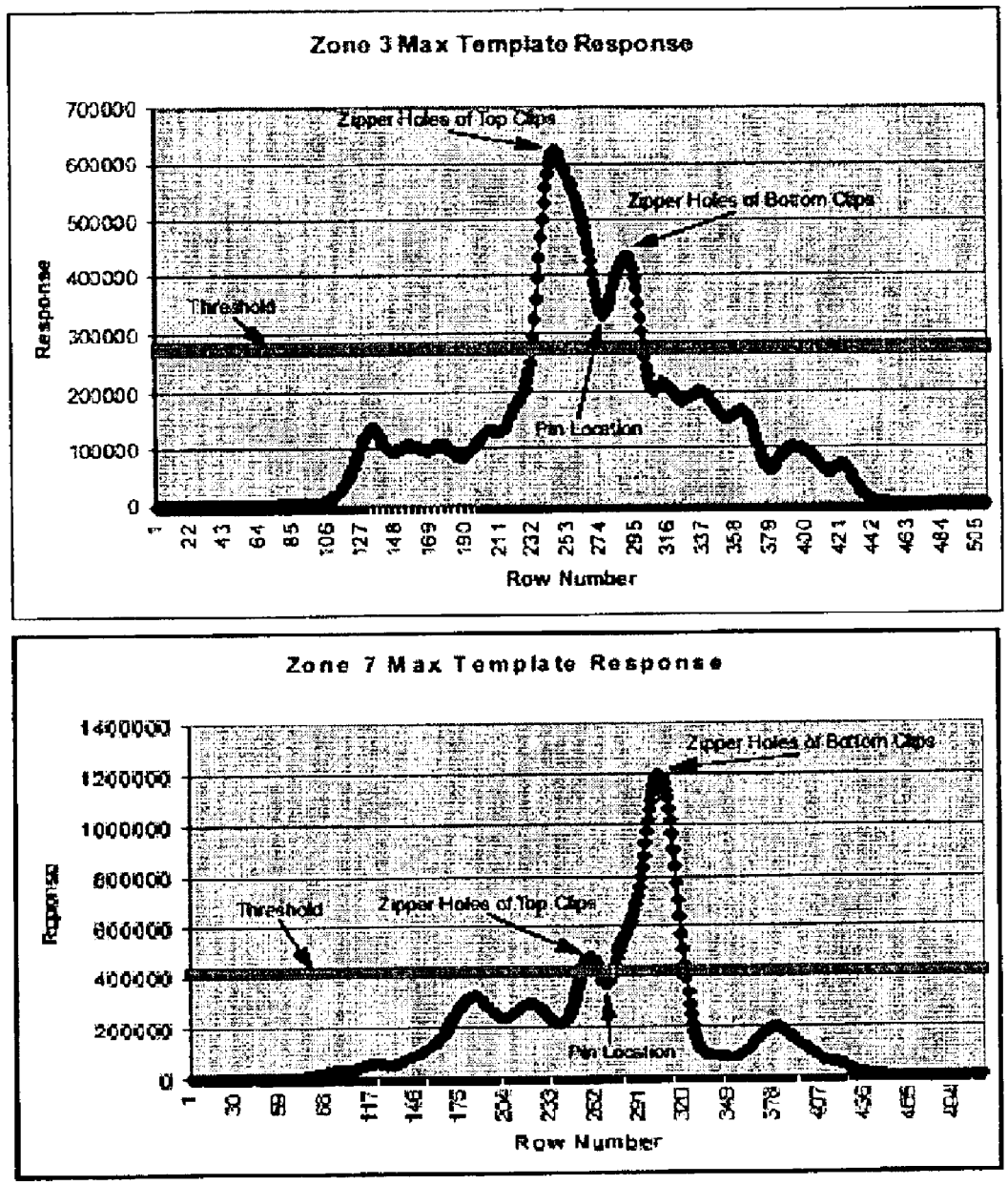
FIG. 35 illustrates one embodiment of a maximum template response.

FIG. 35 illustrates maximum template responses for each row in section 3 (top) and in section 7 (bottom). The maximum template row response scores are processed to determine the location of the peak response. An area around this location is then searched for another peak. These two peak locations, if found, are compared to a threshold level which is the mean template response times a multiplier. If both peaks are above the threshold, then they represent the top and bottom zipper hole row locations. If two peaks are found, then the pin row location for that section is determined by locating the local minimum contained between the two peaks. If only one peak was found, and it is above the threshold level, then this indicates that only one zipper row was found and it cannot be determined, yet, if the row belongs to the top or bottom row of clips. If no peaks are found, then there are no zipper holes in this section, which can happen if a section contains a portion of a mechanical splice with all clips missing.

Constructing zipper hole locations (step 525) may be performed as follows. This step takes the row and offset locations for the top and bottom zipper holes and the pin row location in each zone and constructs a list of zipper hole center estimates for the top and bottom clips. Construction of the top zipper holes list starts in the first section where the first hole is placed top zipper hole offset pixels from the start of the boundary of the first zone. Additional hole centers are added to the list by an amount equal to one clip hole width and one clip tooth width. This continues until a hole center goes beyond the end of the first zone boundary. A similar process is then carried out in each zone continuously adding to the list of top and bottom zipper hole center locations.

If a zone is encountered in which only one zipper row was detected, its row location is examined against neighbor zone locations to determine if it belongs to the top or bottom zipper hole list. The missing row of holes is then extrapolated from the nearest neighbor in which that row of zipper holes was detected. If the zone is encountered in which no zipper hole locations were located, then hole locations are extrapolated from the nearest neighbor in which top and bottom zipper holes were detected. This process produces a complete list of estimated top and bottom center zipper hole locations. Each zipper hole also contains information as to where its pin location was detected.

Once constructed, the list is post-processed to fill in any gaps and to remove any redundant holes that may have resulted from the previous step. This results in a complete list of zipper hole center locations for the top and bottom row of clips that span the entire length of the detected width of the belt regardless if the clips are installed to the end of the belt or not.

Using a template of the size of a single zipper hole wide by a single zipper hole high, a small area around each zipper hole is then searched to determine if a better zipper hole location can be found. The best template response in the search is then used to update the estimated hole center with a true hole location. Differences in estimated and true hole locations are noticeable when the splice is at an angle in the image and in areas where the zipper pattern is not continuous in a single row due to some clip defect.

Figure 36:
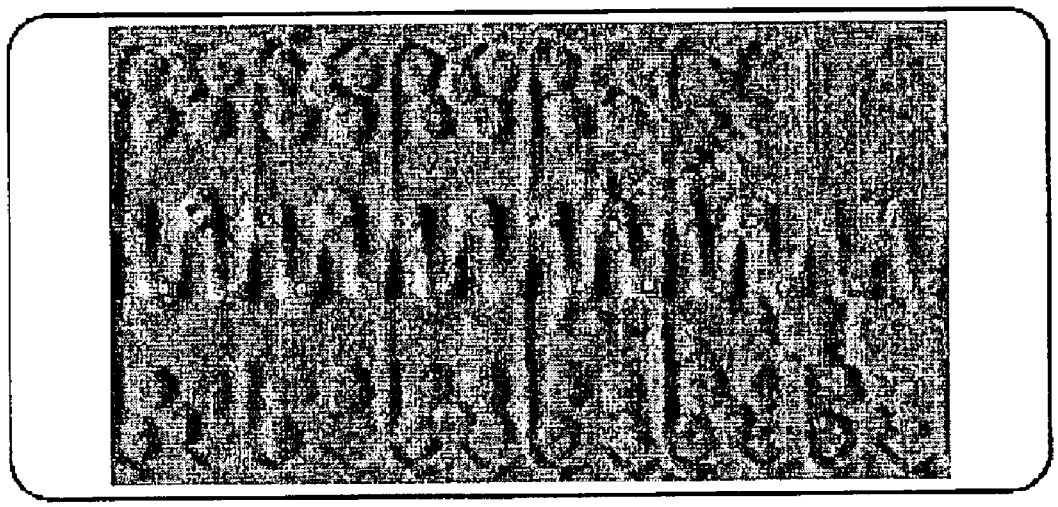
FIG. 36 illustrates one embodiment of a vertical edge magnitude image.
Figure 37:
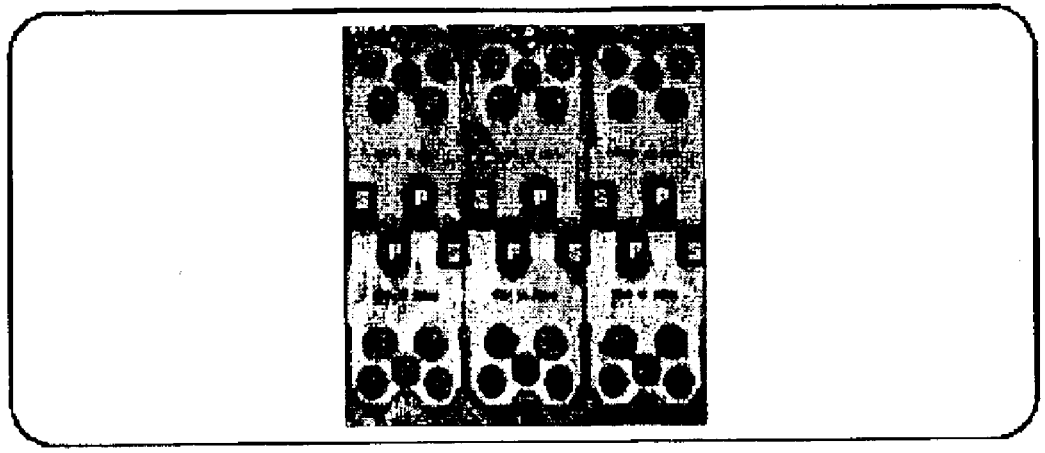
FIG. 37 illustrates one embodiment of a portion of a mechanical splice with primary and secondary holes.
Figure 38:
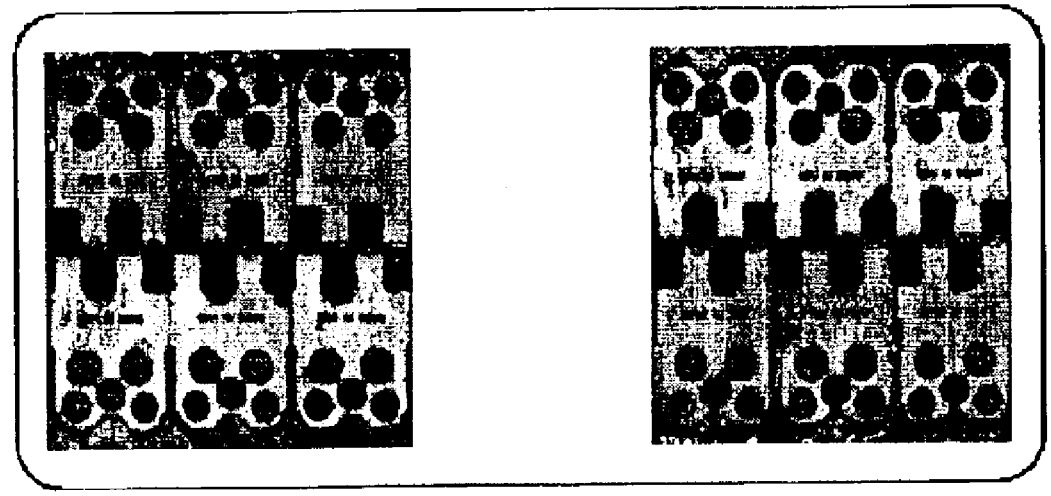
FIG. 38 illustrates one embodiment of clip edge alignment types.

FIG. 36 illustrates a portion of a mechanical splice with both the estimated and determined to be true zipper hole locations. As shown, the vertical edge magnitude image of the mechanical splice is overlaid with the estimated (x's) and the true (squares) zipper hole center locations.

Detecting candidate clip positions (step 530) may be performed as follows. This step uses the list of zipper hole center locations from the previous step, the vertical edge magnitude image, and knowledge about the geometry of the clips in order to determine the location and style of the clips in the top and bottom rows of the mechanical splice. The terms that are referenced in this step are defined as follows.

FIG. 34 defines what is meant by the primary and secondary zipper holes and clip. As shown, the figure illustrates a portion of a mechanical splice with primary (P) and secondary (S) holes labeled. Primary holes are contained between the teeth of a single clip while the secondary holes are contained between the teeth of adjacent clips.

FIG. 35 defines the different possible clip styles. As shown, the figure illustrates examples of various clip edge alignment types based on the tooth that lines up with the edge of the clip. In the left image, top clips are right-edge and bottom clips are left-edge aligned. In the right image, top clips are left-edge and bottom clips are right-edge aligned.

The top zipper hole center locations are contained in a list such that they are in sequential order from left to right in the mechanical splice image across the length of the detected belt width. Furthermore, the hole locations have been generated such that every odd numbered hole is either a primary or secondary hole and every even numbered hole must be the opposite hole type. Generating the list in such a manner constrains the problem of determining the correct possible location and style of the clips that must be associated with the holes.

Figure 39:
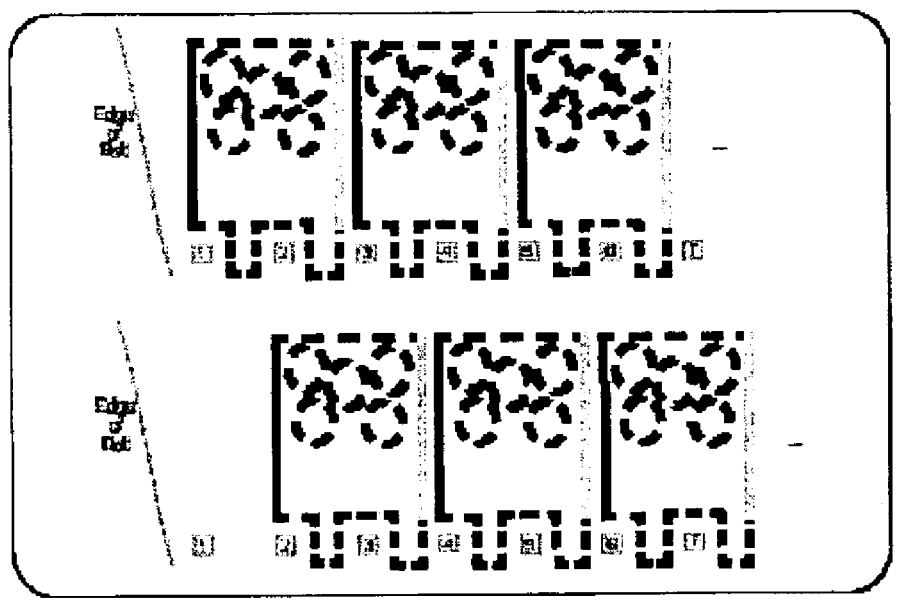
FIG. 39 illustrates one embodiment of top row clips—right edge aligned templates.
Figure 40:
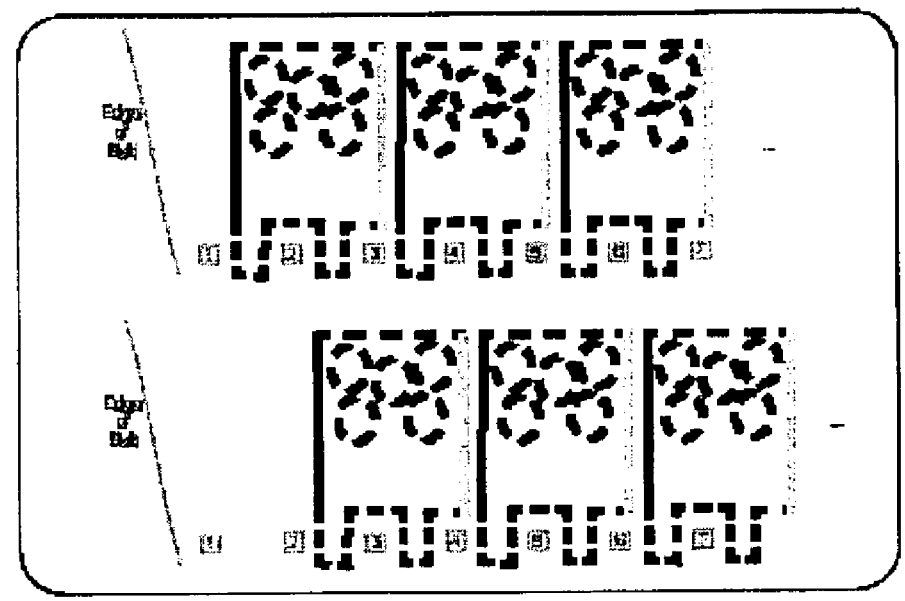
FIG. 40 illustrates one embodiment of top row clips—left edge aligned templates.

In fact, there are only four possible clip location and style assignments that make sense, as shown in FIG. 39 and FIG. 40. Referring to FIG. 39, top row clips—right edge aligned templates define primary holes by either even (top) or odd (bottom) numbered zipper holes. Referring to FIG. 40, top row clips-left edge aligned templates define primary holes by either even (top) or odd (bottom) numbered zipper holes.

These figures show templates that are used to determine the location and style type of the clips in the top row of the mechanical splice. The dashed lines in the templates area are shown only to graphically illustrate that each template is of a particular clip style. That is, no actual template matching takes place at the dashed line locations. The solid black lines in the templates represent areas in which the vertical edge magnitude image is expected to contain negative values. The solid gray lines in the templates represent areas in which the vertical edge magnitude image is expected to contain positive magnitude values.

The top zipper hole center locations indicate where the holes are located in the vertical edge magnitude image. The geometry of the template is based on the user-defined geometry of the clips which is stored in a configuration file. The hole locations are used to guide where the template matching occurs in the vertical edge magnitude image.

Figure 41:
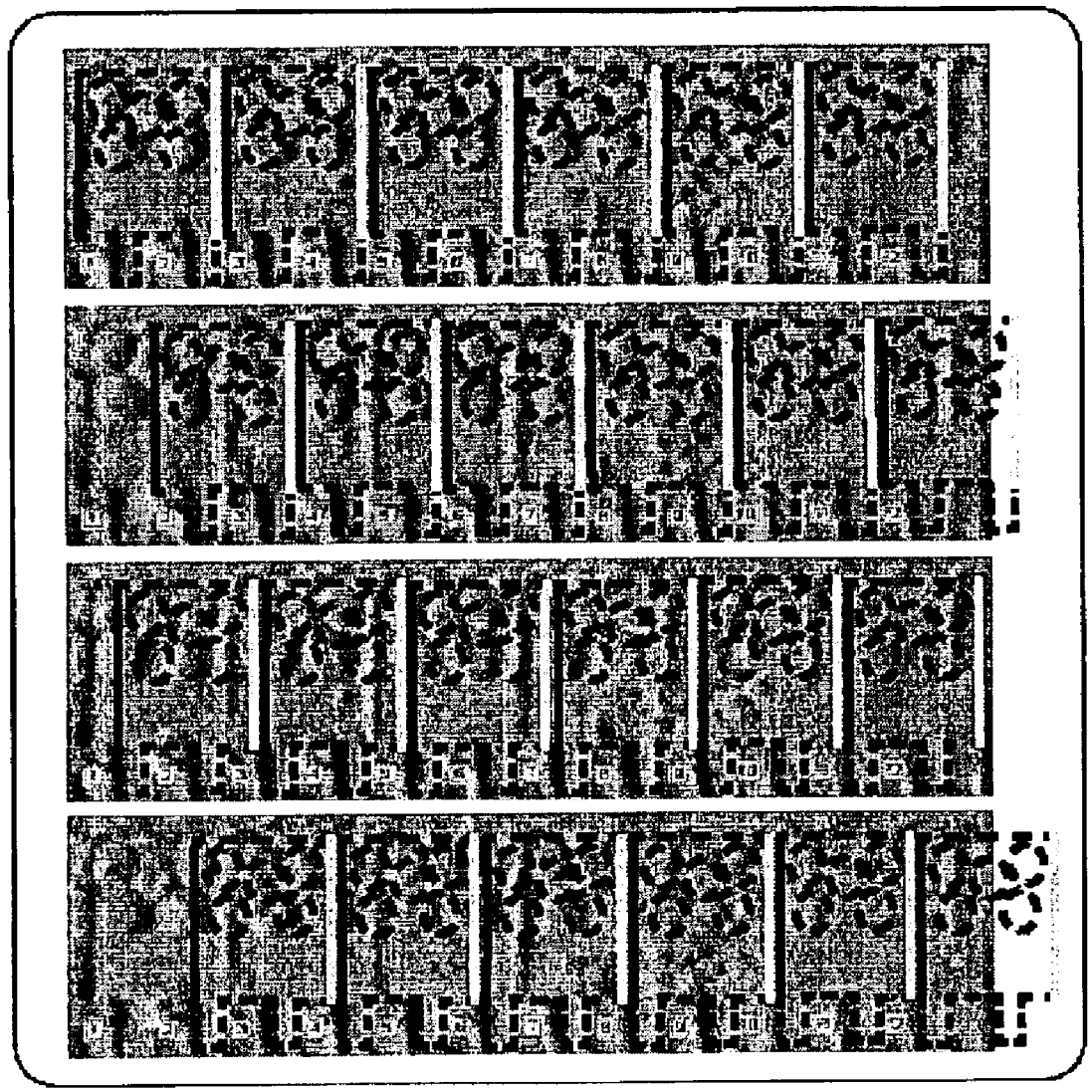
FIG. 41 illustrates one embodiment of applying clip templates.

FIG. 41 illustrates an example of applying the four possible clip templates to determine the location and style of the clips in the top row of the mechanical splice. As shown, the vertical edge magnitude image of the top row of clips is overlaid with each of the four possible clip style templates to show where each template looks for a particular pattern. In this case, the first template matches the best and hence the top row of clips is determined to be right edge aligned with even numbered primary holes.

In FIG. 41, an image is repeated four times and each one of the four possible clip styles is overlaid on top of the edge magnitude image. Four scores are computed to represent how well each template matches the clip style present in the vertical edge magnitude image. Each template score may be computed by summing all of the areas in the vertical edge magnitude image where the gray solid lines are located and subtracting from that the sum of all of the areas where the black solid lines are located. The template with the highest score determines the location and the style of the clips in the top row of the mechanical splice.

Figure 42:
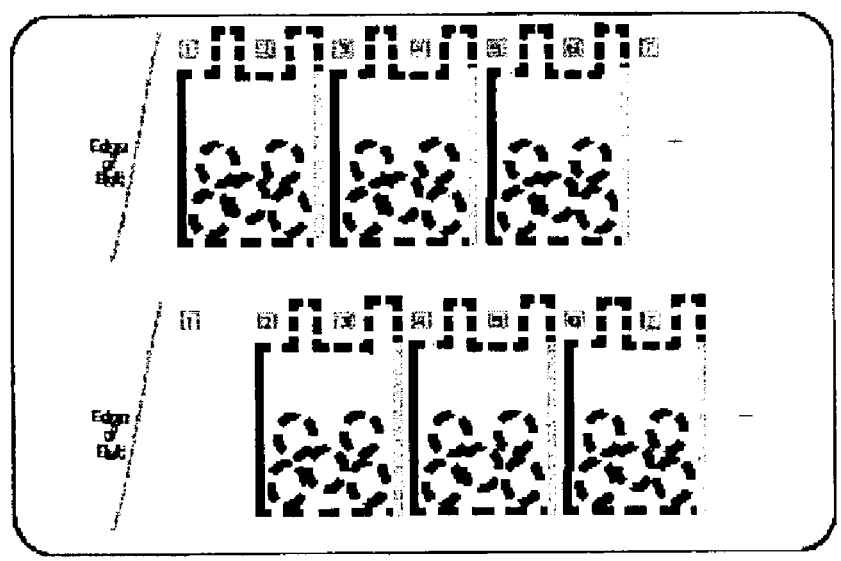
FIG. 42 illustrates one embodiment of a bottom row clips—right edge aligned templates.
Figure 43:
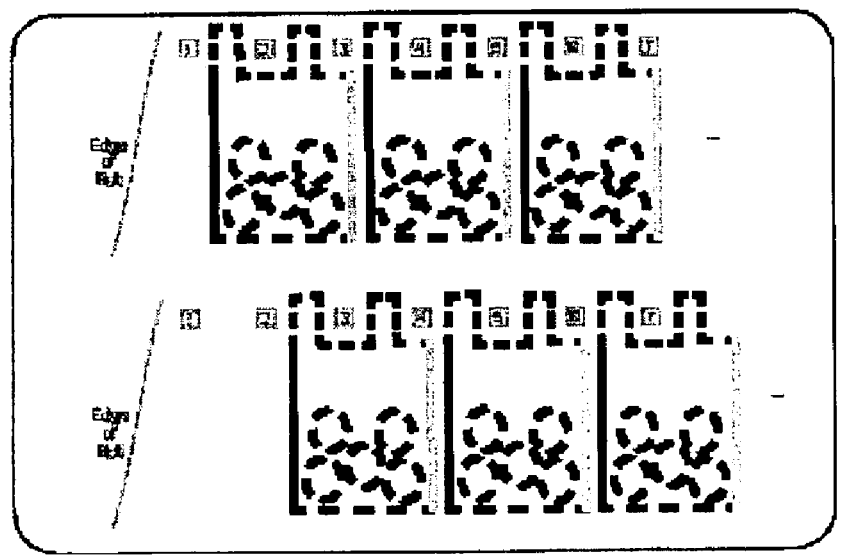
FIG. 43 illustrates one embodiment of a bottom row clips—left edge aligned templates.

A similar process is then carried out to locate the bottom clips of the mechanical splice. Again, the four possible clip location and style assignments are shown in FIG. 42 and FIG. 43. Referring to FIG. 42, bottom row clips—right edge aligned templates define primary holes by either even (top) or odd (bottom) numbered zipper holes. Referring to FIG. 43, bottom row clips—left edge aligned templates define primary holes by either even (top) or odd (bottom) numbered zipper holes.

These figures show templates that are used to determine the location and style type of the clips in the bottom row of a mechanical splice. The dashed lines in the templates area are shown only to graphically illustrate that each template is of a particular clip style. That is, no actual template matching takes place at the dashed line locations. The solid black lines in the templates represent areas in which the vertical edge magnitude image is expected to contain negative values. The solid gray lines in the templates represent areas in which the vertical edge magnitude image is expected to contain positive magnitude values.

The top zipper hole center locations indicate where the holes are located in the vertical edge magnitude image. The geometry of the template is based on the user-defined geometry of the clips which is stored in a configuration file. The hole locations are used to guide where the template matching occurs in the vertical edge magnitude image.

Figure 44:
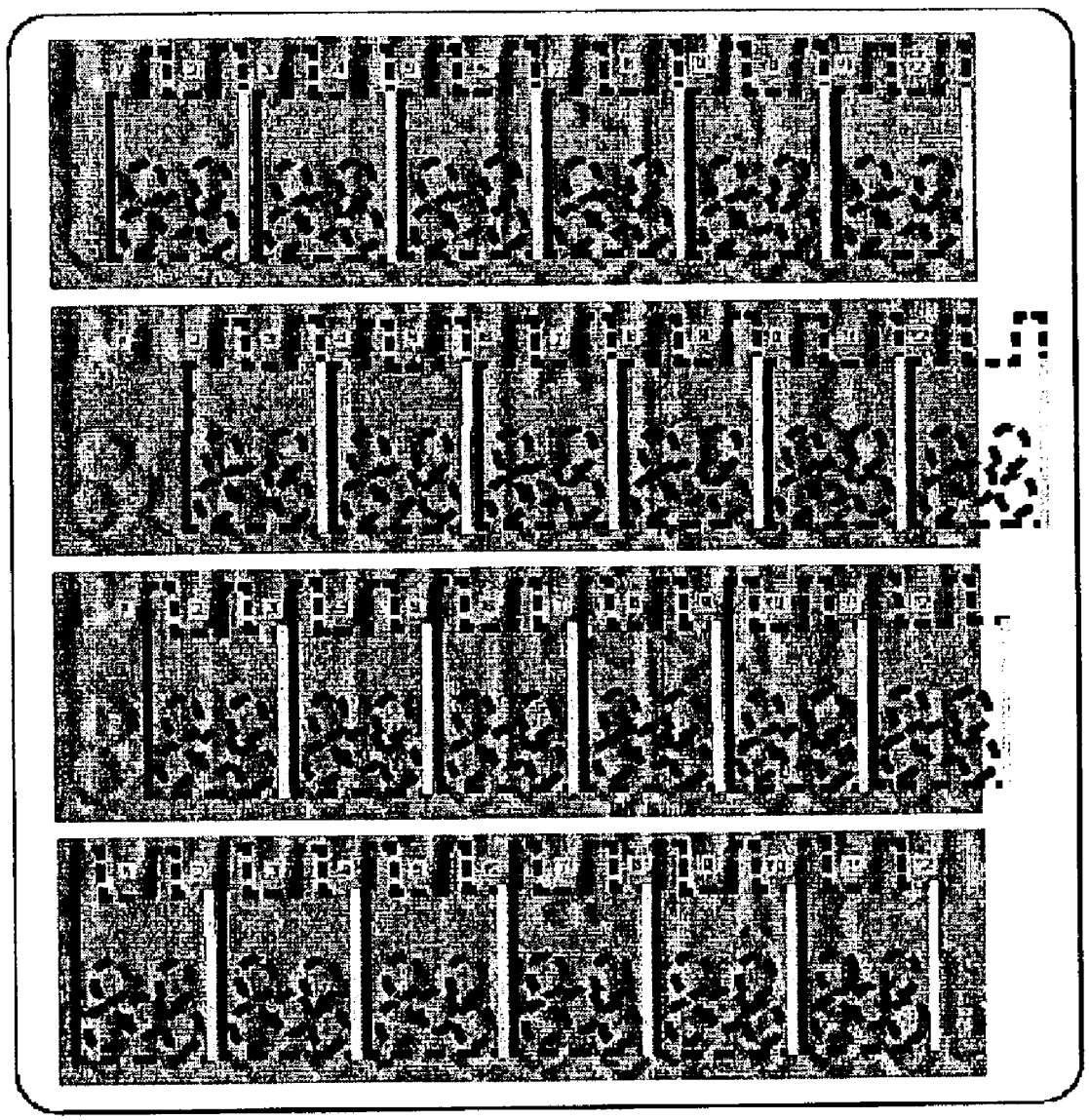
FIG. 44 illustrates one embodiment of applying clip templates.

FIG. 44 illustrates an example of applying the four possible clip templates to determine the location and style of the clips in the bottom row of a mechanical splice. As shown, the vertical edge magnitude image of the bottom row of clips is overlaid with each of the four possible clip style templates to show where each template looks for a particular pattern. In this case, the last template matches the best and hence the bottom row of clips is determined to be left edge aligned with odd numbered primary holes.

In FIG. 44, the image is repeated four times and each one of the four possible clip styles is overlaid on top of the edge magnitude image. Four scores are computed to represent how well each template matches the clip style present in the vertical edge magnitude image. Each template score is computed by summing all the areas in the vertical edge magnitude image where the gray solid lines are located and subtracting from that sum all of the areas where the black solid lines are located. The template with the highest score determines the location and the style of the clips in the bottom row of the mechanical splice.

Figure 45:
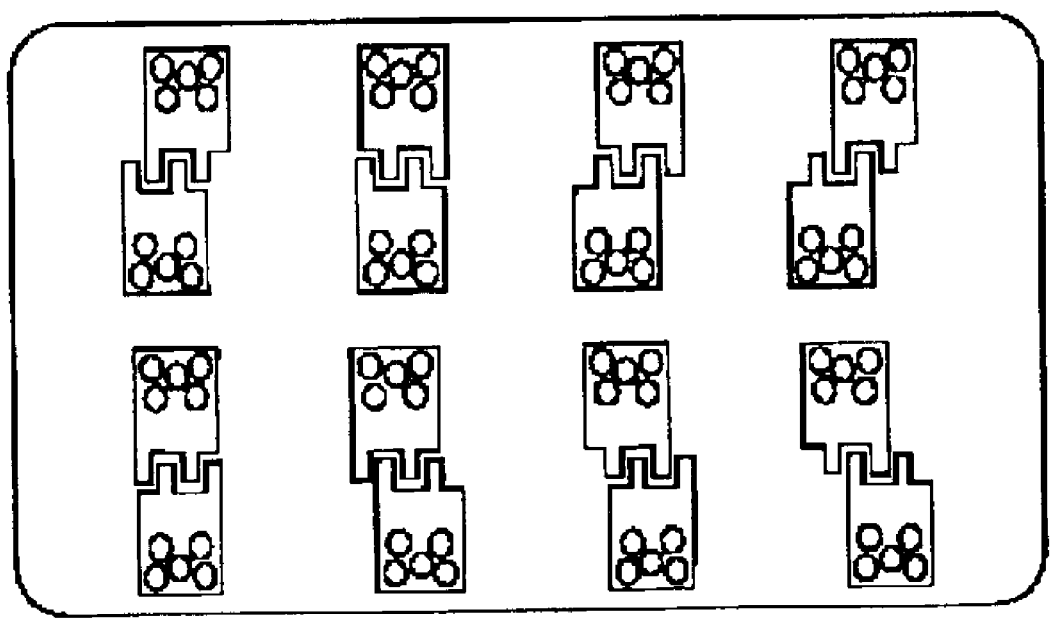
FIG. 45 illustrates one embodiment of clip mate assembly styles.
Figure 46:
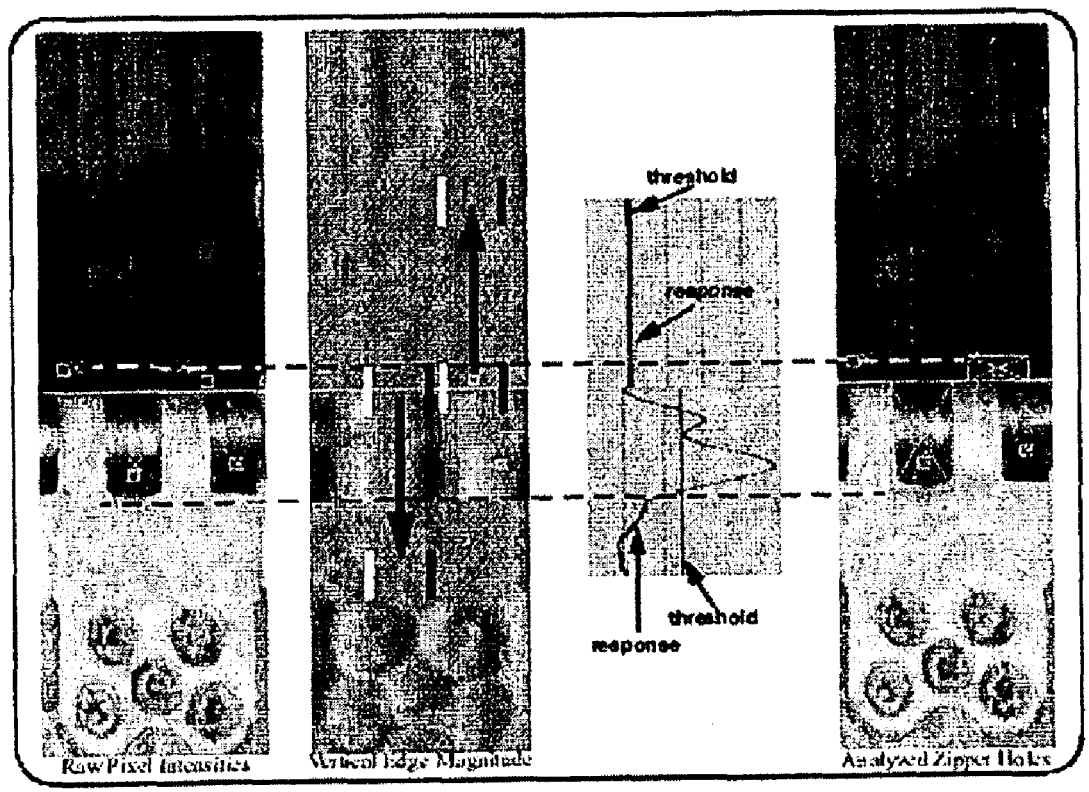
FIG. 46 illustrates one embodiment of a hole growing process.
Figure 47:
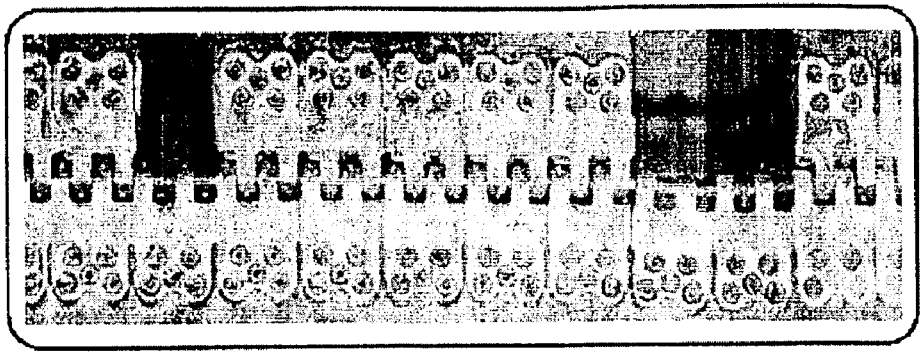
FIG. 47 illustrates one embodiment of a scoring result of a mechanical splice.
Figure 48:
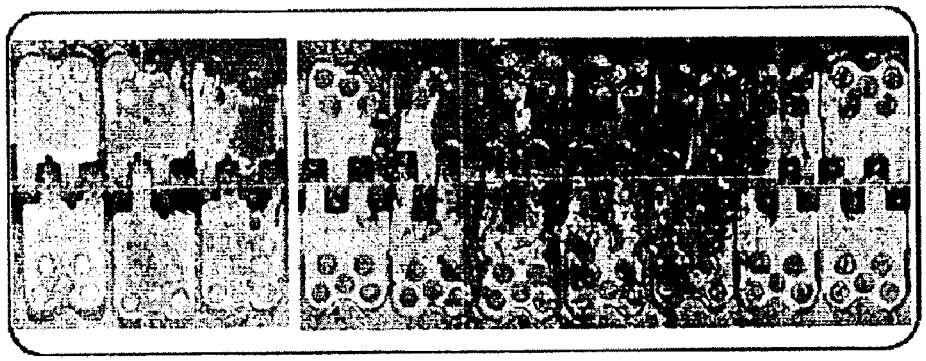
FIG. 48 illustrates one embodiment of scoring results on mechanical splice clips.
Figure 49:
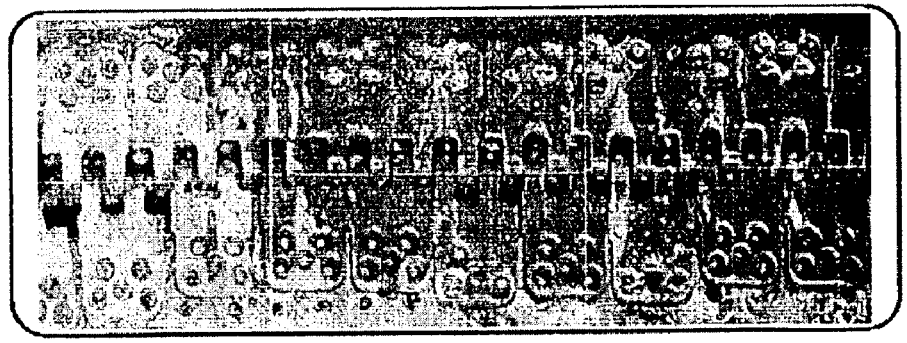
FIG. 49 illustrates one embodiment of scoring results on mechanical splice clips.
Figure 50:
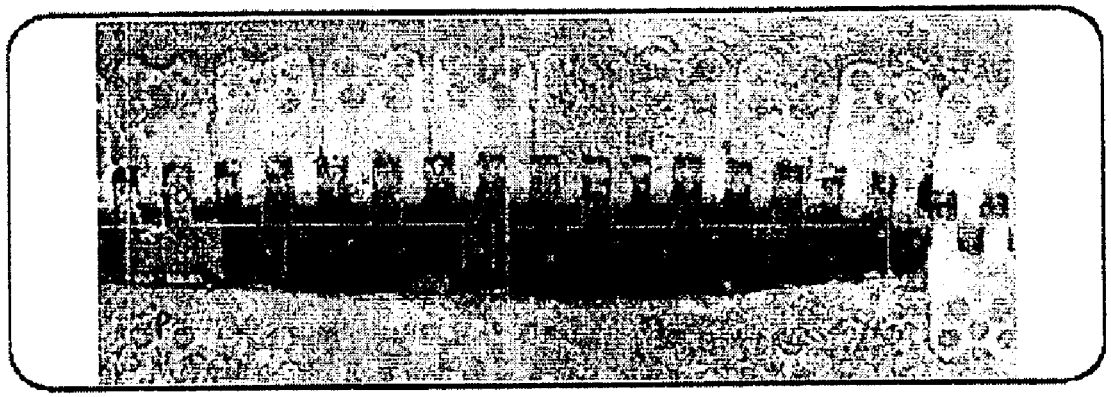
FIG. 50 illustrates one embodiment of scoring results on a mechanical splice.

Assigning holes to clips (step 535) may be performed as follows. From the previous step, the style and locations of the clips in both the top and bottom row of the mechanical splice are known. This step assigns the zipper holes in the top and bottom row to their respective clips and marks them as either a primary or secondary hole. In one implementation the top and bottom clips are analyzed in order to determine how the mechanical splice is assembled and to assign each clip in the top row with a mate in the bottom row. FIG. 45 illustrates eight different possible assembly options.

To determine how the splice is assembled, the primary hole of each clip in the top row is analyzed. For each primary hole in the top row, the algorithm searches for a clip in the bottom row whose primary hole is within one and one-half zipper hole widths in the horizontal direction. If it finds one, it increments the support score for 45 degree assembled if the top hole is located to the right of the bottom hole; otherwise, it increments the support score for 135 degree assembled. The assembly style score with the most support is then assigned as the assembly style of the mechanical splice. The algorithm then goes over each clip in the top row and assigns it a matching clip mate in the bottom row based on this assembly style.

Determining clip occupancy (step 545) may be performed as follows. This step determines whether a clip is present or not. In one implementation, only those candidate clips in which a clip is determined to be present are processed.

Determining the size of each hole (step 550) may be performed as follows. This step analyzes the primary hole of each clip. All holes are first analyzed to determine their height. A pass is then made over the holes to determine the median hole height in the top and bottom rows of clips. A second pass is then made over the holes where each hole is compared to its respective median hole height. If the hole is within some configurable tolerance of the median hole height, then the hole is determined to be free of defects. Otherwise, the hole is marked as having a defect.

FIG. 43 illustrates an example of how the primary hole height is determined. From left to right: raw pixel intensities of a clip mate pair, their vertical edge magnitude image, the temperate response of growing each of the top and bottom zipper holes and the resultant zipper hole heights overlaid on the raw pixel intensity image. The vertical edge magnitude image shows the zipper hole template that is slid over the image in order to produce the response shown in the graphs. The template contains a positive edge (shown in gray) and a negative edge (shown in black) $E_W$ thick and separated by $H_W$. The summed black area is subtracted from the summed gray area to obtain a response at a particular row location.

Generating functional pair information (step 555) may be performed as follows. This step analyzes each clip mate pair to determine if they make up a functional pair of clips or not i.e., whether or not they are supporting holding the belt together. If the top and bottom clips that make up the clip mate pair are both present and their primary holes are both determined to be healthy, then the number of functional clip pairs present in the mechanical splice is incremented. The total number of functional clip pairs is assigned to be the health score of the mechanical splice.

Scoring the mechanical splice (step 560) may be performed as follows. FIG. 47 through FIG. 50 illustrate examples of how the scoring algorithm locates various kinds of mechanical splice defects. In each figure, vertical lines represent a section boundary line, horizontal lines are the location of the pin in a particular section, the small x's are the estimated zipper hole locations, the boxes are the refined zipper hole center locations, and the boxes containing an X represent clips that the algorithm has marked as having a defect. Clips that do not contain a primary zipper hole with an X-out box are clips that the algorithm has determined to be free of defects.

There may be some drawbacks associated with scoring based on analyzing primary holes. In particular, mechanical splices appearing at an angle in an image may present a problem. The determination of the size of the primary zipper holes assumes that the bottom (in the case of the top zipper holes) and the top (in the case of the bottom zipper holes) of the hole boundaries are determined by the pin location. The pin location was determined as a result of detecting the zipper hole pattern within each given zone. Unfortunately, the pin location in each zone is assumed to appear horizontally in an image. In actuality, this is not the case when the splice appears at an angle. Therefore, when a zone is large enough to encapsulate several mechanical clips and the pin is assumed to be horizontal, then the zipper holes for the clips at the ends of the zone automatically have a larger size than the ones for the clips in the middle. This results in a large number of zipper holes being labeled erroneously as having a defect. The solution to this problem may include a step in the scoring process that determines the angle of the splice in the image and using this information to account for the above problem.

In addition, the zipper holes when filled with mud may present a problem. When the zipper holes and teeth get filled or covered with mud, it makes the detecting of the zipper holes difficult as the contrast between holes, clips, or teeth becomes almost indistinguishable. This is a problem for any scoring method which analyzes the zipper holes or clip teeth. The solution to this problem is to combine this scoring method with another method based on some other clip or splice feature which would make the entire scoring process more robust and accurate.

Figure 51:
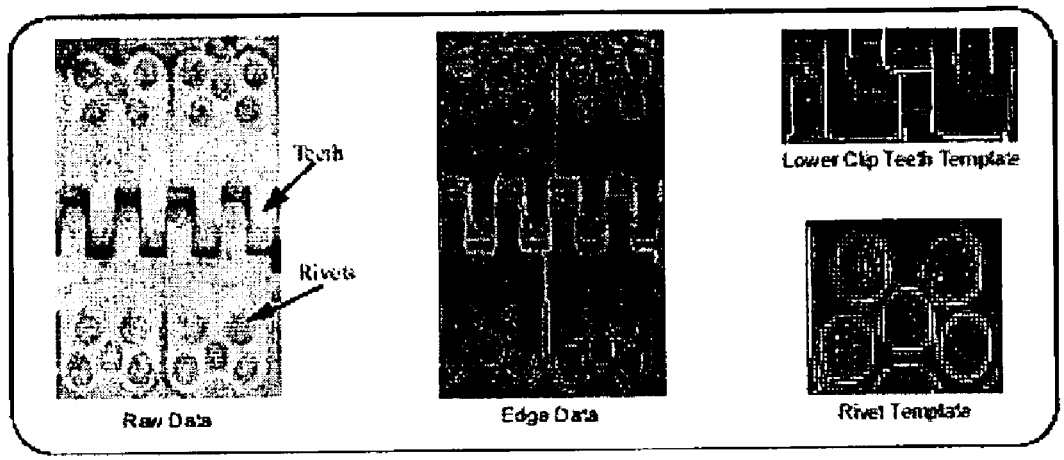
FIG. 51 illustrates one embodiment of a raw data and edge space clips.

Another example of a scoring method, for example, is a template matching method. This method passes several template matching filters over the image in order to identify areas where clips are located in the image. Template filters are constructed to look for specific features in the image such as the teeth and rivet patters present on each clip that make up the mechanical splice. From the original template filter, additional template filters can be constructed to allow for scale and rotation variances of the clips as they appear in the image. The filtered template mechanical splice image produces an image that contains areas with high correlation scores. These are areas where the mechanical splice image data matches the template filter well and indicates that a clip is present at this location. Detected areas with high correlation matching scores are compared in size, alignment and similarity to produce a health score for the mechanical splice. Template filters may be constructed based on pixel and edge intensities. FIG. 51 illustrates raw data and edge clips with example teeth and rivet edge templates.

Another example of scoring may be based on machine learning methods. For example, machine learning methods (such as Neural Nets, Support Vector Machines, etc.) have been applied to solve object classification problems with great success. A database of previously detected mechanical splices may be manually scored by a human expert and then used to train the network. The trained network could then be used to score future detected splices.

In one embodiment, the BIS 20 may be configured to perform vulcanized splice detection. The BIS 20 may perform vulcanized splice detection in addition to and/or independent of mechanical splice detection, as described above. In general, a vulcanized splice holds two pieces of belt together in a manner different from a mechanical splice. Just as in the case of a mechanical splice, however, a vulcanized splice can fail causing the belt to break. When a vulcanized splice breaks, it may be more costly to the mine because it takes longer to repair than a mechanical splice which means more belt and production downtime. Therefore, it is important to be able to monitor and evaluate vulcanized splices.

Unlike mechanical splices, vulcanized splices generally do not have a feature that can be used to easily distinguish it from the rest of the belt. In one implementation, performing vulcanized splice detection includes marking the ends of vulcanized splices with fiduciary patches, detecting the patches, and extracting the image data containing the vulcanized splice portion of the belt located between adjacent patches.

Figure 52:
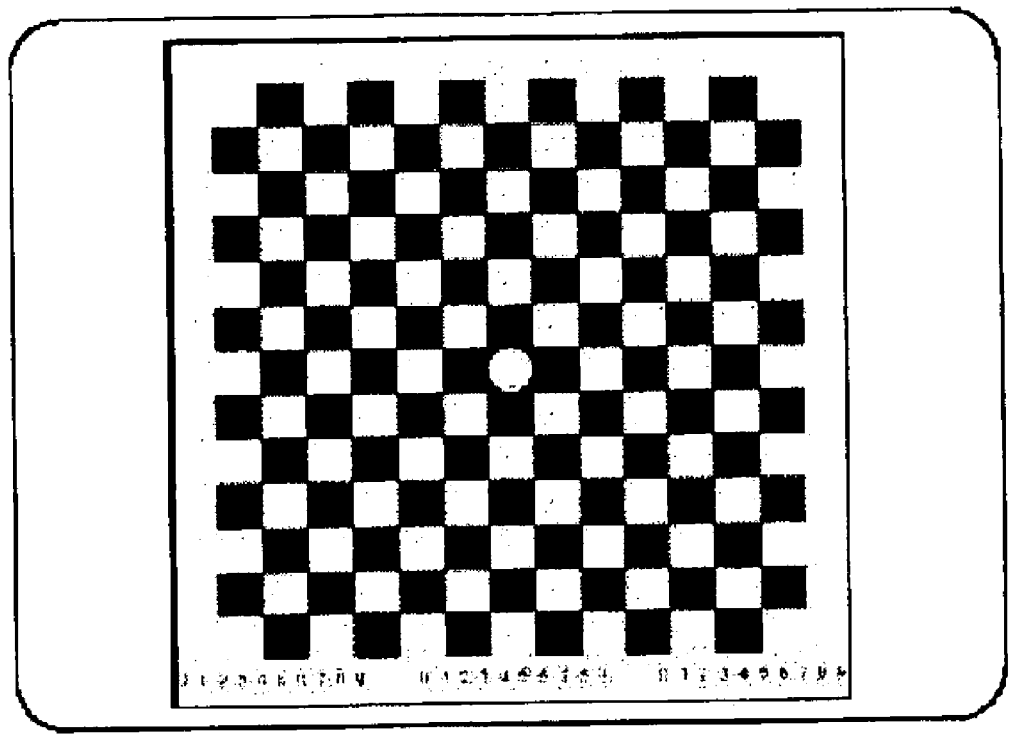
FIG. 52 illustrates one embodiment of a fiducial patch design.

FIG. 52 illustrates one embodiment of a fiduciary patch design. In this embodiment, the patch is 8 inches high by 8 inches wide and includes a checkerboard pattern centered within the patch and a circle located at the center of the patch. The checkerboard pattern is 7.5 inches per side and each checkerboard square is 0.5 inches per side.

In general, the checkerboard pattern can be easily distinguished from any other object on the belt, including the belt itself. The size of the checkerboard squares closely matches the size of a mechanical splice zipper hole width so that a single algorithm may be implemented to detect both mechanical splices and fiduciary patches. The size of the patch distinguishes the patch from a mechanical splice. The circle in the middle of the patch enables the exact center of the patch to be located in order to perform accurate measurements between patches.

Figure 53:
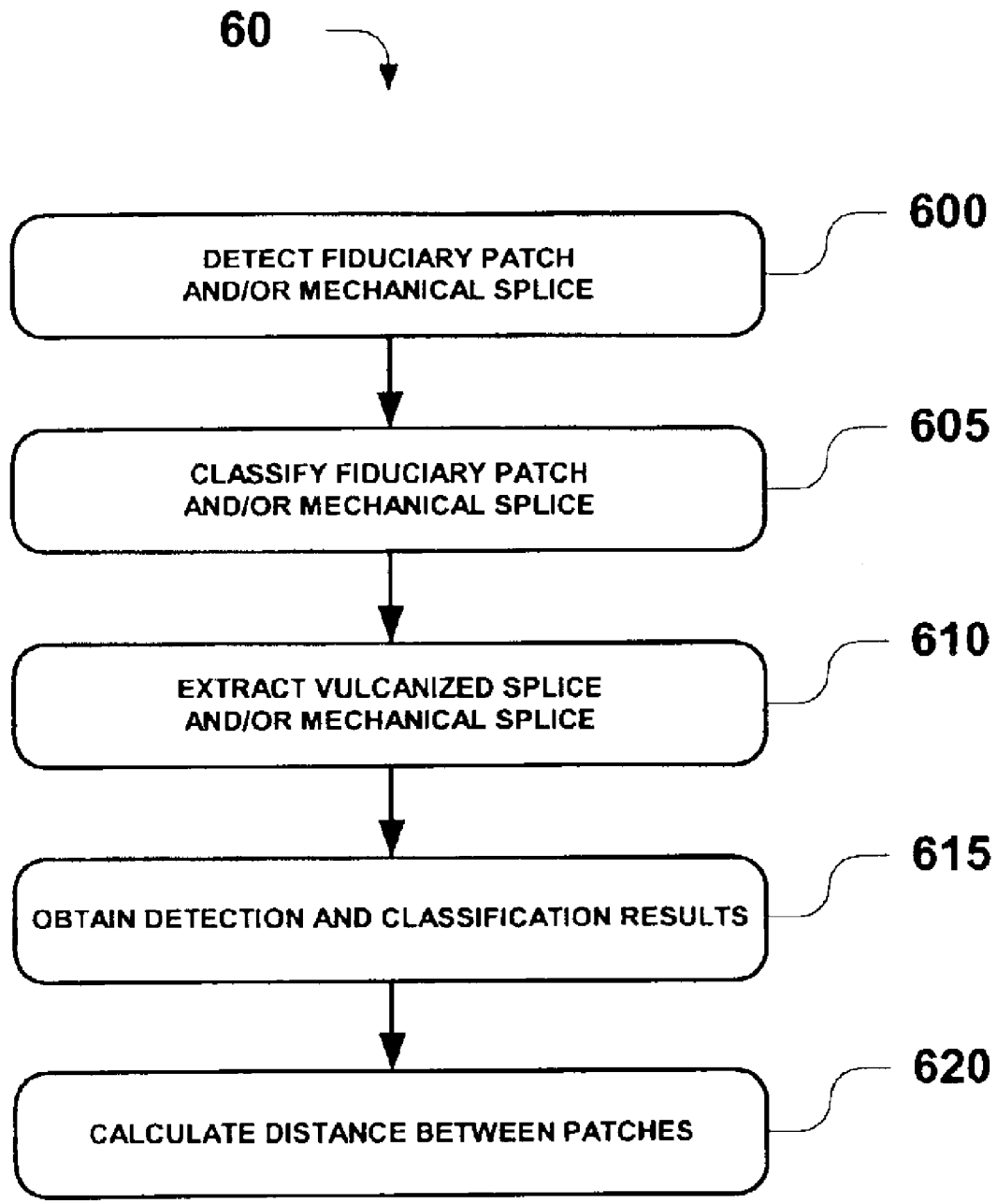
FIG. 53 illustrates one embodiment of a vulcanized splice detection algorithm.

FIG. 53 illustrates one embodiment of a splice detection algorthm 60 that may be implemented by the BIS 20. In general, the splice detection algorithm 60 may include detecting a fiduciary patch and/or a mechanical splice (step 600), classifying the fiduciary patch and/or the mechanical splice (step 605), extracting the vulcanized splice and/or mechanical splice (step 610), obtaining detection and classification results (step 615), and calculating a distance between patches (step 620). In one implementation, the splice detection algorithm 60 enables the BIS 20 to reliably detect both mechanical splices and fiducial patches (both referred to as "objects") while ignoring the rest of the belt. Once detected, the BIS 20 classifies a detected object as either a mechanical splice or a fiduciary patch.

Detecting a fiduciary patch and/or a mechanical splice (step 600) may be performed as follows. In general, the amount of strong edges concentrated in small areas within the mechanical splice and fiduciary patch make them stand out with respect to the rest of the belt. The detection algorithm 60 exploits this fact by examining the image data of the belt looking for areas of high concentration.

Figure 54:
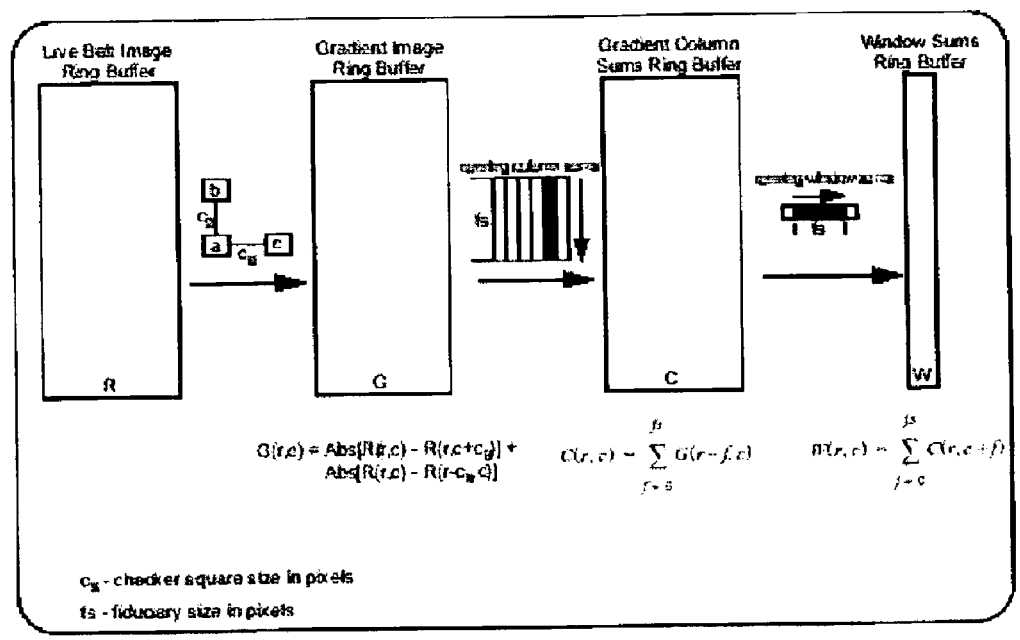
FIG. 54 illustrates one embodiment of a data structures and computation involved in computing edge score.

FIG. 54 illustrates a block diagram showing the data structures and computation involved in computing an edge score for each raw image row. The edge score is used to both detect and distinguish between the mechanical splices and the fiduciary patches.

To measure the amount of edge information contained at a particular pixel location in the raw image data, a gradient value at that pixel location is computed. The gradient score takes advantage of the fiduciary patch pattern (e.g., checkerboard pattern) in order to maximize the gradient score at a pixel that is part of the fiduciary patch. The gradient score computation is shown in FIG. 54. As new image data is captured, it is placed in the live belt image ring buffer. A gradient score is computed for each pixel of the new image data in the live belt image ring buffer and is stored in the gradient image ring buffer.

As the gradient image is computed row-by-row, a running sum is maintained for each pixel column, as shown in FIG. 54, and stored in the gradient column sums ring buffer. The size of the running column sum window is equal to the size of the fiduciary patch, therefore, each pixel in each row of the gradient column sums ring buffer is a measure of edge information, and a measure of how well that column matches the fiduciary patch pattern (e.g., checkerboard patter) on the belt over the past fiduciary patch inches.

After each row of the gradient column sums ring buffer is computed, it is processed by applying a window sum operator over the row in order to compute scores for detection and classification of mechanical splices and fiduciary patches. As shown in FIG. 54, a window the size of the fiduciary patch is passed over each gradient column sums ring buffer row. As this is done, several items are computed and stored in the window sums ring buffer for each row including the magnitude of the largest window sum, the column location of the largest window sum, and the mean window sum response for the entire row. Each row in the window sums ring buffer therefore contains the best location within the raw image data that matches the fiduciary patch pattern and a magnitude score which represents how well it matches the fiduciary patch pattern.

Figure 55:
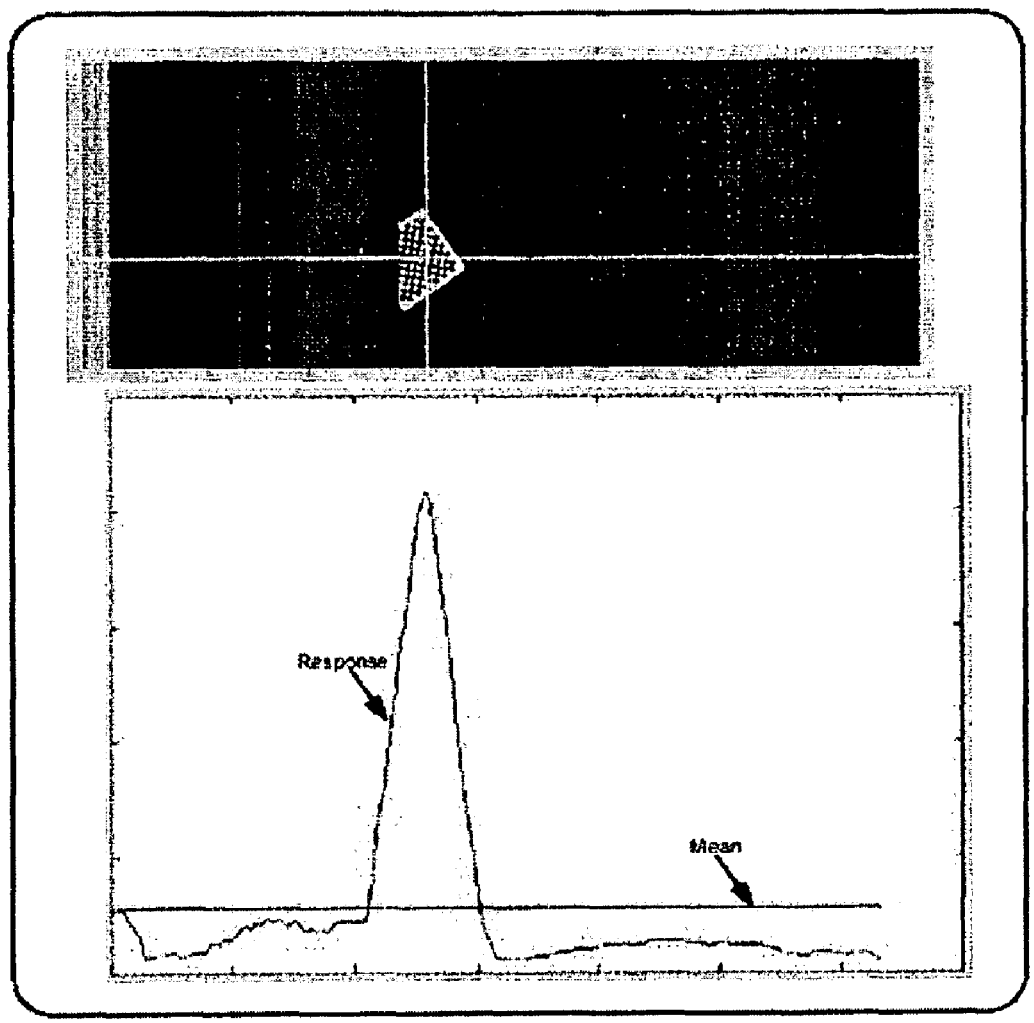
FIG. 55 illustrates one embodiment of a horizontal profile of window sums for a fiducial patch.
Figure 56:
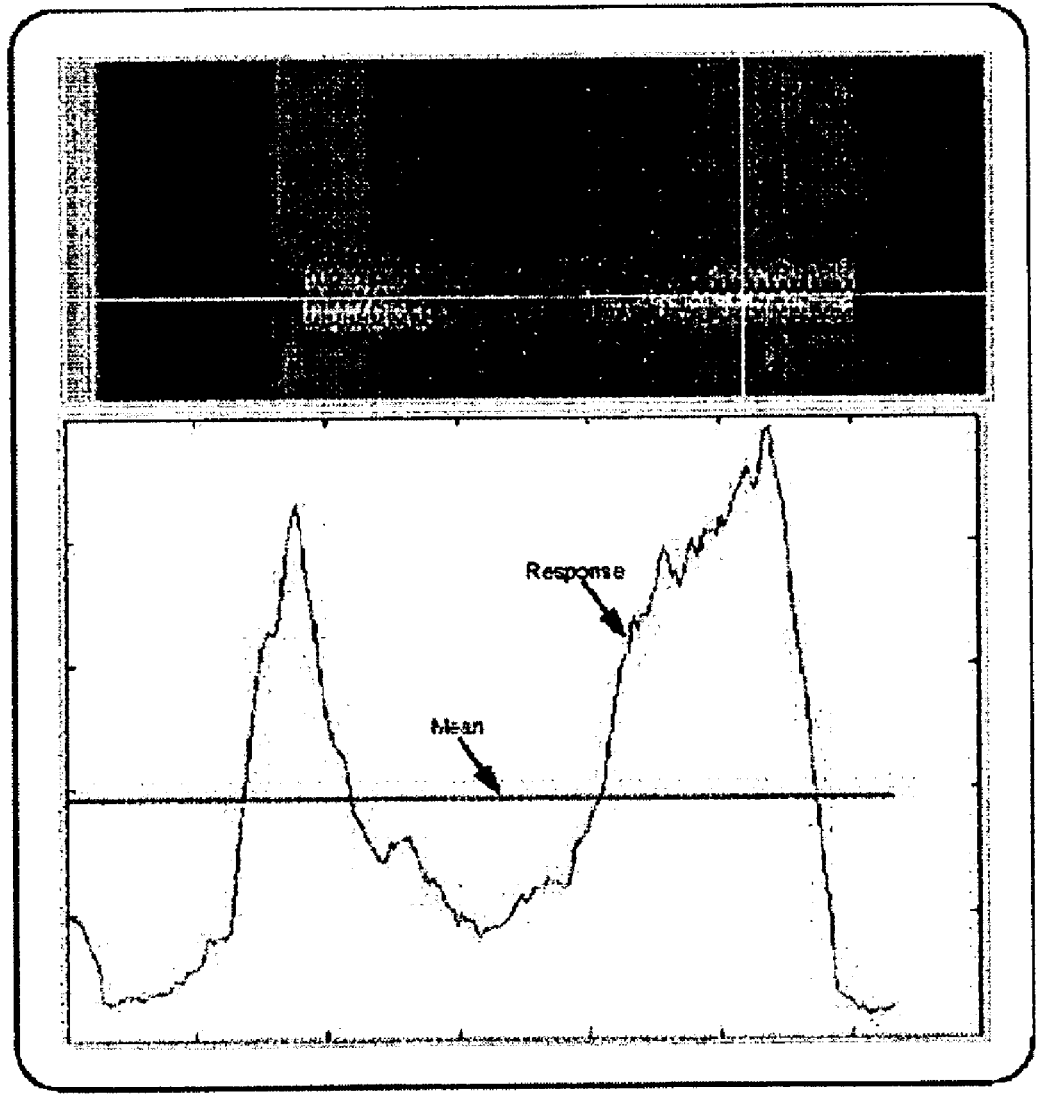
FIG. 56 illustrates one embodiment of a horizontal profile of window sums for a mechanical splice.

FIG. 55 and FIG. 56 illustrate example responses of the window sum response across a gradient column sums row for a fiduciary patch and a mechanical splice. Referring to FIG. 55, a horizontal profile of window sums for a fiduciary patch is shown. Referring to 56, a horizontal profile of window sums for a mechanical splice is shown.

As the window sums ring buffer is computed row-by-row, a running sum is maintained of the magnitude response of each row. In one implementation, the size of the running sum window may represent approximately 50 feet of belt. In general, this is large compared to the size of the mechanical splice (about 4.75 inches) or a fiduciary patch (8 inches) which allows the algorithm to compute a good average score that represents the belt. This running average score is multiplied by a user configured scaling factor in order to determine a detection threshold level.

As the window sums ring buffer is computed row-by-row, each magnitude score is compared against the running detection threshold level. If the magnitude level of a row is above the detection threshold level, it is recorded as the start of an object and an object tracking flag is set. While tracking an object, the algorithm keeps track of the row location in the live belt image ring buffer and the location within that row that produces the highest magnitude score (i.e., the location that matched the fiduciary pattern the best), which may be referred to as the center row.

Object tracking continues until a row magnitude score drops below the detected threshold. This row is recorded as the end of the object, object tracking is turned off, and object detection is completed. At this point, the object is ready to be classified and may be ready to be extracted from the live belt image ring buffer and placed into the analyzer image ring buffer queue to be analyzed.

Classifying the fiduciary patch and/or the mechanical splice (step 605) may be performed as follows. Referring to FIG. 55 and FIG. 56, it can be seen that the mean response for the mechanical splice is higher than that of the patch because the edges contained in the mechanical splice (especially those produced by the clip teeth and rivets) occupy a larger portion of the image width than those of the fiduciary patch. A classification score takes advantage of this difference by normalizing by the mean window sum response within a row and may be defined as:

Let MeanWS=Mean(WindowSum)

and MaxWS=Max WindowSum then ClassificationScore=(MaxWS−MeanWS)/MeanWS where ClassificationScore may be used to classify the detected objects as being either a mechanical splice or a fiduciary patch.

After the mean response is computed for a row in the window sums ring buffer, the classification score for the row is computed by the above formula.

As the window sums ring buffer is computed row-by-row, a running sum is maintained of the classification score response of each row. In one implementation, the size of the running window sum window is large enough to represent approximately 50 feet of belt. In general, this is large compared to the size of a mechanical splice (about 4.75 inches) or a fiduciary patch (8 inches) which allows the algorithm to compute a good average score that represents the belt and mechanical splices. This running average score is multiplied by a user configured scaling factor in order to determine a classification threshold level.

Once an object is detected, the classification scores of the rows in the window sums ring buffer between the start and end of the object are examined to determine what type of object has been detected. If the classification scores for an object are above the classification threshold level, then the object is classified as a fiduciary patch. Otherwise, it is classified as a mechanical splice.

If the object is a mechanical splice, it is ready to be extracted from the live belt image ring buffer into the analyzer ring buffer where it will be analyzed for defects. However, if the object is a fiduciary patch, the algorithm must process the patch further to determine if it is part of a vulcanized splice or point-of-origin patch pair and whether it is the head or tail patch.

If the algorithm has not detected a head patch yet, which by default it has not at the start of the application, then this patch is marked as the head patch. The next detected patch is assumed to be the tail patch and its distance from the previous patch (the head) determines how the algorithm proceeds.

The distance between the pair of adjacent patches classifies the patch pair as either the point-of-origin of the belt, a fiducial splice, or no object. The classification may be performed as follows. If the distance between the patches is less than the user defined maximum distance between the point-of-origin patches, then the patches are classified as being the point-of-origin of the belt. If the distance between the patches is greater than the user defined maximum distance between the point-of-origin patches and less than the user defined maximum distance between a pair of patches that define a vulcanized splice, then the patches are classified as being part of a vulcanized splice. If the distance between the patches is greater than the user defined maximum distance between a pair of patches that define a vulcanized splice, then the pair patch is ignored.

If the pair patch is determined to be part of a vulcanized splice, then detection of a vulcanized splice has taken place and the algorithm is ready to extract the splice from the live belt image ring buffer into the analyzer ring buffer where it will be analyzed. If the pair patch is determined to be the point-of-origin of the belt, then the algorithm informs the table of contents identification manager that the point-of-origin has been detected and of its location. Regardless of the pair patch classification, after the pair has been processed, the tail patch will become the head patch and the algorithm waits for the next patch to be detected. Once the next patch is detected, the same steps as above are performed.

Whenever a mechanical splice is detected by the system, the algorithm purges any information that is stored in the head patch data structure and clears the head patch detected flag. This is because the algorithm assumes that there cannot be a mechanical splice located between any pair of patches. In this case, the algorithm classifies the next detected patch as the head patch and again proceeds as above.

Extracting a mechanical splice and/or a vulcanized splice (step 610) may be performed as follows. Once the object has been detected and classified, the object is extracted from the live belt image ring buffer and added to the object analyzer ring buffer. The type of object determines how the image data extraction takes place.

Figure 57:
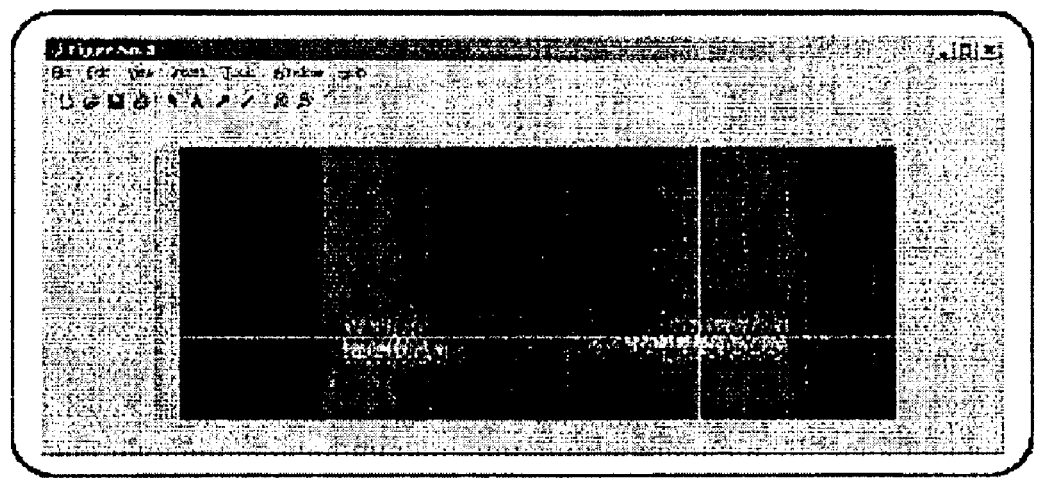
FIG. 57 illustrates one embodiment of a fiducial detector estimate of mechanical splice.

Extraction of a mechanical splice is performed by extracting the image data located around the center row location determined while tracking the object in the detection phase of the algorithm. The image data extracted may include the data located a fixed number of rows before and after the center row location so that the entire mechanical splice is sure to be captured in the extracted image data. FIG. 57 illustrates a fiducial detector estimate of mechanical splice center used to extract a splice.

Extraction of a vulcanized splice is done by extracting image data located between the head and tail fiduciary patches. The image data extracted may include data located a fixed number of rows before the center row of the head patch and after the center row of the tail patch so that the entire vulcanized splice and both fiduciary patches are sure to be captured in the extracted image data.

Figure 58:
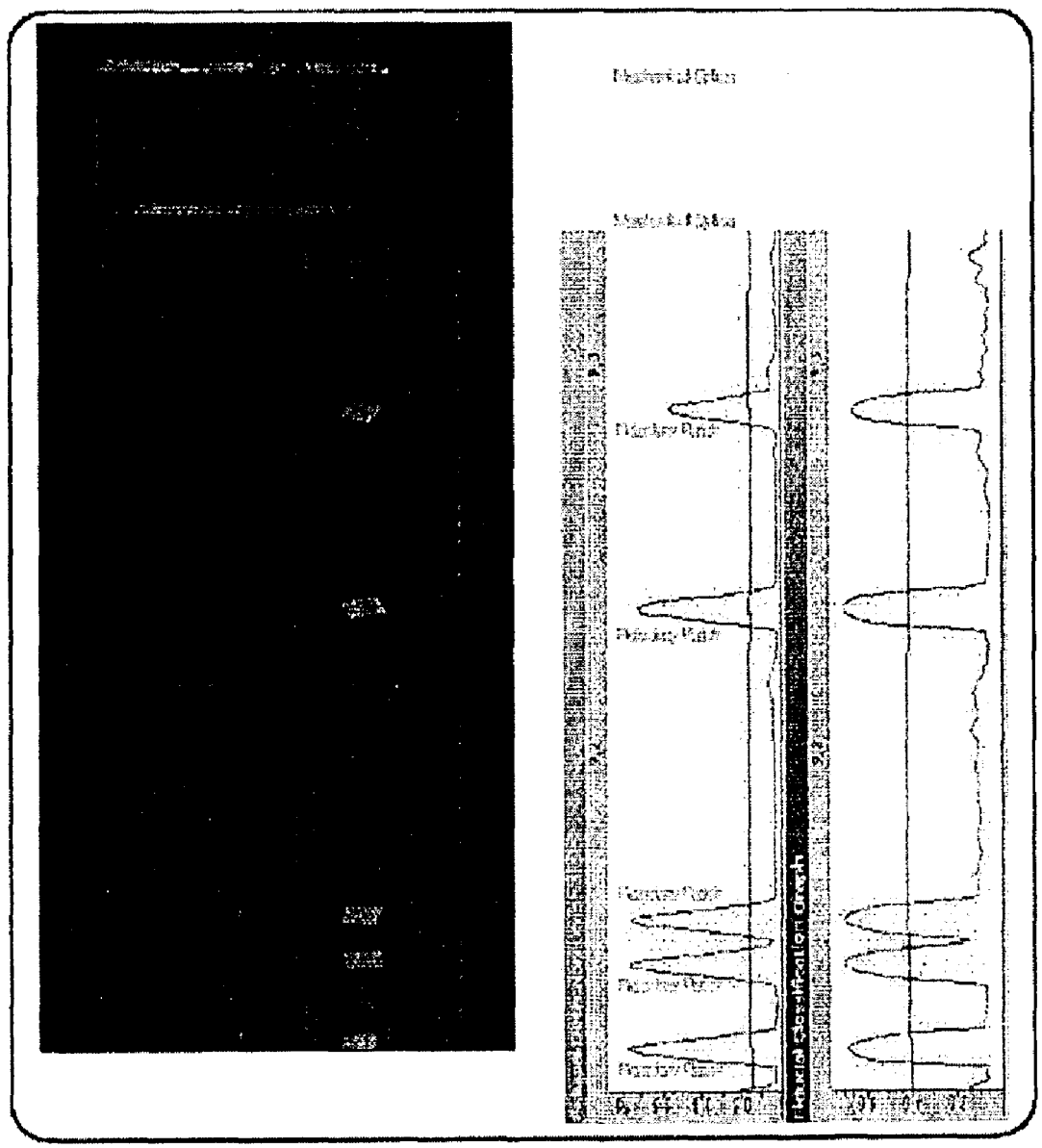
FIG. 58 illustrates one embodiment of fiducial detection and classification.
Figure 59:
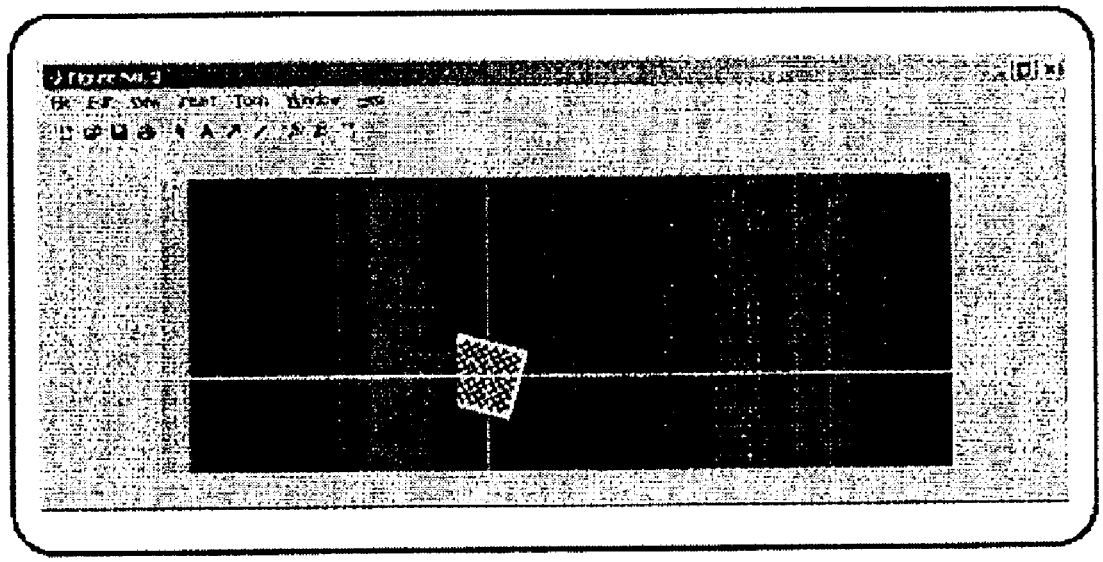
FIG. 59 illustrates one embodiment of a fiducial detector estimate.

Obtaining detection and classification results (step 620) may be performed as follows. FIG. 58 illustrates algorithm detection and classification score results for a 35-foot section of belt that contains five fiduciary patches and two mechanical splices. As shown, the detection graph window indicates the detection score response of the algorithm over the entire section of belt and the running detection threshold level. As seen in this graph, the detection score response of each one of the patches and mechanical splices is above the detection threshold level which indicates that all objects have been detected by the algorithm.

As shown, the classification graph window indicates the classification score response of the algorithm over the same section of belt as well as the classification threshold level. As seen in this graph, the classification score of each fiduciary patch is above the classification threshold level while the classification score of each mechanical splice is below the threshold level. This indicates that each fiduciary patch has been correctly labeled as a fiduciary patch while each mechanical splice has been correctly labeled as a mechanical splice.

Calculating a distance between patches (step 620) may be performed as follows. The length of a vulcanized splice is defined to be the distance between the center of the head and tail fiduciary patches that mark the boundaries of the vulcanized splice. By monitoring the length of the vulcanized splice over time, the system can determine how much the vulcanized splice is stretching. The amount of stretch can then be used as an indicator for alerting an operator (e.g., via audio or visual alarm) when a vulcanized splice may be in danger of failing so that the operator can schedule to have the splice repaired before it breaks. The following describes various methods for locating the center of the fiduciary patches and for defining the length of the splice.

In one implementation, the algorithm for detecting the center of a fiduciary patch has multiple stages including determining a detector estimate, determining a border stripes estimate, and determining the center of the circle. In general, the goal of each stage is to use the knowledge of the location estimate of the center of the patch produced by the previous stage(s) and improve upon it by detecting some other feature of the patch that helps to refine the estimate.

Obtaining a detector estimate may be performed as follows. As the window sums ring buffer is computed row-by-row, each magnitude is compared against the running detection threshold level. If a magnitude level of a row is above the detection threshold level, it is recorded as the start of an object and an object tracking flag is set. While tracking an object, the algorithm keeps track of the row location in the live belt image ring buffer and the location within that row that produced the highest magnitude score (i.e., the location that matched the fiduciary pattern the best), which may be referred to as the center row. Object tracking continues until a row magnitude score drops below the detection threshold. This row is recorded as the end of the object, object tracking is turned off, and object detection has taken place.

Obtaining a border stripes estimate may be performed as follows. In this stage, the detector estimate may be refined by finding the half-inch borders around the patch. This may be particularly useful when part of the patch is occluded, missing, or damaged. The location of the borders are used to compute the location of the center. In one implementation, obtaining a border stripes estimate includes the steps of finding the angle A of rotation and the center of mass, rotating the image of the patch by the angle A, finding a horizontal and vertical border of the rotated patch, estimating the center using the detected borders and center of mass, and rotating the center by angle—A to go back to the original image coordinates.

Finding the angle A of rotation and the center of mass may be performed as follows. When a fiduciary patch is vulcanized onto the belt, it will most likely appear at some rotated angle in the captured image data. In general this angle may be from −45 to 45°. Detecting the borders of the patch is much easier when the patch is not rotated because the borders are aligned vertically with the image columns and horizontally with the image rows. This step determines the angle at which the patch is rotated in the image in order to rotate the patch by this angle so that it becomes square with the image columns and rows.

For a fiduciary patch pattern (e.g., checkerboard pattern), the sides may produce very strong edges in the image. The edges belonging to the top and bottom and to the left and right sides of each square form two major orientation angles which are perpendicular to each other. The algorithm takes advantage of these patch properties to determine the two orientation angles using an edge angle histogram.

FIG. 60 illustrates pseudo code for computing an edge angle histogram and center of mass. The strength (or magnitude) of an angle of an edge may be computed using the horizontal and vertical gradients by using the filters illustrated in FIG. 61. As shown in the figure, a vertical gradient filter and a horizontal gradient filter may be used to compute the magnitude and angle of edges within a fiduciary patch.

Figure 62:
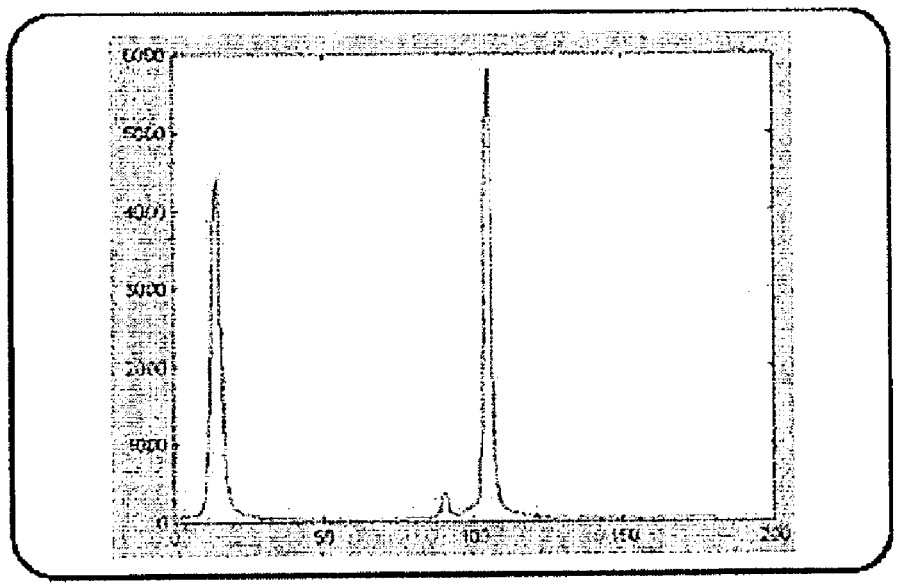
FIG. 62 illustrates one embodiment of an edge angle histogram.

FIG. 62 illustrates an edge angle histogram for the patch image. In this figure, the patch is rotated by 15 degrees which is why a peak at 15 degrees and another at 105 degrees is seen. The small peak at 90 degrees corresponds to the edge where part of the patch is torn.

Figure 63:
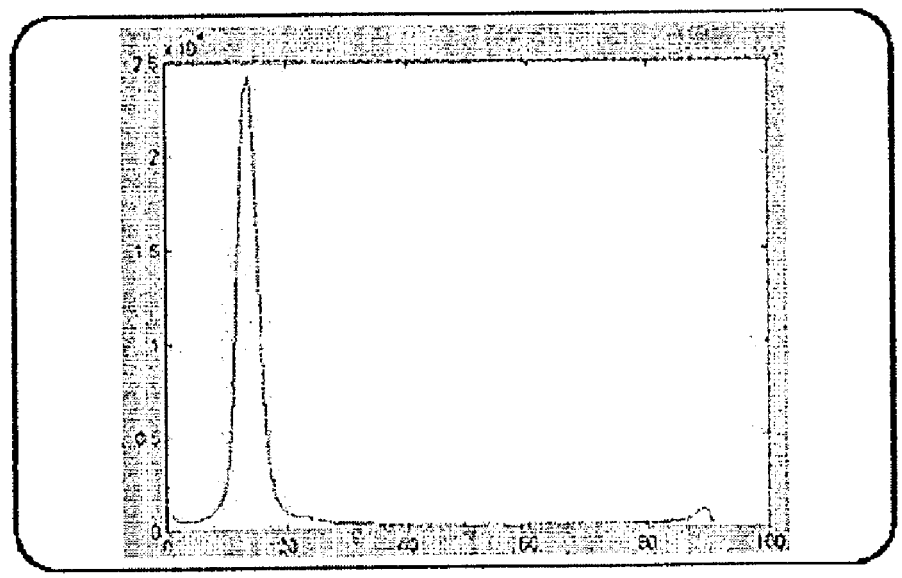
FIG. 63 illustrates one embodiment of a histogram.

Since the major angles of the fiduciary patch pattern (e.g., checkerboard pattern) are perpendicular, the two-peak histogram may be combined into a one-peak histogram as shown in FIG. 63. As shown in the figure, a histogram of perpendicular edge angles for the patch image may be obtained by adding histogram values between 0–90 with their offset counterparts between 90–180. The maximum of this one-peak histogram is the angle of rotation A.

Rotating the image of the patch by angle A may be performed as follows. Image rotation may be achieved by multiplying the image pixel coordinates with a rotation matrix:

$$\text{Coordinates} = [XY]'$$

$$\text{RotationMatrix} = [\cos(A)\sin(A)][-\sin(A)\cos(A)]$$

$$\text{RotatedCoords} = \text{RotationMatrix} * \text{Coordinates}$$

Figure 64:
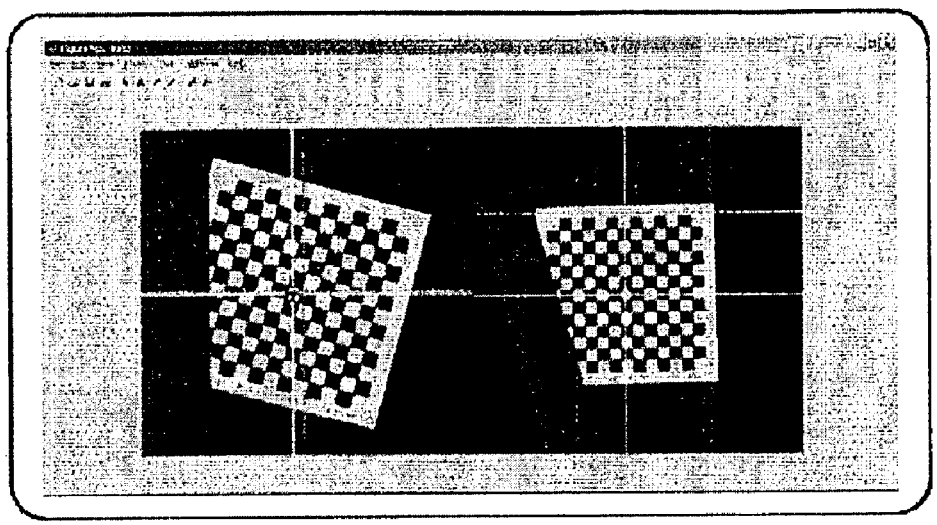
FIG. 64 illustrates one embodiment of estimating center using detected borders.

FIG. 64 illustrates a patch rotated so it is square to the image plain using the peak angle in the histogram. As shown, the center is estimated using the detected borders of the patch. On the left, the original rotated patch with the center of mass estimate is shown as dashed lines and border detector estimate of the center of the patch is shown as solid white cross-hair with small black cross. On the right, the patch rotated by a rotation angle A with detected borders is shown as dashed lines and center estimate is shown as solid white lines.

Finding a horizontal and vertical border of the rotated patch may be performed as follows. Once the patch is square on the image, the horizontal white border can be found by taking the sum of adjacent rows of pixel values (number of rows is the thickness of the stripe, about half-inch or 25 pixels high). The white border gives high values for the sum and the row where the highest sum occurred is the location of the horizontal white border. Similarly, the vertical border can be found using the same method for processing the columns of the image. Referring again to FIG. 64, the two dotted lines in the right image indicate the two detected border stripes. Only one horizontal and one vertical border are needed to locate the center.

Estimating the center using detected borders and the center of mass may be performed as follows. The center of mass computed in the first step is used to tell which quadrant the center of the patch is located with respect to the intersection point of the detected horizontal and vertical borders (point-of-origin of borders). The quadrant in which the center of the patch is located tells the algorithm how much to add/subtract from the point-of-origin coordinates of the borders in order to compute an estimate of the center of the patch. The amount to add/subtract to get the estimated center of the patch is a function of the patch dimensions. In cases where the current patch pattern is a square, half the size of the patch is the correct amount to add/subtract to the point-of-origin of the detected borders.

Referring again to FIG. 64, the dotted cross-hair in the left image shows the computed center of mass. Using the two detected border stripes (dashed lines in right image) and the center of mass, the center of the patch can be projected by adding half the height of the patch and subtracting half the width of the patch to get an estimate of the center of the patch row and column location (white cross-hair in right image). In cases where there is partial occlusion of the patch, the method can be very effective in locating a fairly accurate estimate of the center of the patch.

Rotating the center by angle −A to go back to the original image coordinates may be performed as follows. The found center is still in the rotated coordinates. The center is returned to the original coordinates by rotating the estimated center coordinates in the opposite direction given by the rotation angle −A.

After obtaining the border stripes estimate, the location estimate of the center of the patch may be refined further by detecting the center of the circle. The circle in the middle of the fiduciary patch marks the exact center of the patch. Detecting the center of the circle may be performed as follows. In one implementation, different algorithms may be used to search a small area around the border stripes estimate from the previous stage to look for the circle and its center. For example, one algorithm that may be used is based on binary image morphology. Another algorithm that may be used employs template matching to detect the center of the circle.

The binary morphology center of circle detection method may locate the center of the circle by binarizing the image, dilating the binary image, labeling the connected components, and finding the connected component which matches the area of the circle.

To binarize the image, a small image area around the border center estimate is extracted. A histogram of the pixel intensities of the sub-image is computed. The histogram is then searched for a pixel intensity threshold level to use to convert the gray-scale image into a binary (black/white) image so that roughly 60% of the pixels will be binarized to black and 40% to white. This percentage is exemplary only and is based on the fiduciary pattern design of black and white squares and the fact that the border center estimate will be located on the patch. Therefore, ideally the percentage split should be 50-50 but using the split as 60-40 allows for occlusions. Determining the threshold level in this manner makes it dynamic. That is, the threshold level is insensitive to lighting conditions. Alternatively, the threshold could be set as the mean gray value of the sub-image.

Figure 65:
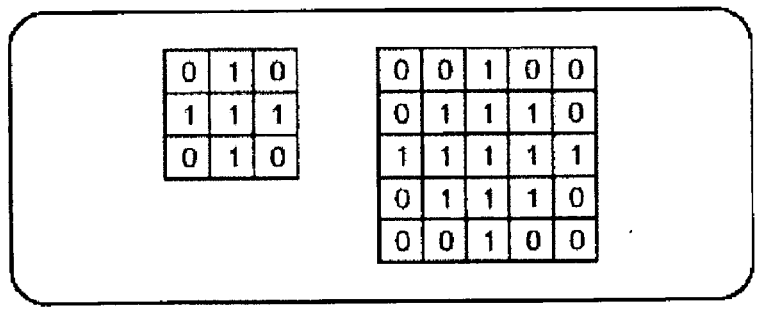
FIG. 65 illustrates one embodiment of binary image morphology.

FIG. 65 illustrates locating the center of the circle using binary image morphology. Image a is a binarized image of Image c. Image b shows connected components. Image c shows center of mass of circle (black cross-hairs) location drawn on top of the original fiduciary patch image.

Figure 66:
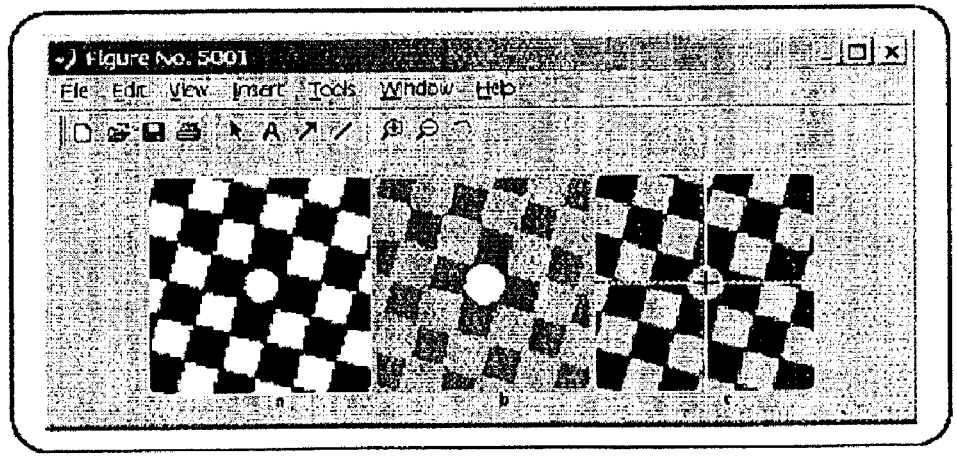
FIG. 66 illustrates one embodiment of a dilation operation.

To dilate the binary image, each white pixel in the binary image is grown using a diamond structuring element. FIG. 66 illustrates one embodiment of a structuring element used in dilation operation. As shown, the origin is the center pixel.

The purpose of dilation is to connect all the white squares to each other (making them one big connected component) while leaving the white circle unconnected to any other white object. The diamond shape may be used because it does not allow the circle nor the corners of the neighboring squares to grow toward each other. To further insure that all of the squares are connected, a one-pixel-thick white line may be placed at the binary image border before dilation.

To label the connected components, adjacent white pixels may be lumped together once the sub-image has been dilated. In one implementation, an 8-connectivity operator may be used to form a list of connected components of the image. Referring to Image b of FIG. 65, the dilated image of binary Image a is shown, where all of the connected components are designated as different gray-scale values. It should be noted that the squares connect to each other, while the circle is isolated.

To find the connected component which matches the area of the circle, the area of each connected component may be examined to determine if the circle is present in the sub-image. In one implementation, the imaging resolution of the system is 50 pixels/inch. At this resolution, the algorithm expects the half-inch circle to have a radius of 12.5 pixels in the image. When dilated using a 3×3 structuring element, the radius grows to 13.5, thus the expected circle area becomes 573 pixels (PI*Radius=3.14*13.5).

The area of each connected component is computed and compared against the expected circle area. A connected component is labeled as a circle if its area is within some range of the expected area of the circle. In one embodiment, the error range may be +/−150 pixels. If multiple connected components are labeled as circles or if no connected component is labeled as a circle, then the algorithm returns the border center estimate as the estimate of the center of the patch.

To compute the center of mass of the circle, the center of mass of the connected component labeled as a circle gives an estimate of the center of the circle and thus the center of the patch. The center of mass of the circle may be computed by averaging the row and column coordinates of each of the pixels in the connected component list of the circle. The center of mass coordinates of the circle are then returned as the refined estimate of the center of the fiduciary patch. Referring to FIG. 65, Image c shows the original sub-image. The dotted cross-hair is the estimate from the previous stage and the solid white cross-hair (with the black center cross) is the circle center of mass estimate of this stage.

Another algorith for detecting the center at the circle may use template matching. In one implementation, the template matching center of circle detection method may be performed by binarizing the image, convolving a template over the image, and evaluating template matching scores. In general, binarizing the image may be performed as described above.

Figure 67:
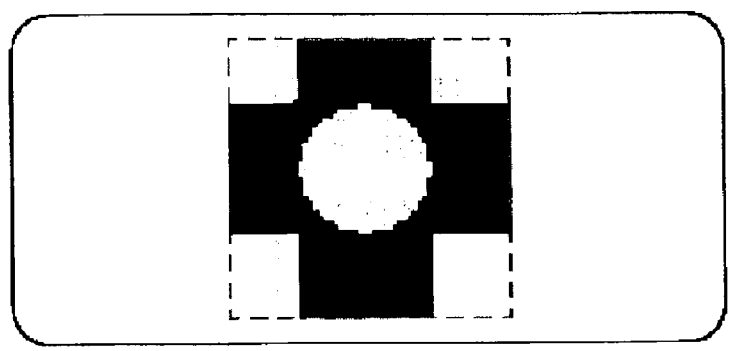
FIG. 67 illustrates one embodiment of a circle template.

To convolve a template over the image, a template image pattern is convolved over the binary sub-image. The result of this step is a sub-image with pixel scores that represent how well that pixel location matches the template image. FIG. 67 illustrates an example of a circle template. As shown, dashed lines represent borders of the template.

To evaluate template matching scores, the best matching template location is found within the template matching score image. The highest score represents the best matching location. To determine if the center is present at this location, the template matching score is compared against a matching threshold. The matching threshold is selected such that the template matching score at this location must match the template by at least 50%, that is, if the template is 40×40 pixels in size, then the score must be at least 40×40 0.5=800.

If the score is above the threshold level, then this location is returned as the refined estimate of the center of the fiduciary patch. Otherwise, the estimate of the previous stage is returned.

Figure 68:
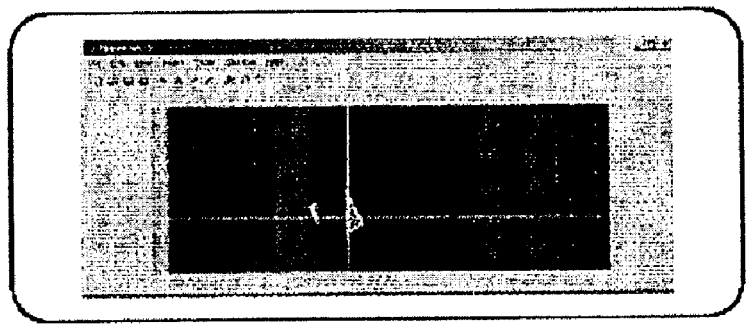
FIG. 68 illustrates one embodiment of a fiducial algorithm.
Figure 69:
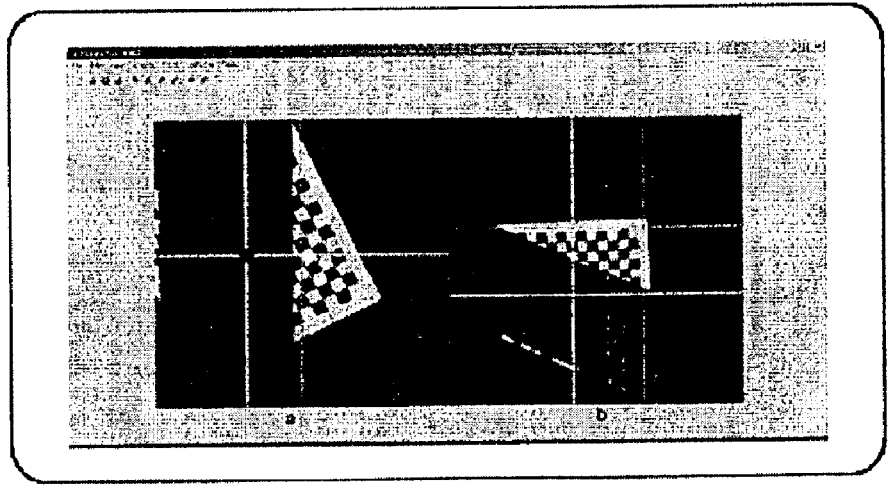
FIG. 69 illustrates one embodiment of locating the center of a fiducial patch.

FIG. 68 illustrates an example of the fiducial algorithm detecting a highly-occluded fiduciary patch. FIG. 69 illustrates an example of the center of patch detector locating the center of the patch. In this case, the circle of the patch is occluded and the center of the patch is the estimate by the border detector stage.

In one implementation, the BIS 20 may perform object identification. The BIS 20 may perform such object identification as part of, in addition to, and/or independent of performing splice detection.

Each belt in a mine may contain any number of objects where an object may be a mechanical or vulcanized splice, a whole, a flapper, etc. The number of objects and their location on a belt may be unique to each belt. The BIS 20 may track each object and its location on the belt by assigning each detected object a unique identification tag. Techniques for assigning identification tags and tracking objects are discussed below.

In one implementation, object identification may include manual object configuration. In general, a user may specify the number of occurrences of a particular object on the belt which would be deemed the reference object. The first object of this type detected by the system would act as the point-of-origin on the belt and all object indexes would be assigned identification tags with respect to this origin.

Assuming good object detection, object identification tags may be assigned to the running count of each individual object. When the referenced object has been detected for the user configured number of times, all counts would reset so that all of the objects would maintain the same identification tag with respect to the point-of-origin.

In implementation, the user may have the choice of setting either the number of mechanical or vulcanized splices on a particular belt, for example. The first reference object detected by the system is deemed the point-of-origin on the belt and all object identification tags are with respect to that point-of-origin object. Once the point-of-origin is detected, each object type receives an identification tag in sequential order. Every time the reference object has been detected for the user configured number of times, all counts are reset and the detected objects on the current belt revolution will again receive identification tags in sequential order.

If the BIS 20 includes an encoder, then the BIS 20 may position stamp the location of each object. This information may be used to track each object through the graphical user interface display as to the distance the object is from the BIS 20 and to estimate the amount of time before the object is back at the BIS 20 at the current belt speed.

In one implementation, object identification may include installing a fiduciary point-of-origin on the belt. For example, a fiduciary point-of-origin can be installed on each belt to act as the zero reference point of the belt. The system may detect the point-of-origin and use it to assign identification tags to each object that is detected on the belt. Each object type may receive an identification tag in sequential order with respect to the reference point which would uniquely identify the object.

In implementation, detected objects may receive a valid identification tag after the point-of-origin is detected. Once the point-of-origin is detected, each object type receives an identification tag in sequential order. Every time the point-of-origin is detected, the object identification tag numbers are reset and the detected objects on the current belt revolution will again receive identification tags in sequential order.

If the BIS 20 includes an encoder, then the BIS 20 may position stamp the location of each object. This information may be used to track each object through the graphical user interface display as to the distance the object is from the BIS 20 and to estimate the amount of time before the object is back at the BIS 20 at the current belt speed.

In one implementation, object identification may include using a belt pattern. In general, the distances between objects on a belt are not uniform in length. Assuming good object detection, the BIS 20 may use the pattern of belt lengths to uniquely identify objects after a couple of loops of the belt. Table 1 shows an example of using a belt pattern. The numbers in the table correspond to distances between detected objects on a belt. After the pattern repeats for a number of cycles, the pattern can be detected and used to assign unique identification tags to the objects according to the pattern.

TABLE 1

| Object Type | Distance from Previous Object | ID |
| --- | --- | --- |
| vulcanized splice | 400 | unknown |
| mechanical splice | 500 | unknown |
| mechanical splice | 450 | unknown |
| vulcanized splice | 475 | unknown |
| — | — | — |
| vulcanized splice | 400 | V1 |
| mechanical splice | 500 | M1 |
| mechanical splice | 450 | M2 |
| vulcanized splice | 475 | V2 |

In one implementation, object identification may use a 2-length algorithm. An object such as a splice, for example, joins two pieces of rubber together to make up part of the belt. Given an accurate encoder measurement of belt position, good object detection, and a belt assembled from non-uniform lengths of rubber, two lengths may uniquely define each object. Table 2 an example of using a 2-length algorithm. The distance each object is from its neighbor object is used to determine the object pattern on the belt. After the pattern repeats for a number of cycles, the pattern can be detected and used to assign unique identification tags to the objects according to the pattern. It should be noted that this algorithm can be extended to look at N-neighbors which would make the pattern detection more robust and could also allow the algorithm to detect objects being added or removed from the belt and to handle false object detection problems.

TABLE 2

| Distance to Previous Object | Object Type | Distance to Next Object | ID |
| --- | --- | --- | --- |
| 400 | vulcanized splice | 500 | unknown |
| 500 | mechanical splice | 450 | unknown |
| 450 | mechanical splice | 475 | unknown |
| 475 | vulcanized splice | — | unknown |
| — | — | — | — |
| 400 | vulcanized splice | 500 | V1 |
| 500 | mechanical splice | 450 | M1 |
| 450 | mechanical splice | 475 | M2 |
| 475 | vulcanized splice | — | V2 |

In one implementation, object identification may include object image correlation. In general, object imagery does not change drastically between successive collected images. Assuming the images are consistent enough, image correlation could be used to compare new images against previously collected images. High correlation scores could be matched and identification tags would be assigned appropriately.

In one implementation, object identification may include using belt and/or splice width. The mechanical splice images collected generally do not have uniform widths of belt or clips. Often, the splice installation procedure includes trimming the belt to prevent catching an edge on the belt support structure. Assuming the widths of the trimmed belt and splices are unique enough, these numbers could be used to identify a splice.

In one implementation, object identification may use object analysis results. The system is scoring each of the detected objects, that is, assigning a health score to each object and recording the location and type of defects. Knowing the "fingerprint" of each object will add to the unique identification of a particular object. For example, a new detected mechanical splice with zero missing clips could not be confused with a previously collected mechanical splice that had four missing clips.

Figure 70:
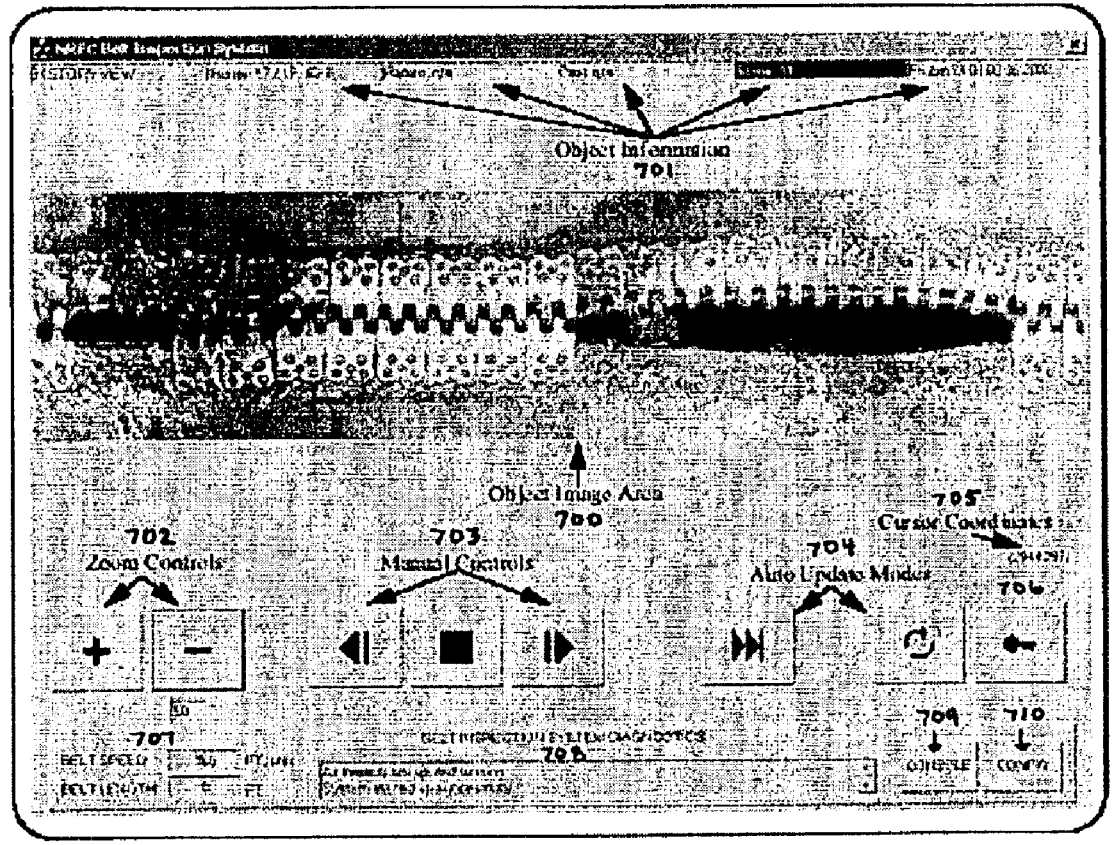
FIG. 70 illustrates one embodiment of a graphical user interface.

FIG. 70 illustrates one embodiment of a Graphical User Interface (GUI) 70 that may be displayed by the BIS 20. The GUI 70 may be presented to a user through the UI 213 and/or on a remote device, for example. In general, the GUI 70 may be used to control, display and/or algorithm variable settings.

As shown, the GUI 70 includes an object image area 700 for displaying the objects detected by the system. The GUI 70 also includes object information fields 701. In general, the object formation fields 701 may provide various pieces of information about the object currently being displayed in the object image area 700.

In one implementation, the object information fields 701 may include an image and ID field that states the current object number being displayed, the total number of objects that have been detected by the system, and/or the identification tag assigned to the current object being detected. The object information fields 701 also may include a return field informing the user how many feet and how much time at the current belt speed before the current object being displayed gets back to the BIS 20. The object information fields 701 may include a past field informing the user how many feet past the BIS 20 the current object being displayed is located. The object information fields 701 further may include an analyzed score field informing the user of the analyzed results for the current object being displayed. The object information fields 701 may include a time field informing the user of the date and time the current object being displayed was detected by the system.

The GUI 70 may include zoom controls 702. In general, the zoom controls 702 enable a user to zoom in and out on the object being displayed by using the plus/minus buttons. In one implementation, the maximum zoom in level is 400% and the out level is 25%.

The GUI 70 also may include manual controls 703. In general, manual control of viewing detected objects is provided to the user through the previous and next buttons. The next button will go to the next detected object and the previous button will go to the previous detected object. How far a user may go back may be limited to the number of items in the loop length which is defined in the general tab. If the loop length is 100 and the total number of objects being displayed is 1000, for example, then the system may only allow the user to view objects 900–1000.

The GUI 70 may include auto update modes 704. In one embodiment the user may enable one of two possible auto update modes by clicking on either the current or loop button. When active, the buttons will appear pushed in. To disable either of the auto modes, a user can click the button again so it appears pushed out, or click on the stop, next, or previous button. The current mode, when enabled, automatically updates the object image and information area with the most recent detected object information. In one implementation this may occur at a rate of once every four seconds. The loop mode, when enabled automatically loops over a list of previously detected objects. The amount of objects to loop over and how long to wait before going to the previous object can be set under the general tab. When the end of the loop list is encountered, the system may automatically jump to the most recent detected object and again may start looping back to previously detected objects.

The GUI 70 includes cursor location 705 informing the user where the cursor is located within the object area. The cursor location 705 may be used to, for example, measure features within the object image.

The GUI 70 may include a lock mode 706. The user may enable the lock mode 706 to indicate to the BIS 20 that only images of the current object being displayed are to be viewed. If the user clicks the previous or next button, or has current or loop mode enabled, the object image and information areas will be updated only with previously detected occurrences of the same object that is being displayed. Viewing multiple images of a displayed object may be used to monitor the rate of degradation of an object. In one implementation, multiple images of the same object may be viewed as a movie, for example, showing changes in the object over time.

The GUI 70 also may include belt information fields 707 and a diagnostic display area 708. The belt information fields 707 may display the current belt length and speed. The diagnostic display area 708 may display status information as to the state of the system and any errors that have been encountered.

The GUI 70 may include a console button 709 and a configuration button 710. The console button 709 may open a main console window including error and debug information logged by the BIS 20. The configuration button 710 allows a user to determine how various algorithms work, which algorithms to run, and how to display objects on the screen. The user may view or change these settings by either clicking on the configuration button 710 or by pressing the F2 function key.

Figure 71:
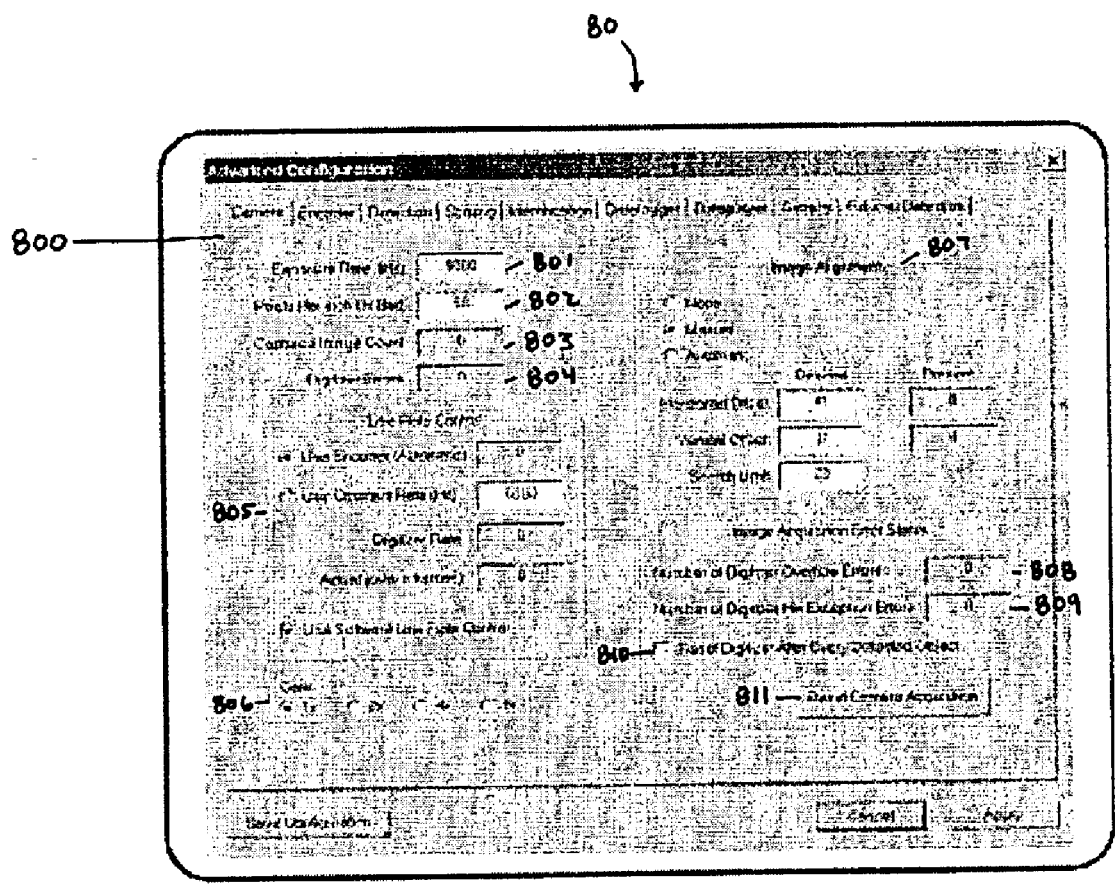
FIG. 71 illustrates one embodiment of a camera configuration interface.

FIG. 71 illustrates a configuration interface display 80 that may be implemented by the BIS 20. In general, there are numerous configuration settings that allow the user to determine how various algorithms work, which algorithms to run, and/or how to display items on the screen. As shown, the configuration interface display 80 includes a camera configuration tab 800 for configuring various camera settings.

In one implementation, the camera configuration tab 800 includes an exposure rate field 801. This field may control the amount of time the pixels are exposed to the light in order to gather information of the scene being analyzed and/or controls the shutter speed of the cameras. In one implementation, this field is in Hz or 1/seconds. In general, this value should be as fast or faster than the maximum digitizing rate that the BIS 20 is likely to use on any given belt. This will allow one setting to be used over all belt speeds which will make the lighting exposure independent of belt speed. This value, generally should not be set to a value lower than the digitizing rate.

The camera configuration tab 800 also may include a pixels per inch on belt field 802. This field may be configured by the user for every installed system to the number of pixels per inch that the system is seeing at the current installation height. This variable generally is dependent on the height the cameras are from the belt, the resolution of the cameras, and the focal length of the lens being used in the system.

One way to determine this value is to have a system detect a mechanical splice and then measure the width of a clip in the object viewing area. The value is obtained by taking the measured width of one of the clips in the splice that was detected and dividing the pixel width by the true width.

The camera configuration tab 800 may include a captured image count field 803. This field may represent the number of captured frames that have been captured by the digitizer card and have been sent to the BIS 20 to be processed since the start of the application. In general, this field provides a status to make sure the system is capturing images properly.

The camera configuration tab 800 also may include a digitizer errors field 804. This field may represent the number of reported digitizer API function call errors since the start of application.

The camera configuration tab 800 may include a line rate control field 805. In one implementation, the line rate or digitizing rate at which the BIS 20 captures lines of data from the cameras may be controlled such that it is computed in one of two modes. A use encoder (automatic) mode, when enabled, computes and sets the digitizing line rate based on the current measured speed of the belt and the value of pixels per inch on the belt by multiplying the belt speed (in/sec) by pixels per inch on the belt.

The text field next to this mode may inform the user of the digitizing rate that is computed and required. It should be noted that when the belt changes speed, there is a time delay before this is sensed by the system and the speed of the belt and thus the digitizing rate is updated. In one implementation, every time a new digitizing rate is computed, it is compared to the current setting and if it is different by more than 200 Hz, then the new rate is requested. Otherwise, it is ignored. This is because every time a new rate is requested, the system must stop digitizing, set the new rate, and then restart digitizing. During this time, a portion of the belt is not imaged by the system and thus objects may not be detected.

A use constant rate mode, when enabled, sets the digitizing line rate to the constant rate set by the user in the constant rate field. In one implementation, two status fields allow the user to view the current digitizing rate settings. A digitizer rate field displays the rate at which the software system has requested the digitizer card to capture data. The actual rate field displays the rate at which the application is actually receiving data from the digitizing card. This rate may be measured over a 30–60 second timeframe so there is some lag between this and the digitizer rate when a new rate is set.

In one embodiment, the user also may enable control of the line rate regardless of which mode the user has selected. This may be accomplished, for example, by checking the use software line rate control. When enabled, the digitizing card is directed to digitize at 9000 Hz continuously. The digitizing rate computed by the encoder mode is then used to sub-sample the captured data in order to build an image of non-overlapping and continuous belt.

In this mode, there will be a small amount of lag time between updating new digitizing rates based on the speed of the belt changing (which will make the objects being captured appear slightly distorted when the belt is speeding up or slowing down) but no pieces of the belt will be missed because the digitizer is not being stopped, programmed, and restarted over and over. Instead, the software sub-sampling rate simply changes. For example, if the encoder mode calculates a digitizing rate of 4500 then the sub-sampling routine will extract every other line from the data captured by the digitizing card and build a frame up data from it before handing it to the rest of the application to process.

The camera configuration tab 800 may include a gain field 806. This field may allow the user to select different camera gain values. In one implementation, the camera gain values may range from 1× to 8×. It should be noted that changing the gain will make the captured image data appear brighter at the cost of adding some noise to the data and at the cost of loosing some dynamic range of intensities.

The camera configuration tab 800 may include an image alignment field 807. In one implementation, the BIS 20 may include two cameras, each of which captures 2048 pixels of image data per line. This data is combined by the digitizer to make it seem like it is coming from one 4096 pixel resolution camera. In order for the image data to appear smooth, the data in the overlapping areas from the two individual cameras must be aligned.

Alignment may be performed in one of two modes. In a manual mode, the BIS 20 is informed to align the images by applying the offset values configured in the horizontal and vertical offset fields. In the automatic mode, the BIS 20 uses automated software in order to align the images. The offset values configured in the horizontal and vertical offset fields are used as an estimate of the true alignment values and the automated software searches an area, given by the search limit field, around these offsets to refine the alignment values to use on a per detected object basis.

The camera configuration tab 800 may include a number of digitizer overflow errors field 808. This is a status field that represents the number of digitizer overflow errors that have been reported to the application by the digitizer since the start of the application. Each error causes the system to stop and restart acquisition in order to resynchronize with the cameras during which time image data of the moving belt will be missed and thus objects may not be detected.

The camera configuration tab 800 may include a number of digitizer hardware exception error fields 809. This is a status field that represents the number of digitizer hardware exception errors that have been reported to the application by the digitizer since the start of the application. Each error causes the system to stop and restart acquisition in order to resynchronize with the cameras during which time image data of the moving belt will be missed and thus objects may not be detected.

The camera configuration tab 800 may include a reset digitizer after every detected object field 810. If enabled, the BIS 20 may reset the digitizer every time an object is detected during which time image data of the moving belt will be missed and thus objects may not be detected during this time. This mode may temporarily fix cameras having synchronization problems.

The camera configuration tab 800 may include a reset camera acquisition button 811. If the camera data appears to be out of synchronization, the user may manually instruct the system to reset the digitizer by clicking this button.

Figure 72:
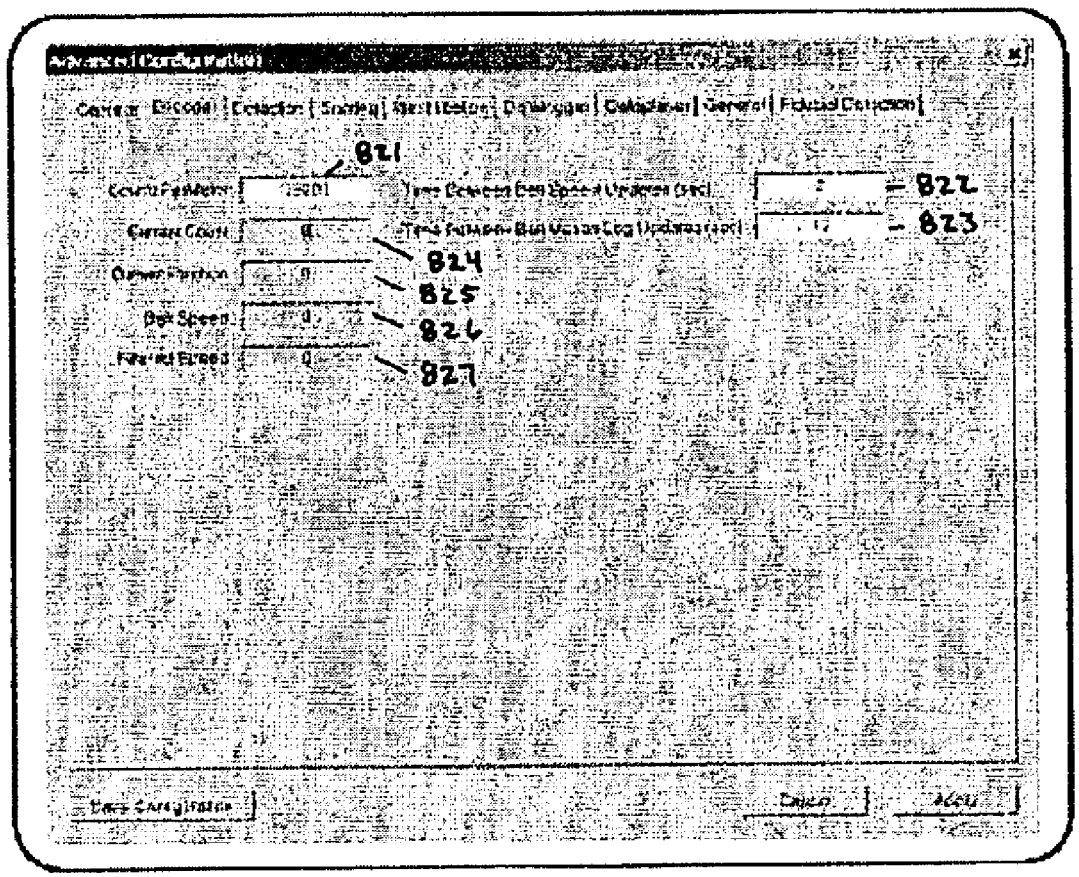
FIG. 72 illustrates one embodiment of an encoder configuration interface.

FIG. 72 illustrates an encoder configuration tab 820 that may be implemented by the BIS 20. In general, the encoder configuration tab 820 may be used to control various encoder settings.

As shown, the encoder configuration tab 820 may include a counts per meter field 821. This field represents the number of encoder counts per meter of travel. In general, this field must be calibrated and set by the user for every installation of the BIS 20.

The encoder configuration tab 820 may include a time between belt speed updates field 822. This variable represents how often the system computes a new belt speed. For example, if this variable is set to the number 3, then every 3 seconds the system computes a new belt speed. In general, the amount of time between speed updates should be as small as possible while maintaining stability of the computed speed. If the time between speed updates becomes too small, the speed of the belt will show large variations and the time between updates should be increased. In practice, a reasonable amount of time between speed updates may be around 0.5 seconds.

The encoder configuration tab 820 may include a time between belt motion log updates field 823. While the BIS 20 is running, it logs to disk the speed of the belt. This variable represents how often to log the speed of the belt to disk.

The encoder configuration tab 820 may include a current count field 824. This variable represents a current encoder count that the encoder counter card is keeping track of internally. The encoder configuration tab 820 may include a current position field 825. When the BIS 20 starts running, it starts to integrate the encoder counts received from the encoder counter card in order to generate a belt position. This variable represents the current belt position since the system started running. The encoder configuration tab 820 also may include a belt speed field 826 indicating the most recent computed speed of the belt and a filtered speed field 827 for displaying a filter speed.

Figure 73:
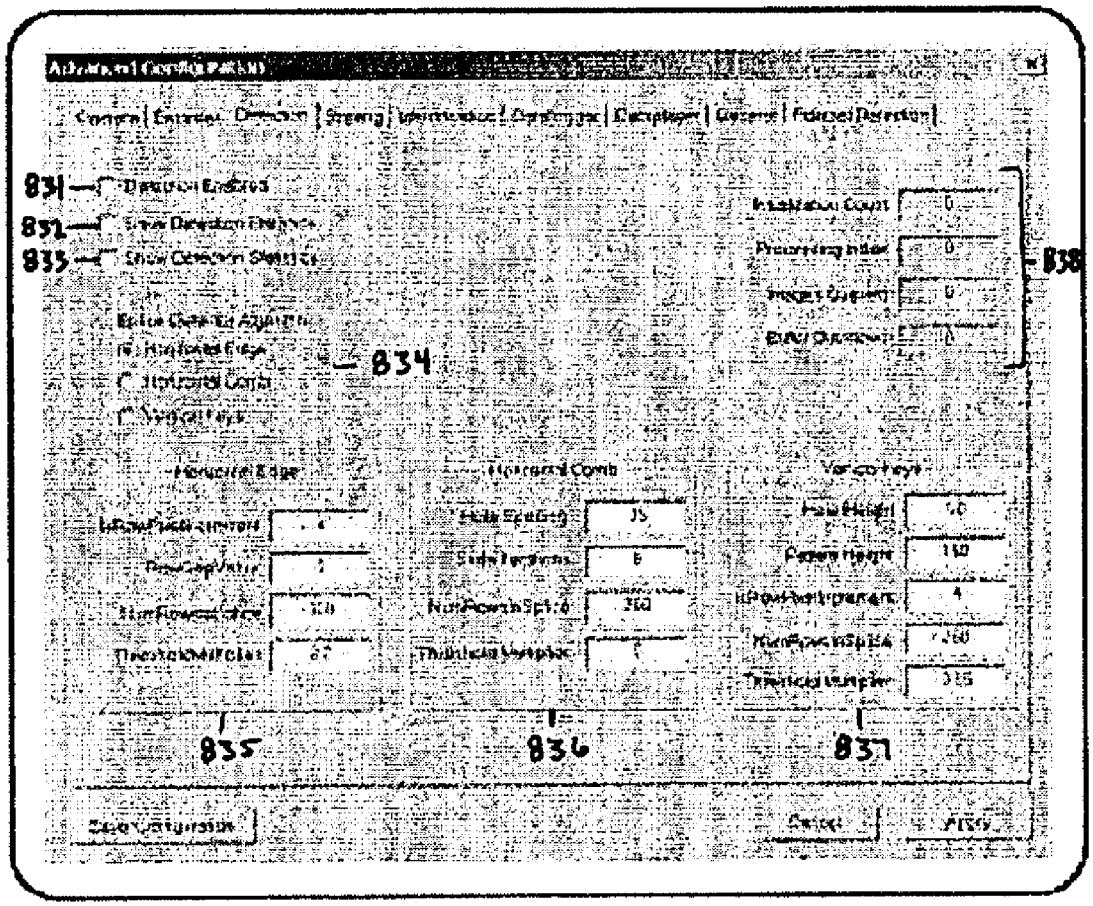
FIG. 73 illustrates one embodiment of a mechanical splice detection configuration interface.

FIG. 73 illustrates a mechanical splice configuration tab 830 which may be implemented by the BIS 20. In general, the mechanical splice configuration tab 830 allows a user to configure various mechanical splice detection settings.

As shown, the mechanical splice configuration tab 830 may include a detection enabled field 831. If this box is checked, mechanical splice detection is enabled. If this box is not checked, mechanical splice detection is disabled.

The mechanical splice configuration tab 830 may include a save detection statistics field 832. If this box is checked, then the mechanical splice detection algorithms will save information to disk while they run. In general, this may slow down the detection algorithms, but may be useful in debugging the algorithms off line by processing the logged data in the event that mechanical splices are not being detected.

The mechanical splice configuration tab 830 may include a show detection statistics field 833. If this box is checked, a graph window may appear on the screen. The graph may show the processing scores of the image data and the current mechanical splice threshold level. By inspecting the graph as the system runs, an appropriate threshold multiplier level may be set that is significantly above the background belt score and low enough to avoid missing the detection of any splices.

The mechanical splice configuration tab 830 may include a splice detection algorithm field 834. In one implementation, a user may select one of three different mechanical splice detection algorithms.

The mechanical splice configuration tab 830 may include a horizontal edge algorithm field 835. This area contains all variables that pertain to how the horizontal edge mechanical splice detection algorithm works. The in row pixel increment value represents how many pixels within each row should be processed to come up with a score for this image row. For example, a 1 would mean processing every pixel while a 4 would mean processing every fourth pixel. In general, the higher the number, the less processing involved in detection.

The row gap value represents the gap between the current row being processed and the row to use when computing a gradient/edge score for this row. For example, a 1 would mean use the previous row while a 4 would mean use the row four rows before the current one when computing gradient scores. In general, a value of 3 typically is used.

The number of rows in splice value represents the number of rows a healthy mechanical splice takes up in an image from the top of the top row of clips to the bottom of the bottom row of clips. In general, if this value is improperly set, then the splice image will not be centered in the image. The threshold multiplier value is the multiplier applied to the running average of edge scores that determines the threshold level that must be passed in order for processed areas of the belt to be classified as part of a mechanical splice.

The mechanical splice configuration tab 830 may include a horizontal comb algorithm field 836. In general, this area contains all variables that pertain to how the horizontal comb mechanical splice detection algorithm works.

The hole spacing value represents the number of pixels between the center of adjacent zipper holes in the same row of clips. The slide iterations value represents the number of different comb offset locations to evaluate when attempting to fit the comb to a particular zone of image data. In general, the lower the number, the faster the algorithm will run. However, this is at the cost of the comb not matching up exactly with the image data. In practice, a value of 8 has been found to be acceptable.

The number of rows in splice value represents the number of rows a healthy mechanical splice takes up in an image from the top of the top row of clips to the bottom of the bottom row of clips. In general, if this value is improperly set, then the splice will not be centered in the image. The threshold multiplier value is the multiplier applied to the running average of comb scores that determines the threshold level that must be passed in order for processed areas of the belt to be classified as part of the mechanical splice.

The mechanical splice configuration tab 830 may include a vertical keys algorithm field 837. In general, this area contains all variables that pertain to how the vertical keys algorithm works.

The whole height value represents the height (in pixels) a zipper hole appears in the mechanical splice image. The pattern height value represents the number of rows between the bottom rivets of a clip in the top and the top rivets of a clip in the bottom row in a mechanical splice image.

The in row pixel increment value represents how many pixels within each row should be processed to come up with a score for this image row. For example, one (1) would mean process every pixel while four (4) would mean process every fourth pixel. In general, the higher the number, the less processing involved in detection.

The number of rows in splice value represents the number of rows a health mechanical splice takes up in an image from the top of the top row of clips to the bottom of the bottom row of clips. In general, if this value is improperly set, then the splice image will not be centered in the image. The threshold multiplier value is a multiplier applied to the running average of edge scores that determines the threshold level that must be passed in order for processed areas of the belt to be classified as part of a mechanical splice.

The mechanical splice configuration tab 830 may include a general algorithm statistics field 838. In one implementation, there are four processing statistics common to each detection algorithm.

One processing statistic may be initialization count. When the detection algorithm first starts processing the image data or if the control variables of a detection algorithm are changed, a certain amount of image data must be processed before a good estimate for the mechanical splice threshold level can be computed. This variable represents the number of rows still required before detection will take place. A value of zero (0) means that initialization is complete and splice detection can take place.

Another processing statistic is processing index. This variable represents the image slot number within the live belt image ring buffer that is currently being processed by the detection algorithm. Another processing statistic is images queued. This variable represents the number of image frames within the live belt image ring buffer that are waiting to be processed by the detection algorithm. If this variable is constantly growing, then the detection algorithm is running too slow and cannot keep up with the data being captured.

Another processing statistic is buffer overflows. If the detection algorithm cannot process data as fast as it is being captured, then eventually an overflow will occur. This variable represents the number of times a detection processing overflow has occurred.

Figure 74:
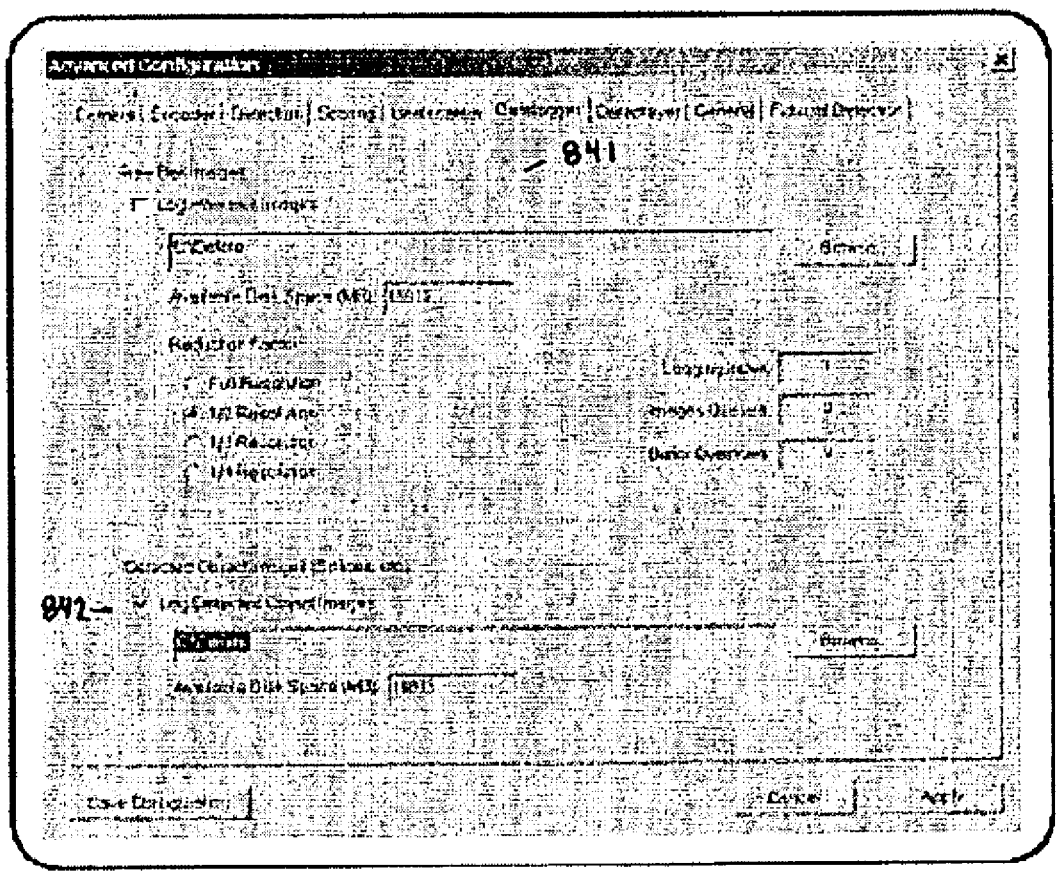
FIG. 74 illustrates one embodiment of a data logger configuration interface.

FIG. 74 illustrates a data logger configuration tab 840 that may be implemented by the BIS 20. In general, the data logger configuration tab 840 allows a user to control various data logger settings.

As shown, the data logger configuration tab 840 may include a raw belt images field 841. In general, this area specifies how, when and where live belt image data will be logged by BIS 20. If the log raw belt images box is checked, then live belt image data logging will be enabled.

The disk location field can be set by pressing the browse button in order to navigate through and select a folder via a folder viewer application. The available disk space variable represents the number of megabytes of free disk space on the disk where the live belt image data is stored. The reduction factor area allows the user to select the resolution of the logged live belt image data. The logging index variable represents the image slot number within the live belt image ring buffer that is currently being logged. The images queued variable represents the number of image frames within the live belt image ring buffer that are waiting to be logged. The buffer overflows variable represents the number of times a live belt image logging overflow has occurred.

The data logger configuration tab 840 may include a detected object images field 842. If the log detected object images box is checked, then every detected object that the BIS 20 detects will be logged to disk. The disk location field may be set by pressing the browse button in order to navigate through and select a folder via a folder viewer application. The available disk space variable represents the number of megabytes of free disk space on the disk where the detected object image data is stored.

Figure 75:
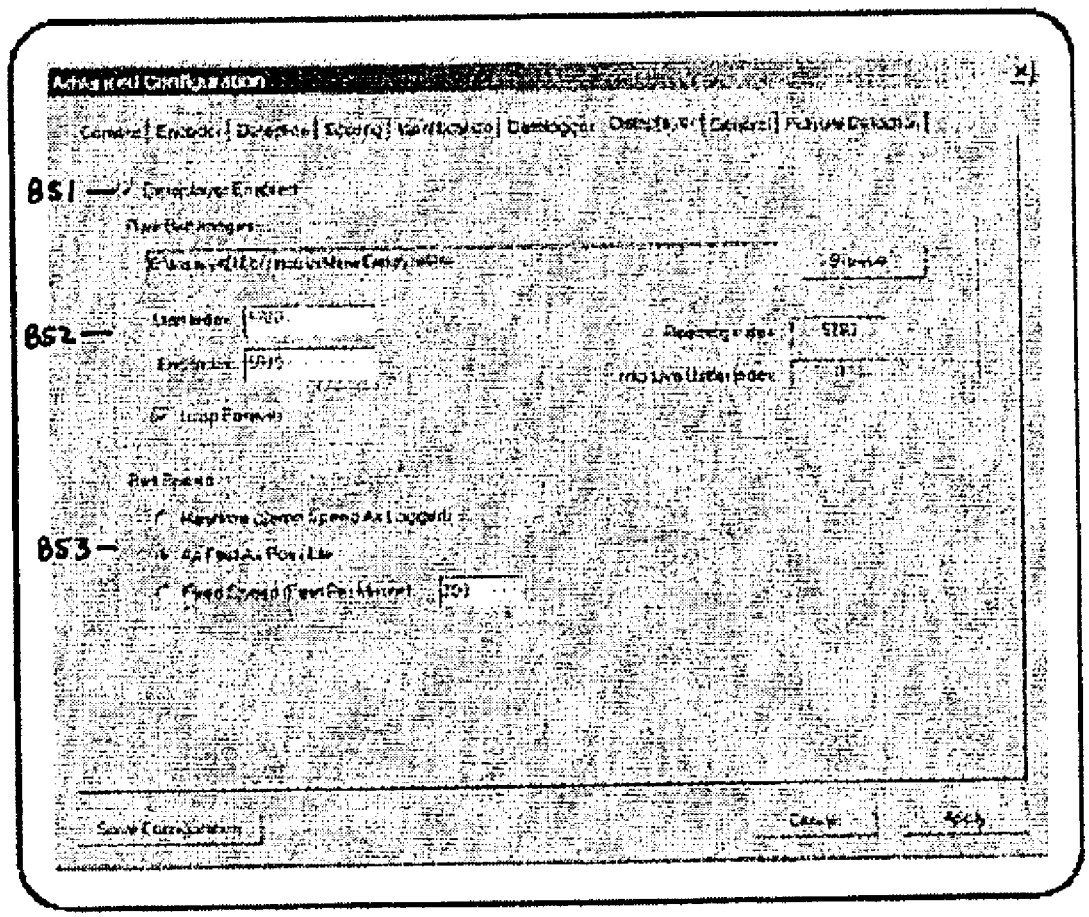
FIG. 75 illustrates one embodiment of a data player configuration interface.

FIG. 75 illustrates a data player configuration tab 850 that may be implemented by the BIS 20. In general, the data player configuration tab 850 allows a user to control various data player settings.

As shown, the data player configuration tab 850 may include a data player enabled field 851. In general, to enable the data player mode, this box must be checked.

The data player configuration tab 850 may include a raw belt images field 852. This area specifies where the live belt images are located on disk that should be used and the range of image numbers to use during playback. The disk location field may be set by pressing the browse button in order to navigate through and select a folder via a folder viewer application.

The start index indicates the image number from which playback should start. The end index indicates the image number at which playback should stop. The loop forever box, if checked, enables looping over the same range of images. The reading index indicates the current image number being read from disk and loaded into the live belt image ring buffer. The into live belt buffer indicates the image ring buffer slot number that the current image is being loaded into from disk.

The data player configuration tab 850 also may include a belt speed field 853 for indicating the speed of the belt.

Figure 76:
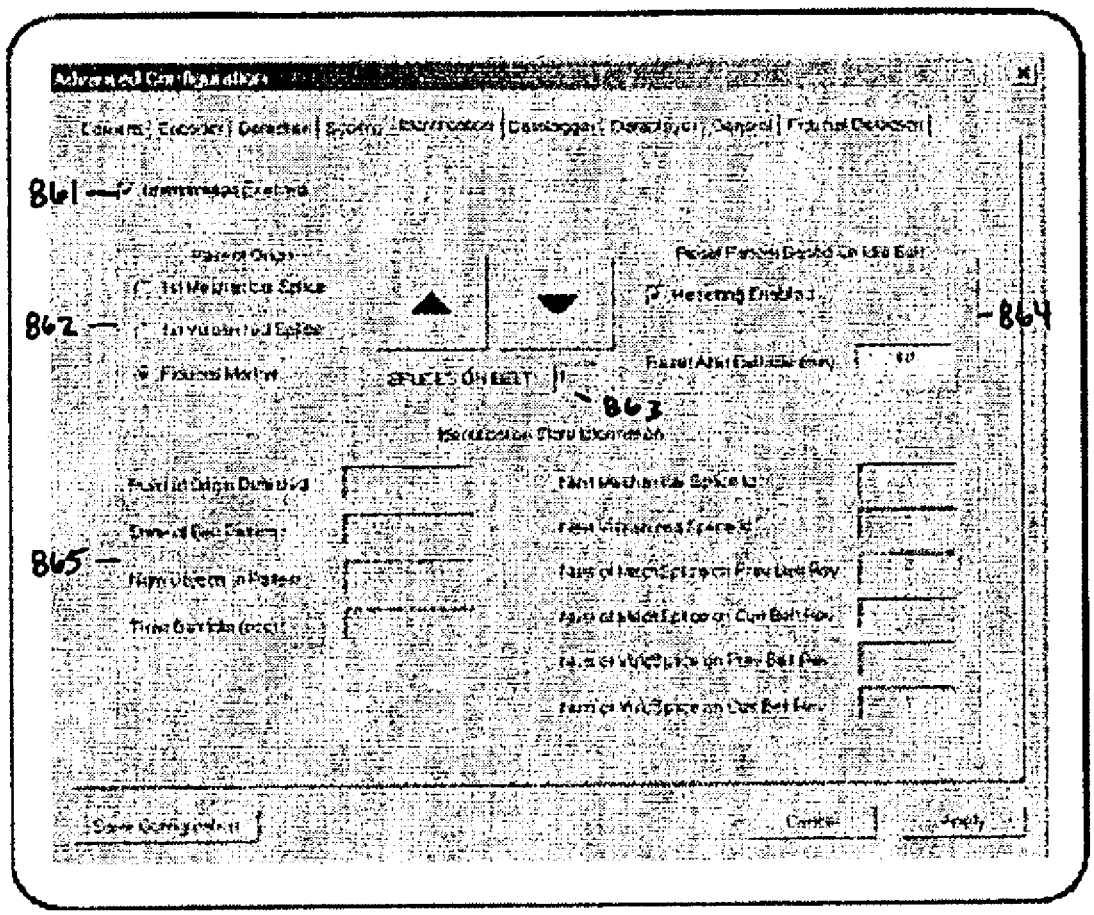
FIG. 76 illustrates one embodiment of an identification configuration interface.

FIG. 76 illustrates an identification configuration tab 860 that may be implemented by the BIS 20. In general, the identification configuration tab 860 may allow a user to control various identification configuration settings.

As shown, the identification configuration tab 860 may include an identification enabled field 861. If checked, then identification is enabled. Otherwise identification is disabled.

The identification configuration tab 860 may include a point of origin field 862. This field may represent the type of object that the BIS 20 should use as a reference for the point of origin on the belt. Selecting first mechanical splice makes the first detected mechanical splice the point of origin. Selecting first vulcanized splice makes the first vulcanized splice (detected by detecting a fiducial patch pair) the point of origin. Selecting fiducial marker makes the special fiducial marker patch pair (that defines the point of origin) the point of origin on the belt.

The identification configuration tab 860 may include a splice on belt field 863. This field may be set if either the point of origin is selected to be the first mechanical splice or the first vulcanized splice. The first mechanical splice may be set to be the number of mechanical splices on the belt. The first vulcanized splice may be set to be the number of vulcanized splices on the belt that have fiducial markers installed on them such that they may be detected by the BIS 20.

The identification configuration tab 860 may include a reset pattern based on idle belt field 864. This area may be used to configure how the identification process should interpret the belt being idle (stopped). Resetting enabled, if checked, enables the resetting of object identification tags if the belt is idle for more than the configured period of time. The reset after belt idle value indicates the number of minutes that a belt may be idle before resetting the identification state.

The identification configuration tab 860 may include an identification state information field 865. This area may be used to display the current internal state of the identification system. The point of origin detected field indicates whether or not the point of origin has been detected. The state of belt pattern field indicates whether the belt pattern is known. The number of objects in pattern field provides the number of objects on the belt. The time belt idle field indicates the number of seconds that the belt has been idle.

The next mechanical splice ID indicates the ID that will be assigned to the next detected mechanical splice. The next vulcanized splice indicates the ID that will be assigned to the next detected vulcanized splice. The number of mechanical splices on last belt revolution indicates the number of mechanical splices that were detected on the last belt revolution. The number of mechanical splices on current belt revolution indicates the number of mechanical splices that have been detected so far on the current belt revolution. The number of vulcanized splices on last belt revolution indicates the number of vulcanized splices that were detected on the last belt revolution. The number of vulcanized splices on current belt revolution indicates the number of vulcanized splices that have been detected so far on the current belt revolution.

Figure 77:
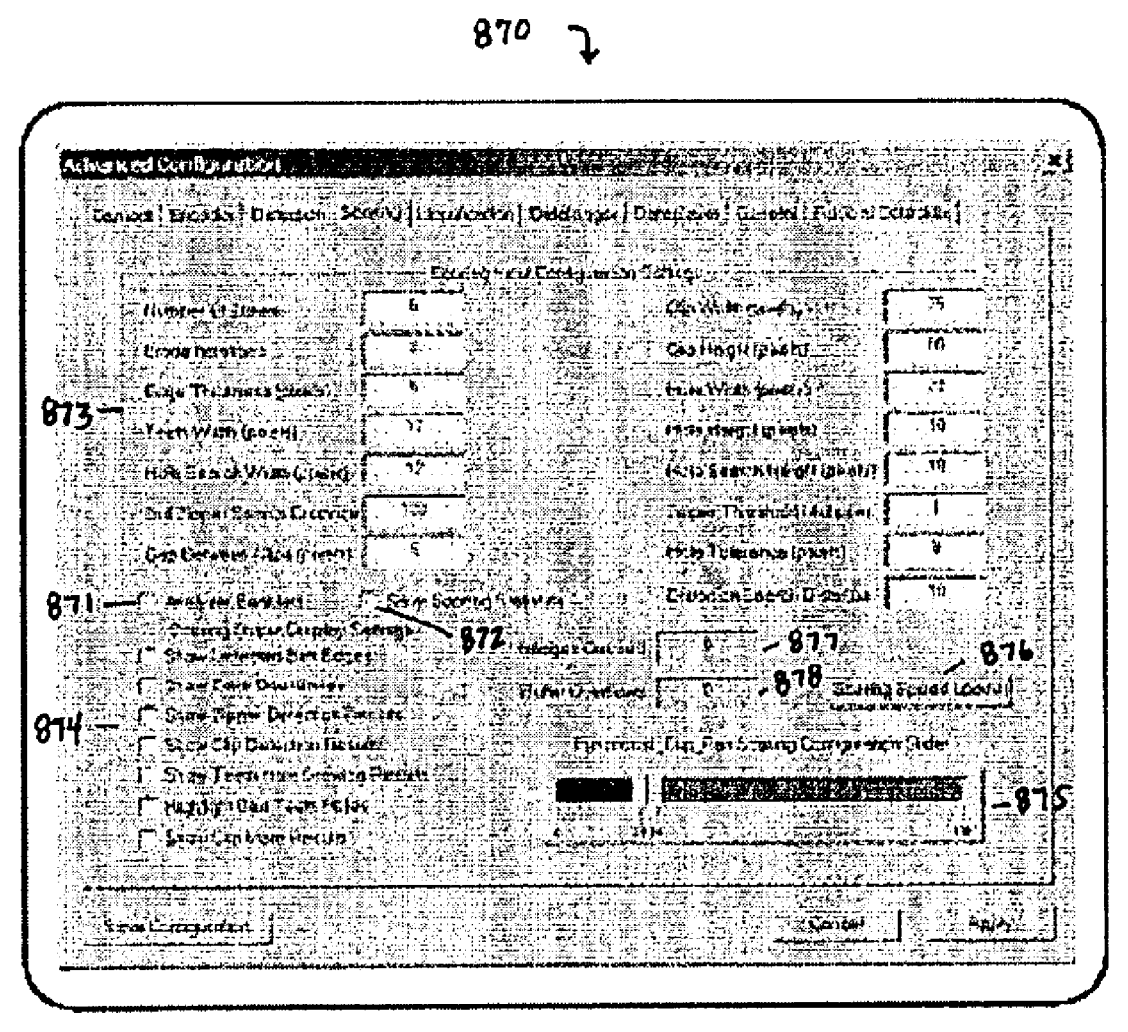

FIG. 77 illustrates a mechanical splice scoring configuration tab 870 and that may be implemented by the BIS 20. In general, the mechanical splice scoring configuration tab

870 allows a user to control various mechanical splice scoring configuration settings.

As shown, the mechanical splice scoring configuration tab 870 may include an analyzer enabled field 871. If enabled, detected mechanical splices will be analyzed for defects and scored by a primary zipper hole method.

The mechanical splice scoring configuration tab 870 may include a save scoring statistics field 872. If enabled, the scoring algorithm will log data to disk while it analyzes the mechanical splice image. This data may be examined off-line to determine the source of scoring failure.

The mechanical splice scoring configuration tab 870 may include a scoring input configurations field 873. In general, this area allows a user to configure various setting that control how the analyzing algorithm works.

The number of zones field indicates how many zones into which the image should be split. The erode iterations field indicates how many times the image should be eroded in order to enhance the zipper holes. The edge thickness field indicates the thickness of the edges in the vertical edge magnitude image. The teeth width field indicates the width (in pixels) of a clipped tooth The hole search width and height field indicates how far to search from the estimated zipper hole center for a better hole center. The second zipper search distance field indicates how many rows may separate the top and bottom row of clips taking into account damaged clips. The gap between clips field indicate the number of pixels between two clips.

The clip width field indicates the number of pixels wide a clip is in the image. The clip height field indicates the number of pixels from the top of the zipper hole to the top of the clip in the image. The hole width field indicates the number of pixels wide a zipper hole is in the image. The hole height field indicates the number of pixels high a zipper hole is in the image. The zipper threshold multiplier indicates the multiplier that should be used to multiply the zipper response filter mean response by in order to compute a threshold level for zipper detection. The hole tolerance field indicates the number of pixels that the zipper hole can deviate from the median zipper hole height before it is deemed defective. The distortion search distance field indicates the number of different off-set zipper detection filters to use to detect the zipper location.

The mechanical splice scoring configuration tab 870 may include a scoring output display settings field 874. In general, this area may control what parts of the analyzing results get displayed on top of the mechanical splice image when displayed in the object window.

The show detected belt edges field, if enabled, shows the detected belt edges on the image. The show zone boundaries field, if enabled, shows the different zone boundary lines on the image. The show zipper detection results field, if enabled, shows the center location of the estimated and defined zipper holes and the location of the detected pin in each section. The show clip detection results field, if enabled, shows bounding boxes around the detected clips in at top and bottom row on the image. The show teeth hole growing results field, if enabled, shows bounding boxes around each zipper hole on the image. The highlight bad teeth holes field, if enabled, shows a box with an "x" in it on each zipper hole that was determined to be defective on the image. The show clip mate results field, if enabled, shows clip mate pairs by drawing a line connecting the bottom and top clips on the image.

The mechanical splice scoring configuration tab 870 may include a functional clip pair scoring configuration slider field 875. The two slider positions may be changed in order to set the different levels of scoring. Scores in red may be used to show splices that have serious defects. Scores in yellow may be used to show splices that have marginal defects. Scores in green may represent splices that have minor, if any, defects.

The mechanical splice scoring configuration tab 870 may include a scoring speed loader field 876. The user may run previously detected mechanical splices through the splice analyzer by using the scoring speed loader. Clicking on the scoring speed loader button brings up a disk folder viewer window. The user may navigate to the folder containing the previously detected mechanical splices. The BIS 20 will load and score each mechanical splice using the scoring configuration settings one at a time. The scoring of the splices will continue until all previously detected splices have been analyzed or until there is a break in the image sequence numbers.

The mechanical splice scoring configuration tab 870 may include an images queued field 877. This field may specify the number of images currently in the analyzer queue that are waiting to be analyzed. It should be noted that if this number is constantly increasing, then an overflow may be imminent. The mechanical splice scoring configuration tab 870 also may include a data overflow field 878. This field may represent the number of analyzer image overflows that have occurred.

Figure 78:
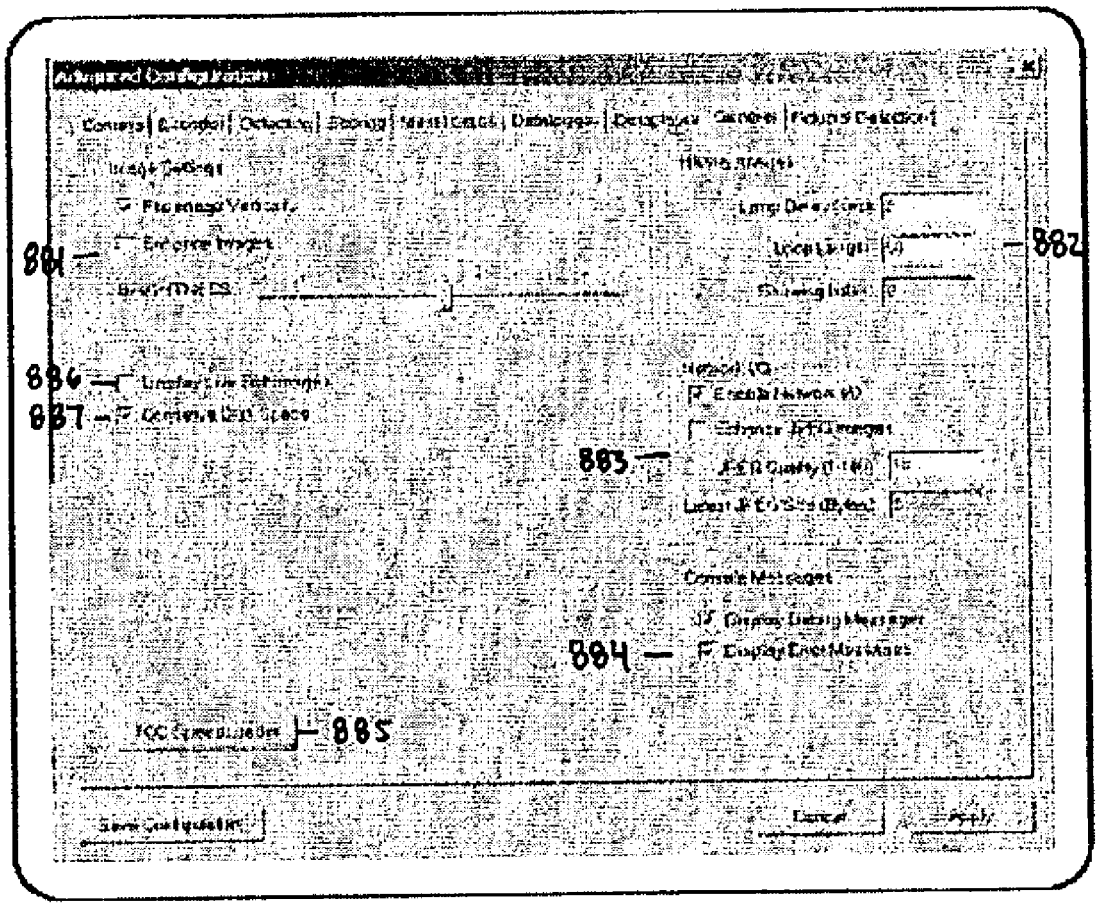
FIG. 78 illustrates one embodiment of a general configuration interface.

FIG. 78 illustrates a general configuration tab 880 that may be implemented by the BIS 20. In general, the general configuration tab 880 may allow a user to control various general configuration settings.

As shown, the general configuration tab 880 may include an image settings field 881. This area may control how the images in the object image area of the main graphical user interface screen appear. The flip image vertically field, if enabled, flips the image vertically, before displaying it in the object image area window. The enhance image field, if enabled, histogram equalizes the image before it is displayed in the object image area window. The brightness slider bar controls by how much intensity each pixel in the image is increased/decreased before it is displayed in the object image area window.

The general configuration tab 880 may include a history images field 882. This area may control the looping update mode of the object image area. The loop delay field indicates how often to update the object image area window when in looping mode. The loop links field specifies how far back from the current number of detected objects to display before going back to the latest detected object when in looping mode. The showing index field represents the object detection number of the current object being displayed in the object image area window.

The general configuration tab 880 may include a network IO field 883. This area may control all communication setting between the BIS 20 and a surface server machine. The enable network IO field enables networking to be transmitted from the BIS 20 to the surface server machine grid. The enhanced JPEG images enables detected object image data to be histogram equalized before sending the image data to the surface server machine. The JPEG quality (1–100) field specifies the quality level to use when compressing the images into JPEG format. The latest JPEG size field represents the size of the last object image that was transmitted to the surface server machine.

The general configuration tab 880 may include a console messages field 884. This area may control what type of messages are displayed on the console window. The display debugged messages field enables debugging information to be displayed on the consol window. The display error messages field enables error messages to be displayed on the console.

The general configuration tab 880 may include a TOC speed loader field 885. A user may load in previously detected objects form disk in order to view them within BIS 20 by clicking the TOC speed loader button. This will bring up a folder navigation window. The user then navigates through the disk folder and selects the folder that contains the previously detected objects.

The general configuration tab 880 may include a display live belt images field 886. If enabled, a window is brought up that displays images of latest data. A window may be updated by a rate of five times per second. As such, the user is not seeing the entire belt but rather snap shots of it. The general configuration tab 880 also may include a conserve disk space field 887. If enabled, BIS 20 is directed to conserve disk space. This may mean that when the BIS 20 starts up, it will purge outdated data. In addition, BIS 20 may conserve disk space while running by writing over images in the TOC list.

Figure 79:
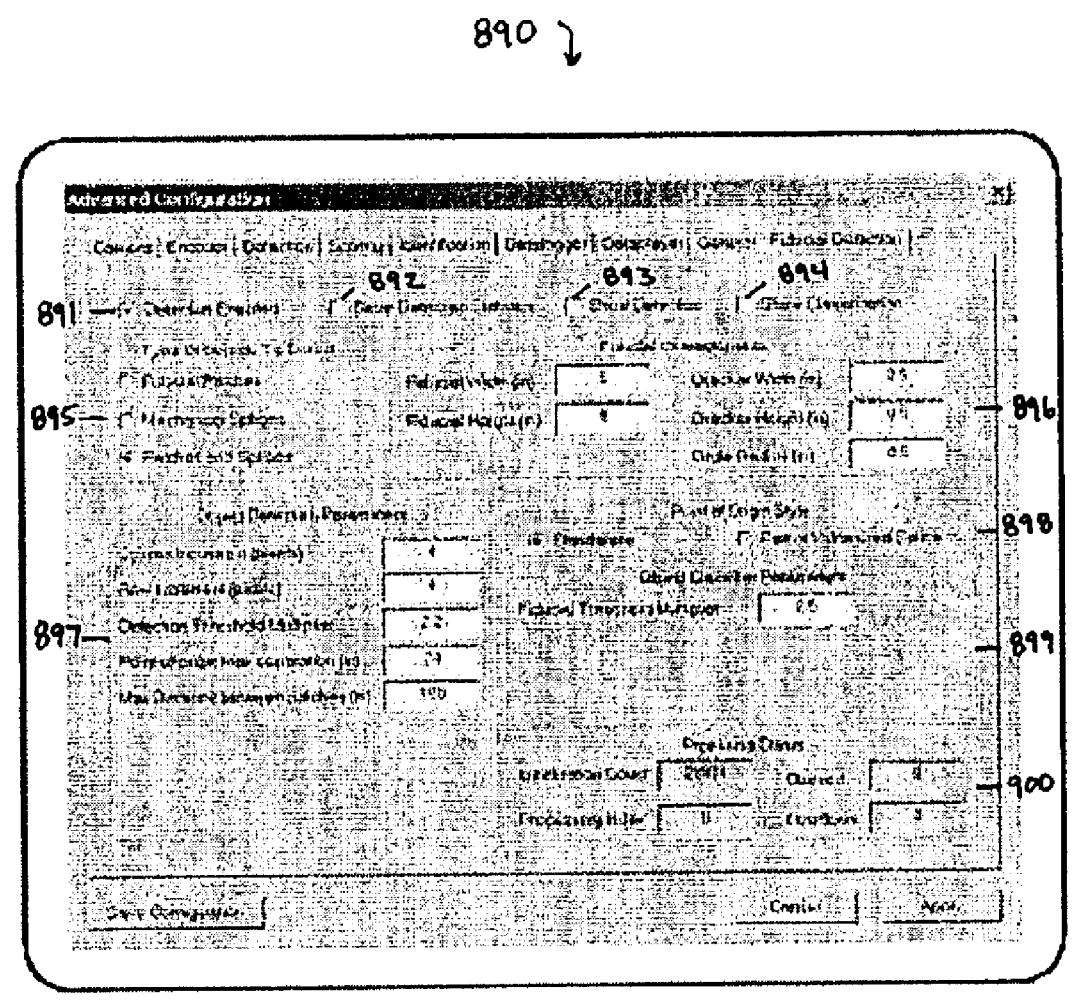

FIG. 79 illustrates a fiducial detection configuration tab 890 that may be implemented by the BIS 20. In general, the fiducial detection configuration tab 890 may allow a user to control various fiducial detection configuration settings.

As shown, the fiducial detection configuration tab 890 may include a detection enabled field 891. If this box is checked, mechanical splices and/or fiducial patch detection by the fiducial object detection and classification algorithm will be enabled.

The fiducial detection configuration tab 890 may include a save detection statistics field 892. If this box is checked, then the detection and classification algorithm will save information to disk while running. This may slow down the algorithm, but maybe useful in debugging the algorithm off line by processing the logged data if mechanical splices and/or fiducial patches are not being detected and/or classified.

The fiducial detection configuration tab 890 may include a show detection field 893. If this box is checked, a graph window may appear on the screen. The graph window may show the processing scores of the image data and the current detection threshold level. By inspecting the graph as the system runs, an appropriate threshold multiplier level may be set that is significantly above the background belt score and low enough to avoid missing the detection of any splices and/or fiducial patches.

The fiducial detection configuration tab 890 may include a show classification field 894. If this boxed is checked, then a graph window may appear on the screen. The graph window may show the classification scores of the image data and the current fiducial patch threshold level. By inspecting the graph as the system runs, and appropriate threshold multiplier level may be set that is significantly above the background score and low enough to avoid classifying any fiducial patches as mechanical splices.

The fiducial detection configuration tab 890 may include a type of objects to detect field 895. The fiducial detection algorithm may be used to detect fiducial patches and/or mechanical splices. This area allows the user to select the type of objects to be detected by the fiducial algorithm. In one implementation, the user may select to detect only fiducial patches, only mechanical splices, or both fiducial patches and mechanical splices.

The fiducial detection configuration tab 890 may include a fiducial characteristics field 896. This area may allow the user to set the geometric characteristics of the fiducial patches that the system will be detecting. The fiducial width field indicates the width of the fiducial patch specified in inches. The fiducial height field indicates the height of the fiducial patch specified in inches. The checker width field indicates the width of one of the checker board fiducial squares specified in inches. The checker height field indicates the height of one of the checker board fiducial squares specified in inches. The circle radius field indicates a radius of the circle located in the center of the fiducial patch specified in inches.

The fiducial detection configuration tab 890 may include an object detection parameters field 897. This area may allow the user to configure or tune the fiducial algorithm.

The column increment value represents how many pixels within each row should be processed to come up with a score for this image row. For example, a 1 would mean process every pixel while a 4 would mean process every fourth pixel. In general, the higher the number, the less processing involved in detection. However, this may lower the signal-to-noise scores between background belt and objects.

The row increment value represents how often to sample and process rows in the captured data. For example, a 1 would mean process every row while a 4 would mean process every fourth row. In general, the higher the number, the less processing involved in detection. However, this may lower the signal-to-noise scores between background belt and objects.

The detection threshold multiplier is the multiplier applied to the running average of scores that determines the threshold level that must be passed in order for processed areas of the belt to classified as part of either a mechanical splice or a fiducial patch. The point of origin masks separation value represents the maximum distance by which two patches can be separated in order for the BIS 20 to classify them as the fiduciary-of-origin. If two consecutive patches are separated by more than this distance, then they will be classified as a vulcanized splice.

The max distance between patches value represents the maximum distance by which two patches that make up part of a vulcanized splice are expected to be separated in order to be detected by the BIS 20. In general, this value should be set slightly higher than the length of the longest vulcanized splice on the belt. If two consecutive patches are detected to be separated by more than this distance, then the BIS 20 will classify the detection as a false positive and ignore this possible splice.

The fiducial detection configuration tab 890 may include a point of origin style field 898. This area may allow a user to configure how the fiducial point-of-origin is installed on the belt that BIS 20 is inspecting. The standalone field indicates that the fiducial patches that make up the point-of-origin are installed on the belt away from all other patches. The part of vulcanized splice field indicates that the fiducial patches that make up the point-of-origin are installed on the belt as part of a vulcanized splice. This means that one of the patches is part of the point-of-origin and is also one of the patch-pair that is used to mark the beginning and end of a vulcanized splice.

The fiducial detection configuration tab 890 may include an object classifier parameters field 899. This area may allow the user to configure parameters that are relevant to the classification of detected objects. The fiducial threshold multiplier is the multiplier applied to the running average of scores that determines the threshold level that must be passed in order for detected objects to be classified as a fiducial patch.

The fiducial detection configuration tab 890 also may include a processing field 900. In general, this area may be used to provide feedback to the user as to the as to the state of the fiducial algorithm. When that detection algorithm first starts processing the image data or if the object detection parameters of the detection algorithm are changed, a certain amount of image data must be processed before a good estimate for the object detection threshold level is obtained. The initialization count variable represents the number of rows still required before detection will take place. A value of zero (0) means that initialization is complete and object detection can take place.

The processing index variable represents the image slot number within the live belt image ring buffer that is currently being processed by the detection algorithm. The queued variable represents the number of image frames within the live belt image ring buffer that are waiting to be processed by the detection algorithm. If this variable is constantly increasing, the detection algorithm may be running too slow and cannot keep up with the data being captured. The overflows variable represents the number of times a detection overflow has occurred. If the detection algorithm cannot process data as fast as it is being captured.

Figure 80:
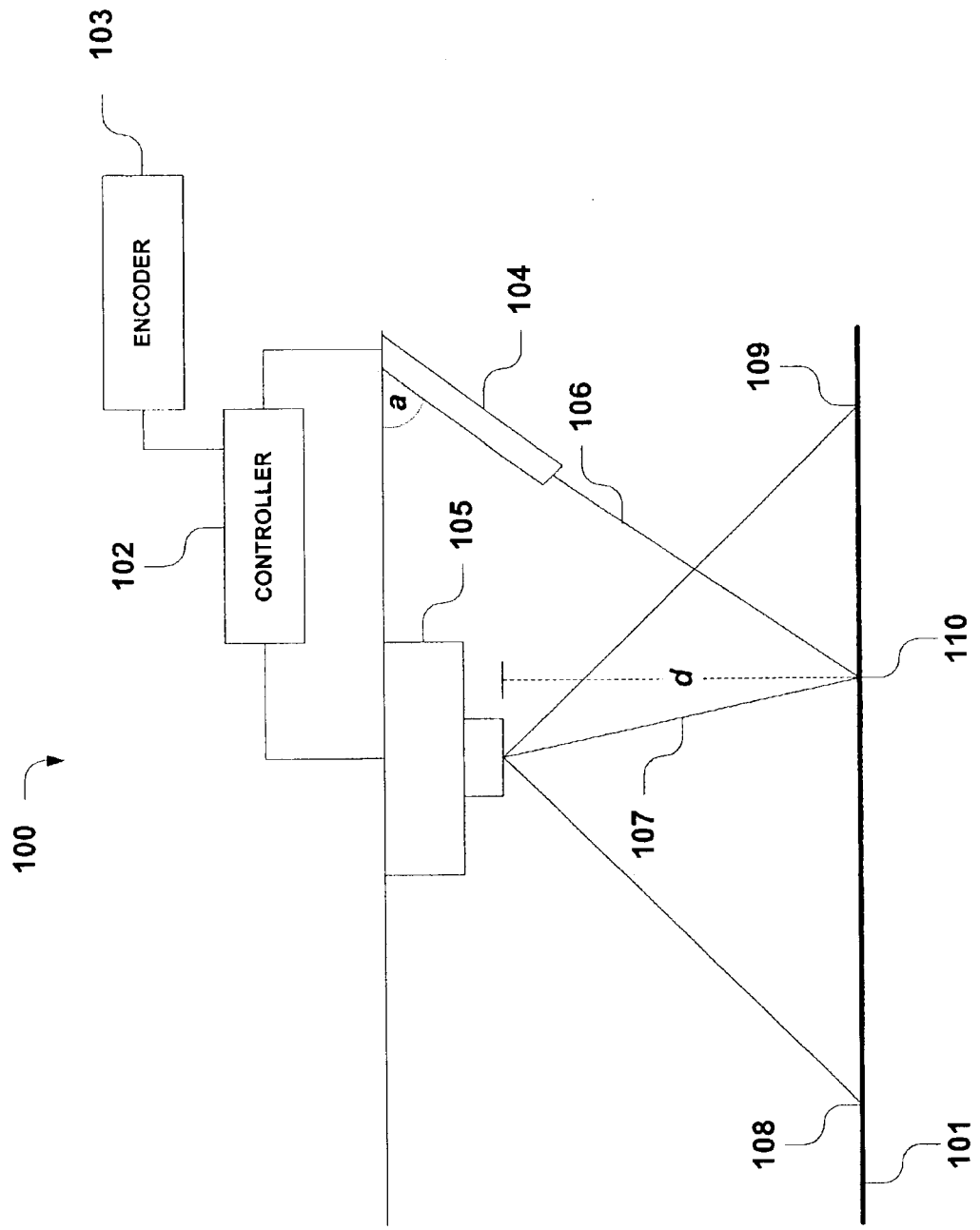
FIG. 80 illustrates one embodiment of a conveyor belt system.

FIG. 80 illustrates another embodiment of a conveyor belt system 100. In one general aspect, the conveyor belt system 100 is directed to systems and techniques for detecting defective conditions in a conveyor belt 101 that may contribute to belt failure and for alerting management and/or maintenance personnel (e.g., via audio or visual alarm) of such conditions prior to belt failure. For simplicity, the basic components are depicted. However, as would be understood by one of ordinary skill in the art, the system described below may include various other components and structures in actual implementation consistent with aspects of the present invention.

As shown, the conveyor belt system 100 includes a controller 102 in communication with an encoder 103, a focused light source 104 and a camera 105. In general, the controller 102 may be implemented as one or more computers and/or computer systems for performing the functions described herein. Examples include, but are not limited to, a general-purpose computer, a special-purpose computer, a personal computer (PC), a workstation, a network server, a terminal, a virtual machine, a laptop computer, a microprocessor, an integrated circuit, or any other device, machine, tool, equipment, component, or some combination thereof capable of responding to and executing instructions.

The encoder 103 may perform functions, such as, computing the current belt speed and position, computing desired digitized line rate based on the current belt speed, and recording the belt speed—including monitoring the amount of time the belt is idle. In one implementation, the controller 102 interacts with the encoder 103 to control the speed of image capture.

The focused light source 104 is configured to direct focused light 106 at the conveyor belt 101. In one embodiment, the focused light source 102 may include a laser that generates a laser beam. As depicted, the focused light 103 source may be aimed at an angle a with respect to a baseline. In most cases, reflected light 107 will occur as the focused light 106 contacts and is reflected by the conveyor belt 101. That is, apart from having defects such as holes and tears, the belt 101 generally is solid.

The camera 105 may be configured to detect and receive the reflected light 107. In one implementation, the camera 105 is a line scan camera that may provide a digitized image containing one row of pixels. The field of view for the camera 102 may be defined between the first pixel 108 and the last pixel 109 in the row of pixels. As shown in the figure, the focused light 105 is reflected by the belt 101 within the field of view of the camera 105 at an intermediate pixel location 110.

In one implementation, the camera 105 reports the detection of the reflected light 107 to the controller 102. Based on the pixel location 110, the controller 102 can compute the distance d to the pixel. In general, the distance d may be representative of the range separating the conveyor belt 101 and the camera 105. In one embodiment, the controller 102 calculates a range profile for a row of pixels spanning the width of the belt. In general, the range profile of the belt surface will be calculated at relatively short intervals so that data for most of the conveyor belt 101 is collected. For example, data maybe collected for every 2 inches along the length of the belt 101.

In general, the range data will be collected for portions of the conveyor belt 101 that are capable of reflecting the focused light 106. Because the conveyor belt 101 may not be completely flat, it is expected for the range values to vary. In some cases, however, the conveyor belt 101 may include defects such as holes and tears that prevent the reflection of the focused light 105. For these portions, range data is unavailable and the distance d will be reported as zero. It also should be noted that for defects such as raised edges, the distance d will be reported to be lower than for the rest of the belt.

Figure 81:
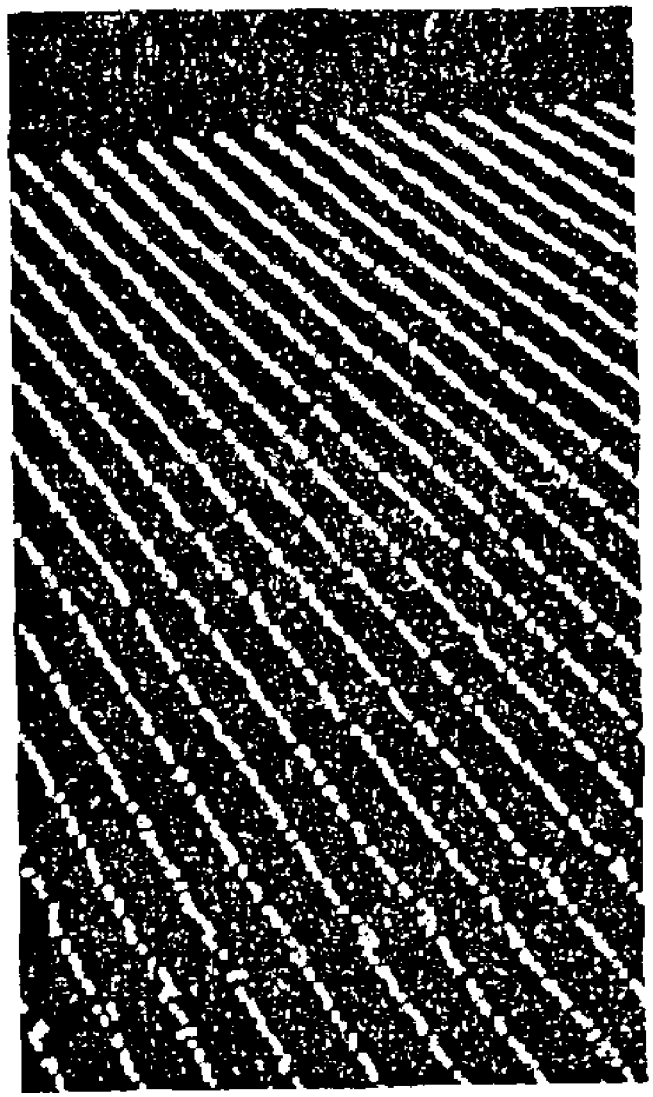
FIG. 81 illustrates one embodiment of three-dimensional belt topography.

In one implementation, the controller 102 may process the collected range data to create a range point cloud or "dust cloud" image. In general, the range point cloud provides a three-dimensional topography of the belt 101 which may be visually displayed to a user. FIG. 81 illustrates one embodiment of a belt topography that may be generated according to the present invention. By viewing the topography, is possible to check the belt 101 for mechanical splice defects (e.g., missing clips, broken clips, broken pins, missing rivets, and/or worn or trailing edges), vulcanized splice defects (e.g., tearing of upper belt ply and/or delaminating of belt plies), and/or belt material defects (e.g., holes, tears, "flappers", gouges, and/or excessive scoring).

In some embodiments, the functionality and/or components of the conveyor belt system 100 may be implemented by a BIS 20. For example, the BIS 20 may display a three-dimension topography of the belt surface to a user in addition to performing mechanical splice detection, vulcanized splice detection, and/or object detection, as described above.

A number of implementations have been described. Nevertheless, it will be understood that various modifications may be made and that other implementations are within the scope of the following claims. In particular, fiduciary markings are not required to be associated with a vulcanized splice. Namely, one or more fiduciary markings may be placed anywhere one the surface of the belt and monitored (e.g., for stretching) to provide an indication of belt quality. Furthermore, while one example of a fiduciary marking is a checkerboard pattern, any type of recognizable mark, pattern, line, or shape may be used.

Other embodiments are within the scope of the following claims.

What is claimed is:

1. An inspection system for detecting and reporting conditions of a conveyor belt, the system comprising:
   a controller comprising a splice detection program for receiving image data from at least one camera structured and arranged to capture an image of a portion of a conveyor belt, for detecting a splice in the image of the portion of the conveyor belt by processing the received image data, and for generating status information associated with the portion of the conveyor belt based on a detected splice.

2. The system of claim 1, wherein the controller classifies the detected splice.

3. The system of claim 2, wherein the controller analyzes the detected splice based on an assigned classification.

4. The system of claim 1, wherein the detected splice comprises a mechanical splice.

5. An inspection system for detecting and reporting conditions of a conveyor belt, the system comprising:

a controller for receiving image data from at least one camera structured and arranged to capture an image of a portion of a conveyor belt, for detecting an object in the portion of the conveyor belt based on the received image data, and or generating status information associated with the portion of the conveyor belt based on the detected object, wherein the detected object comprises a mechanical splice, and the controller detects the mechanical splice by edge filtering the image data.

6. An inspection system for detecting and reporting conditions of a conveyor belt, the system comprising:

a controller for receiving image data from at least one camera structured and arranged to capture an image of a portion of a conveyor belt, for detecting an object in the portion of the conveyor belt based on the received image data, and for generating status information associated with the portion of the conveyor belt based on the detected object, wherein the detected object comprises a mechanical splice, and the controller detects the mechanical splice by searching for a zipper pattern in image data.

7. An inspection system for detecting and reporting conditions of a conveyor belt, the system comprising:

a controller for receiving image data from at least one camera structured and arranged to capture an image of a portion of a conveyor belt, for detecting an object in the portion of the conveyor belt based on the received image data, and for generating status information associated with the portion of the conveyor belt based on the detected object, wherein the detected object comprises a mechanical splice, and the controller detects the mechanical splice by searching for a hole pattern in the image data.

8. An inspection system for detecting and reporting conditions of a conveyor belt, the system comprising:

a controller for receiving image data from at least one camera structured and arranged to capture an image of a portion of a conveyor belt, for detecting an object in the portion of the conveyor belt based on the received image data, and for generating status information associated with the portion of the conveyor belt based on the detected object, wherein the detected object comprises a mechanical splice, and status information comprises a score assigned to the detected mechanical splice by the controller.

9. The system of claim 8, wherein the score is based on a zipper hole pattern.

10. The system of claim 8, wherein the score is based on a number of functional clips included in detected mechanical splice.

11. The system of claim 1, wherein the detected object comprises a vulcanized splice.

12. An inspection system for detecting and reporting conditions of a conveyor belt, the system comprising:

a controller for receiving image data from at least one camera structured and arranged to capture an image of a portion of a conveyor belt, for detecting an object in the portion of the conveyor belt based on the received image data, and for generating status information associated with the portion of the conveyor belt base on the detected object, wherein the detected object comprises a vulcanized splice, and the controller detects the vulcanized splice by locating at least one fiduciary marking corresponding to the location of the vulcanized splice.

13. The system of claim 12, wherein the controller locates the at least one fiduciary marking by edge filtering.

14. The system of claim 12, wherein the fiduciary marking is vulcanized to the conveyor belt.

15. The system of claim 12, wherein the fiduciary marking comprises at least one of a mark, patch, pattern, shape, line or grid.

16. The system of claim 12, wherein the controller locates a center of one or more fiduciary markings.

17. The system of claim 12, wherein the controller locates a rotation angle of the at least one fiduciary marking.

18. The system of claim 12, wherein the controller locates a pair of fiduciary markings bounding the vulcanized splice.

19. The system of claim 1, wherein the controller detects a material defect in the belt.

20. The system of claim 19, wherein the material defect comprises at least one of a hole, rip, worn edge, score, or gouge in the conveyor belt.

21. The system of claim 1, wherein the controller detects a belt marking.

22. The system of claim 21, wherein the controller locates a center of one or more belt markings.

23. An inspection system for detecting and reporting conditions of a conveyor belt, the system comprising:

a controller for receiving image data from at least one camera structured and arranged to capture an image of a portion of a conveyor belt, for detecting an object in the portion of the conveyor belt based on the received image data, and for generating status information associated with the portion of the conveyor belt based on the detected object, wherein the detected object comprises a belt marking, and the controller analyzes the belt marking for distortion indicative of a defective condition of the conveyor belt.

24. The system of claim 23, wherein distortion comprises stretching of the belt marking.

25. The system of claim 23, wherein distortion comprises stretching between a pair of belt markings.

26. An inspectionn system for detecting and reporting conditions of a conveyor belt, the system comprising:

a controller for receiving image data from at least one camera structured and arranged to capture an image of a portion of a conveyor belt, for detecting an object in the portion of the conveyor belt based on the received image data, and for generating status information associated with the portion of the conveyor belt based on the detected object, wherein the detected object comprises a mechanical splice, and the belt marking is vulcanized to the conveyor belt.

27. The system of claim 21, wherein the belt marking comprises at least one of a mark, patch, pattern, shape, line, or grid.

28. The system of claim 1, wherein the controller detects reflected light.

29. The system of claim 28, wherein the reflected light is generated by a focused light source structured and arranged to direct focused light at the conveyor belt.

30. The system of claim 29, wherein the focused light source comprises a laser.

31. The system of claim 28, wherein the controller generates a range profile based on properties of the reflected light.

32. The system of claim 31, wherein the status information comprises a three-dimensional topography of the conveyor belt based on the range profile.

33. The system of claim 32, wherein the three-dimensional topography comprises at least one of a hole, rip, worn edge, splice, score, or gouge in the conveyor belt.

34. The system of claim 1, wherein the status information comprises a digital image of the detected splice.

35. An inspection system for detecting and reporting conditions of a conveyor belt, the system comprising:
   a controller for receiving image data from at least one camera structured and arranged to capture an image of a portion of a conveyor belt, for detecting an object in the portion of the conveyor belt based on the received image data, and for generating status information associated with the portion of the conveyor belt based on the detected object, wherein the status information comprises a plurality of digital images of the detected object captured over a period of time.

36. The system of claim 35, wherein the plurality of images shows degradation of the detected object over time.

37. An inspeection system for detecting and reporting conditions of a conveyor belt, the system comprising:
   a controller for receiving image data from at least one camera structured and arranged to capture an image of a portion of a conveyor belt, for detecting an object in the portion of the conveyor belt based on the received image data, and for generating status information associated with the portion of the conveyor belt based on the detected object, wherein the controller is configured to assign an identification tag to a detected object.

38. The system of claim 37, wherein the identification tag is assigned based on at least one of a reference object, a point-of-origin, recognized pattern, correlation between images, a health score, and object degradation.

39. The system of claim 1, wherein the status information comprises an alarm condition.

40. The system of claim 1, further comprising a user interface, in communication with the controller, configured to display a visual representation of the status information.

41. The system of claim 1, further comprising a remote element, in communication with the controller, for enabling remote access to the status information.

42. The system of claim 1, further comprising an encoder for monitoring speed of the conveyor belt.

43. A computer-implemented inspection method for detecting and reporting conditions of a conveyor belt, the method comprising:
   executing a splice detection program for:
      receiving image data from at least one camera structured and arranged to capture an image of a portion of a conveyor belt;
      detecting a splice in the image of the portion of the conveyor belt by processing the received image data; and
      generating status information associated with the portion of the conveyor belt based on a detected object splice.

44. The method of claim 43, further comprising displaying a visual representation of the status information.

45. The method of claim 43, further comprising classifying the detected splice.

46. The method of claim 43, wherein the detected splice comprises a mechanical splice.

47. The method of claim 43, wherein the detected splice comprises a vulcanized splice.

48. The method of claim 43, further comprising detecting a material defect in the conveyor belt.

49. The method of claim 43, further comprising detecting a belt marking.

50. The method of claim 43, further comprising detecting reflected light.

51. A splice detection program stored on a computer readable medium and executable by a computer, the splice detection program comprising instructions for:
   receiving image data from at least one camera structured and arranged to capture an image of a portion of a conveyor belt;
   detecting a splice in the image of the portion of the conveyor belt by processing the received image data; and
   generating status information associated with the portion of the conveyor belt based on a detected splice.

52. The program of claim 51, further comprising instructions for displaying a visual representation of the status information.

53. The program of claim 51, further comprising instructions for classifying the detected splice.

54. The program of claim 51, wherein the detected splice comprises a mechanical splice.

55. The program of claim 51, wherein the detected splice comprises a vulcanized splice.

56. The program of claim 51, further comprising instructions for detecting a material defect in the conveyor belt.

57. The program of claim 51, further comprising instructions for detecting a belt marking.

58. The program of claim 51, further comprising instructions for detecting reflected light.

59. An inspection system for detecting and reporting conditions of a conveyor belt, the system comprising a splice detection program comprising:
   means for receiving image data from at least one camera structured and arranged to capture an image of a portion of a conveyor belt;
   means for detecting a splice in the image of the portion of the conveyor belt by processing the received image data; and
   means for generating status information associated with the portion of the conveyor belt based on the a detected splice.

60. The system of claim 59, further comprising means for displaying a visual representation of the status information.

61. The system of claim 59, further comprising means for classifying the detected object splice.

62. The system of claim 59, wherein the detected splice comprises a mechanical splice.

63. The method of claim 59, wherein the detected splice comprises a vulcanized splice.

64. The method of claim 59, further comprising means for detecting a material defect in the conveyor belt.

65. The method of claim 59, further comprising means for detecting a belt marking.

66. The method of claim 59, further comprising means for detecting reflected light.

67. An inspection system for detecting and reporting condition of a conveyor belt, the system comprising:
- at least one camera arranged to capture an image of a portion of a conveyor belt;
- a focused light source arranged to direct focused light at the conveyor belt; and
- a controller comprising a detection program for receiving image data from the at least one camera, for detecting reflected light in the image of the portion of the conveyor belt by processing the received image data, for generating a range profile of the portion of the conveyor belt based on properties of the reflected light, and for generating a three-dimensional topography of the conveyor belt based on the range profile.

68. The system of claim 67, wherein the focused light source comprises a laser.

69. The system of claim 32, wherein the three-dimensional topography comprises at least one splice in the conveyor belt.

70. The system of claim 32, wherein the three-dimensional topography comprises at least one of a hole, rip, worn edge, score, or gouge in the conveyor belt.

* * * * *

UNITED STATES PATENT AND TRADEMARK OFFICE
CERTIFICATE OF CORRECTION

PATENT NO. : 6,988,610 B2
APPLICATION NO. : 10/341735
DATED : January 24, 2006
INVENTOR(S) : Fromme et al.

It is certified that error appears in the above-identified patent and that said Letters Patent is hereby corrected as shown below:

TITLE PAGE, ITEM (56)
REFERENCES CITED

Delete "3,512,662 01/79 Strydorn" and substitute therefor --3,512,662 5/1970 Strydorn--.

Delete "DE 3611125A 08/1987" and substitute therefor --DE 3611125A 10/1987--.

COLUMN 5

Line 49, delete "In come case," and substitute therefor --In some cases,--.

COLUMN 8

Line 28, delete "As shown, the UPS 220 and may be" and substitute therefor --As shown, the UPS 220 may be--.

COLUMN 9

Line 55, delete "and/or at the direction a program", and substitute therefor --and/or at the direction of a program--.

COLUMN 14

Line 17, delete "data mode, described above.", and substitute therefor --data mode described above.--

COLUMN 15

Line 58, delete "raw image top", and substitute therefor --raw image (top)--.

COLUMN 17

Line 30, delete "of stress.", and substitute therefor --of stresses.--

COLUMN 24

Line 64, delete "rivet patters", and substitute therefor --rivet patterns--.

UNITED STATES PATENT AND TRADEMARK OFFICE
CERTIFICATE OF CORRECTION

PATENT NO.       : 6,988,610 B2
APPLICATION NO.  : 10/341735
DATED            : January 24, 2006
INVENTOR(S)      : Fromme et al.

It is certified that error appears in the above-identified patent and that said Letters Patent is hereby corrected as shown below:

COLUMN 25

Line 55, delete "algorthm 60", and substitute therefor --algorithm 60--.

Line 56, delete "algorthm 60", and substitute therefor --algorithm 60--.

Line 63, delete "algorthm 60", and substitute therefor --algorithm 60--.

COLUMN 26

Line 6, delete "algorthm 60", and substitute therefor --algorithm 60--.

Line 32, delete "(checkerboard patter)" and substitute therefor --(checkerboard pattern)--.

COLUMN 34

Line 36, delete "Table 2 an example", and substitute therefor --Table 2 shows an example--.

COLUMN 43

Line 14, delete "various setting", and substitute therefor --various settings--.

Line 22, delete "tooth  The hole", and substitute therefor --tooth.  The hole---.

COLUMN 45

Line 35, delete ", but maybe useful", and substitute therefor --, but may be useful--.

COLUMN 47

Line 1, delete "as to the as to the state", and substitute therefor --as to the state--.

COLUMN 48

Lines 33-34, delete "is possible" and substitute therefor --it is possible--.

COLUMN 49

Line 17, Claim 5, delete "and or generating", and substitute therefor --and for generating--.

UNITED STATES PATENT AND TRADEMARK OFFICE
CERTIFICATE OF CORRECTION

PATENT NO. : 6,988,610 B2
APPLICATION NO. : 10/341735
DATED : January 24, 2006
INVENTOR(S) : Fromme et al.

It is certified that error appears in the above-identified patent and that said Letters Patent is hereby corrected as shown below:

COLUMN 50

Line 8, Claim 12, delete "base on the", and substitute therefor --based on the--.

Line 52, Claim 26, delete"inspectionn", and substitute therefor --inspection--.

COLUMN 51

Line 64, Claim 43, delete "detected object splice.", and substitute therefor --detected splice.--.

COLUMN 52

Line 57, Claim 61, delete "detected object splice.", and substitute therefor --detected splice.--.

Signed and Sealed this

Thirty-first Day of October, 2006

JON W. DUDAS
*Director of the United States Patent and Trademark Office*